United States Patent
Takahashi et al.

(10) Patent No.: US 11,744,149 B2
(45) Date of Patent: Aug. 29, 2023

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Yusuke Takahashi, Sodegaura (JP); Tasuku Haketa, Otemachi (JP); Hirokatsu Ito, Sodegaura (JP); Yu Kudo, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 17/884,732

(22) Filed: Aug. 10, 2022

(65) Prior Publication Data

US 2022/0399505 A1    Dec. 15, 2022

Related U.S. Application Data

(63) Continuation of application No. 17/614,481, filed as application No. PCT/JP2020/021345 on May 29, 2020.

(30) Foreign Application Priority Data

May 31, 2019   (JP) .................................. 2019-103212

(51) Int. Cl.
*H01L 51/50*    (2006.01)
*H10K 85/60*    (2023.01)
(Continued)

(52) U.S. Cl.
CPC ......... *H10K 85/636* (2023.02); *C07D 307/91* (2013.01); *C07D 409/14* (2013.01);
(Continued)

(58) Field of Classification Search
CPC .. H01L 51/0061; C07D 307/91; C07D 409/14
See application file for complete search history.

(56) References Cited

U.S. PATENT DOCUMENTS

| 10,249,832 B1 | 4/2019 | Takahashi et al. |
| 10,593,889 B1 | 3/2020 | Takahashi et al. |

(Continued)

FOREIGN PATENT DOCUMENTS

| CN | 108346756 A | 7/2018 |
| CN | 108864062 A | 11/2018 |

(Continued)

OTHER PUBLICATIONS

International Search Report dated Aug. 11, 2020 in PCT/JP2020/021345 filed May 29, 2020, 3 pages.

*Primary Examiner* — Anthony Ho
(74) *Attorney, Agent, or Firm* — Oblon, McClelland, Maier & Neustadt, L.L.P.

(57) ABSTRACT

Provided are a compound capable of more improving the performance of organic EL devices, an organic electroluminescent device having a more improved device performance, and an electronic device including such an organic electroluminescent device; precisely, a compound represented by the following formula (1) wherein $X^1$, $X^2$, $X^3$, L, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the description, an organic electroluminescent device containing the compound, and an electronic device including such an organic electroluminescent device.

29 Claims, 1 Drawing Sheet

(51) Int. Cl.
  *C07D 307/91* (2006.01)
  *C07D 409/14* (2006.01)
  *C09K 11/06* (2006.01)
  *H10K 50/15* (2023.01)

(52) U.S. Cl.
  CPC .......... *C09K 11/06* (2013.01); *C07B 2200/05* (2013.01); *C09K 2211/1018* (2013.01); *H10K 50/156* (2023.02); *H10K 85/6574* (2023.02); *H10K 85/6576* (2023.02)

(56) References Cited

U.S. PATENT DOCUMENTS

| | | |
|---|---|---|
| 10,658,595 B2 | 5/2020 | Yoon et al. |
| 10,680,181 B2 | 6/2020 | Takahashi et al. |
| 10,689,568 B2 | 6/2020 | Matsuura et al. |
| 2007/0278938 A1 | 12/2007 | Yabunouchi et al. |
| 2008/0191614 A1 | 8/2008 | Kim et al. |
| 2012/0181521 A1 | 7/2012 | Yabunouchi et al. |
| 2014/0159006 A1 | 6/2014 | Yabunouchi et al. |
| 2015/0287931 A1 | 10/2015 | Kato et al. |
| 2015/0372239 A1 | 12/2015 | Yabunouchi et al. |
| 2016/0049591 A1 | 2/2016 | Yabunouchi et al. |
| 2016/0351821 A1 | 12/2016 | Yabunouchi et al. |
| 2017/0294588 A1 | 10/2017 | Yabunouchi et al. |
| 2019/0039996 A1 | 2/2019 | Takada et al. |
| 2019/0044085 A1 | 2/2019 | Jeong et al. |
| 2019/0081245 A1 | 3/2019 | Yabunouchi et al. |
| 2019/0088879 A1 | 3/2019 | Haketa et al. |
| 2019/0109284 A1 | 4/2019 | Xia |
| 2019/0148640 A1 | 5/2019 | Lim et al. |
| 2019/0181344 A1 | 6/2019 | Herron et al. |
| 2019/0189946 A1 | 6/2019 | Kim et al. |
| 2019/0194215 A1 | 6/2019 | Takahashi et al. |
| 2019/0214579 A1 | 7/2019 | Seda et al. |
| 2019/0221747 A1 | 7/2019 | Takahashi et al. |
| 2019/0273220 A1 | 9/2019 | Kim et al. |
| 2019/0288220 A1 | 9/2019 | Kim et al. |
| 2019/0326516 A1 | 10/2019 | Kim et al. |
| 2019/0037201 A1 | 12/2019 | Lin et al. |
| 2019/0393421 A1 | 12/2019 | Yabunouchi et al. |
| 2019/0393429 A1 | 12/2019 | Takahashi et al. |
| 2020/0052212 A1 | 2/2020 | Tasaki et al. |
| 2020/0091435 A1 | 3/2020 | Masuda et al. |
| 2020/0111962 A1 | 4/2020 | Nakano et al. |
| 2020/0111975 A1 | 4/2020 | Ogita et al. |
| 2020/0111986 A1 | 4/2020 | Kim et al. |
| 2020/0144504 A1 | 5/2020 | Ishisone et al. |
| 2020/0203619 A1 | 6/2020 | Park et al. |
| 2020/0259086 A1 | 8/2020 | Kim et al. |
| 2020/0287152 A1 | 9/2020 | Kim et al. |
| 2020/0290985 A1 | 9/2020 | Kudo et al. |
| 2020/0317653 A1 | 10/2020 | Ito et al. |
| 2021/0005825 A1 | 1/2021 | Tasaki et al. |
| 2021/0005826 A1 | 1/2021 | Tasaki et al. |
| 2021/0013439 A1 | 1/2021 | Sado et al. |
| 2021/0028365 A1 | 1/2021 | Tasaki et al. |
| 2021/0062078 A1 | 3/2021 | Kato |
| 2021/0066599 A1 | 3/2021 | Nakano et al. |
| 2021/0066611 A1 | 3/2021 | Ito et al. |
| 2021/0094937 A1 | 4/2021 | Ito et al. |
| 2021/0098706 A1 | 4/2021 | Mun et al. |
| 2021/0253546 A1 | 8/2021 | Ito et al. |
| 2021/0296589 A1 | 9/2021 | Song et al. |
| 2021/0305513 A1 | 9/2021 | Yoon et al. |

FOREIGN PATENT DOCUMENTS

| | | |
|---|---|---|
| CN | 109096124 A | 12/2018 |
| CN | 109096175 A | 12/2018 |
| CN | 110790754 A | 2/2020 |
| EP | 3 524 607 A1 | 8/2019 |
| EP | 3 832 745 A1 | 6/2021 |
| JP | 2008-540517 A | 11/2008 |
| JP | 2012-49518 A | 3/2012 |
| JP | 2013-538793 A | 10/2013 |
| JP | 2014-9196 A | 1/2014 |
| JP | 2019-16675 A | 1/2019 |
| JP | 2019-119680 A | 7/2019 |
| KR | 10-2015-0006374 | 1/2015 |
| KR | 10-2018-0112962 A | 10/2018 |
| KR | 10-2018-0137315 A | 12/2018 |
| KR | 10-2018-0138333 A | 12/2018 |
| KR | 10-2019-0005522 A | 1/2019 |
| KR | 10-2019-0020514 A | 3/2019 |
| KR | 10-2019-0039905 A | 4/2019 |
| KR | 10-2019-0053809 A | 5/2019 |
| KR | 10-2019-0057229 A | 5/2019 |
| KR | 10-2020-0062616 A | 6/2020 |
| WO | WO 2007/125714 A1 | 11/2007 |
| WO | WO 2018/164265 A1 | 9/2018 |
| WO | WO 2018/174293 A1 | 9/2018 |
| WO | WO 2018/186374 A1 | 10/2018 |
| WO | WO 2018/186396 A1 | 10/2018 |
| WO | WO 2018/186404 A1 | 10/2018 |
| WO | WO 2019/066250 A1 | 4/2019 |
| WO | WO 2019/088231 A1 | 5/2019 |
| WO | WO 2019/117137 A1 | 6/2019 |
| WO | WO 2019/124902 A1 | 6/2019 |
| WO | WO 2019/132028 A1 | 7/2019 |
| WO | WO 2019/132040 A1 | 7/2019 |
| WO | WO 2019/146781 A1 | 8/2019 |
| WO | WO 2019/155363 A1 | 8/2019 |
| WO | WO 2019/189033 A1 | 10/2019 |
| WO | WO 2019/194298 A1 | 10/2019 |
| WO | WO 2019/198699 A1 | 10/2019 |
| WO | WO 2019/206291 A1 | 10/2019 |
| WO | WO 2019/206292 A1 | 10/2019 |
| WO | WO 2019/216411 A1 | 11/2019 |
| WO | WO 2020/036463 A1 | 2/2020 |
| WO | WO 2020/065471 A1 | 4/2020 |
| WO | WO 2020/071479 A1 | 4/2020 |
| WO | WO 2020/075758 A1 | 4/2020 |
| WO | WO 2020/075759 A1 | 4/2020 |
| WO | WO 2020/075760 A1 | 4/2020 |
| WO | WO 2020/080416 A1 | 4/2020 |
| WO | WO 2020/080417 A1 | 4/2020 |
| WO | WO 2020/095998 A1 | 5/2020 |
| WO | WO 2020/096012 A1 | 5/2020 |
| WO | WO 2020/096021 A1 | 5/2020 |
| WO | WO 2020/111253 A1 | 6/2020 |
| WO | WO 2020/115933 A1 | 6/2020 |
| WO | WO 2020/116561 A1 | 6/2020 |
| WO | WO 2020/116562 A1 | 6/2020 |
| WO | WO 2020/120791 A1 | 6/2020 |
| WO | WO 2020/120793 A1 | 6/2020 |
| WO | WO 2020/130394 A1 | 6/2020 |
| WO | WO 2020/138872 A1 | 7/2020 |
| WO | WO 2020/138875 A1 | 7/2020 |
| WO | WO 2020/152547 A1 | 7/2020 |
| WO | WO 2020/161180 A1 | 8/2020 |
| WO | WO 2020/166874 A1 | 8/2020 |
| WO | WO 2020/175948 A1 | 9/2020 |

COMPOUND, MATERIAL FOR ORGANIC ELECTROLUMINESCENT ELEMENTS, ORGANIC ELECTROLUMINESCENT ELEMENT, AND ELECTRONIC DEVICE

CROSS-REFERENCE TO RELATED APPLICATIONS

The present application is a continuation of U.S. patent application Ser. No. 17/614,481, filed on Nov. 26, 2021, which is a national stage of International Application No. PCT/JP2020/021345, filed on May 29, 2020, and claims priority to Japanese Application No. 2019-103212, filed on May 31, 2019, the disclosures of all of which are incorporated herein by reference in their entireties.

TECHNICAL FIELD

The present invention relates to a compound, a material for organic electroluminescent devices, an organic electroluminescent device, and an electronic device containing the organic electroluminescent device.

BACKGROUND ART

An organic electroluminescent device (hereinafter may be expressed as "organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, energy is released as light. Therefore, it is important for obtaining an organic EL device with a high efficiency to develop a compound that transports electrons or holes into the light emitting region efficiently and facilitates the recombination of electrons and holes.

PTL 1 describes a monoamine compound having three 4-(4-dibenzofuranyl)phenyl groups on the central nitrogen atom, and a monoamine compound having three 4-(4-dibenzothiophenyl)phenyl groups on the central nitrogen atom. These compounds are described to be used as a hole transporting material, but the performance of organic EL devices containing such a monoamine compound is not measured.

PTL 2 describes a monoamine compound having two 4-(1-dibenzothiophenyl)phenyl groups and one 4-(4-dibenzofuranyl)phenyl group on the central nitrogen atom, and a monoamine compound having two 4-(1-dibenzofuranyl)phenyl groups and one selected from a 2-dibenzothiophenyl group, a 2-dibenzofuranyl group, a 3-(4-dibenzothiophenyl)phenyl group and a 3-(4-dibenzofuranyl)phenyl group on the central nitrogen atom. However, the performance of organic EL devices containing such a monoamine compound is not measured.

In Experimental Example 1 in PTL 2, the performance of an organic EL device containing two (4-(1-dibenzothiophenyl)phenyl groups and one 4-(4-dibenzothiophenyl)phenyl group on the central nitrogen atom is measured.

PTL 3 describes a monoamine compound having three 3-(1-dibenzofuranyl)phenyl group on the central nitrogen atom is described. In Example 5, the compound is used in a hole transporting layer of an organic EL device.

CITATION LIST

Patent Literature

PTL 1: WO2007/125714
PTL 2: KR 10-2018-0138333A
PTL 3: JP 2012-049518A

SUMMARY OF INVENTION

Technical Problem

Heretofore, various compounds for organic EL devices have been reported. However, compounds that further improve the performance of organic EL devices have been still demanded.

The present invention has been made to solve the above problems and an object of the invention is to provide a compound further improving the performance of organic EL devices, an organic EL device having their performance further improved, and an electronic device containing such an organic EL device.

Solution to Problem

The present inventors have repeatedly made assiduous studies relating to organic EL devices containing the compounds described in PTLs 1 to 3 and, as a result, have found that a monoamine compound having a 1-dibenzofuranyl structure; a 1-dibenzofuranyl structure or a 1-dibenzothiophenyl structure; and a dibenzofuranyl structure or a dibenzothiophenyl structure each bonding to a central nitrogen atom via a p-phenylene group can provide an organic EL device having a high efficiency.

In one aspect, the present invention provides a compound represented by the following formula (1) (hereinunder this may be simply referred to as "the compound of the present invention").

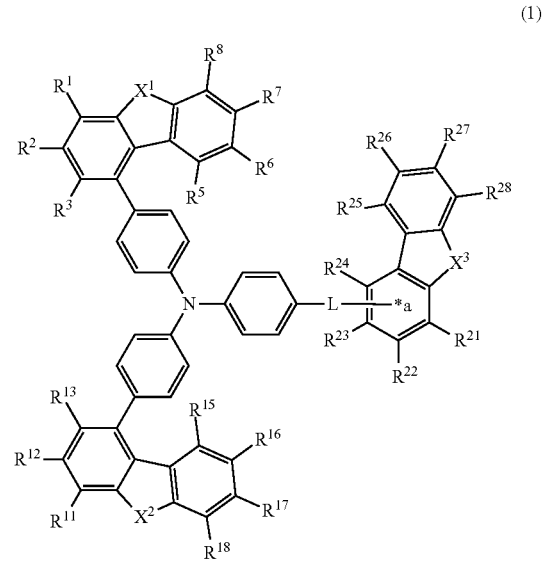

(1)

wherein:
one of $X^1$ and $X^2$ is an oxygen atom, and the other is an oxygen atom or a sulfur atom, $X^3$ is selected from an oxygen atom or a sulfur atom, L is selected from a single bond, a substituted or unsubstituted phenylene group, and a substituted or unsubstituted naphthylene group, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by $—Si(R^{901})(R^{902})(R^{903})$, a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, in one or more pairs each formed of neighboring 2 or more selected from $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$, the neighboring two bond to each other to form a substituted or unsubstituted ring, or do not bond to each other, provided that one of $R^{21}$ to $R^{24}$ is a single bond bonding to L via *a, $R^{901}$, $R^{902}$, and $R^{903}$ each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms.

In another aspect, the present invention provides a material for organic EL devices containing the compound represented by the formula (1) of the present invention.

In still another aspect, the present invention provides an organic electroluminescent device including an anode, a cathode, and an organic layer arranged between the anode and the cathode, wherein the organic layer includes a light emitting layer, and at least one layer of the organic layer contains the compound of the present invention.

In still another aspect, the present invention provides an electronic device including the above-mentioned organic electroluminescent device.

Advantageous Effects of Invention

An organic EL device containing the compound of the present invention has a high efficiency.

DESCRIPTION OF EMBODIMENTS

Figure 1:
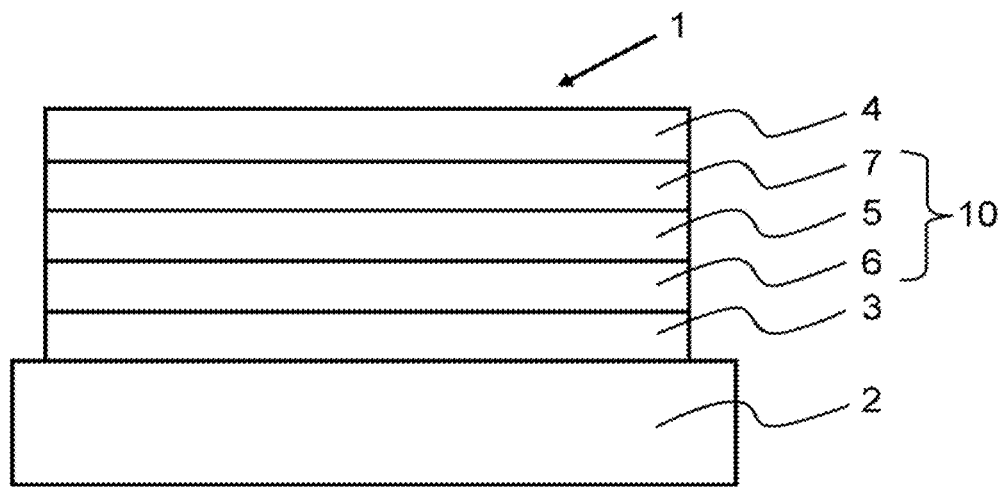
FIG. 1 is a schematic view showing one example of a layered configuration of an organic EL device of an embodiment of the invention.

In this description, the hydrogen atom includes isotopes different in the neutron numbers, i.e., light hydrogen (protium), heavy hydrogen (deuterium), and tritiated hydrogen (tritium).

In this description, the number of ring carbon atoms means the number of the carbon atoms included in the atoms that form the ring itself of a compound in which a series of atoms are bonded to form a cyclic compound (a cyclic compound, e.g., a monocyclic compound, a condensed ring compound, a crosslinked compound, a carbocyclic compound, and a heterocyclic compound) or the number of the carbon atoms constituting the ring itself of the compound (the carbon atoms are referred to as ring carbon atoms). In the case where the ring has a substituent, the carbon atom in the substituent is not included in the ring carbon atom. Unless otherwise noted, the same applies to the "number of ring carbon atoms" mentioned below.

For example, a benzene ring has 6 ring carbon atoms, a naphthalene ring has 10 ring carbon atoms, a pyridine ring has 5 ring carbon atoms, a furan ring has 4 ring carbon atoms. Also, for example, a 9,9-diphenylfluorenyl group has 13 ring carbon atoms, and a 9,9'-spirobifluorenyl group has 25 ring carbon atoms.

In the case where a benzene ring has, for example, an alkyl substituent, the carbon atom in the alkyl substituent is not counted as the ring carbon atom of the benzene ring. Therefore, an alkyl-substituted benzene ring has 6 ring carbon atoms. In the case where a naphthalene ring has, for example, an alkyl substituent, the carbon atom in the alkyl substituent is not counted as the ring carbon atom of the naphthalene ring. Therefore, an alkyl-substituted naphthalene ring has 10 ring carbon atoms.

In this description, the number of ring atoms means the number of the atoms constituting the ring of the above-mentioned cyclic compound or the condensed ring compound (the atoms are referred to as ring atoms). The hydrogen atom bonding to the ring atom and the atom included in the substituent bonding to the ring atom are not included in the number of ring atoms. Unless otherwise noted, the same applies to the "number of ring atoms" mentioned below.

For example, a pyridine ring has 6 ring atoms, a quinazoline ring has 10 ring atoms, and a furan ring has 5 ring atoms. For example, the number of the hydrogen atoms bonding to a pyridine ring, or the atoms constituting a substituent is not counted as the ring atom of a pyridine ring. Therefore, the number of the ring atoms of a pyridine ring to which a hydrogen atom or a substituent bonds is 6. Also, for example, the number of the hydrogen atoms bonding to a quinazoline ring, or the atoms constituting a substituent is not counted as the ring atom of a quinazoline ring. Therefore, the number of the ring atoms of a quinazoline ring in which a hydrogen atom or a substituent bonds to the ring atom is 10.

In this description, the expression of "XX to YY carbon atoms" in a "substituted or unsubstituted group ZZ having XX to YY carbon atoms" is the number of carbon atoms of the unsubstituted group ZZ and does not include any carbon atom in the substituent of the substituted group ZZ.

In this description, the expression of "XX to YY atoms" in a "substituted or unsubstituted group ZZ having XX to YY atoms" is the number of atoms of the unsubstituted group ZZ and does not include any atom in the substituent of the substituted group ZZ.

In this description, an unsubstituted ZZ group represents a case where "a substituted or unsubstituted ZZ group" is "an unsubstituted ZZ group", and a substituted ZZ group represents a case where "a substituted or unsubstituted ZZ group" is "a substituted ZZ group".

In this description, "unsubstituted" in a case of "a substituted or unsubstituted ZZ group" means that the hydrogen atom in the ZZ group is not substituted with a substituent.

Also in this description, "substituted" in a case of "a substituted or unsubstituted ZZ group" means that one or more hydrogen atoms in the ZZ group are substituted with substituent(s). The same applies to a case of "a BB group substituted with an AA group", that is, this means that one or more hydrogen atoms in the BB group are substituted with AA group(s).

Substituents Referred to this Description

The substituents referred to this description are explained below. Unless otherwise noted, the substituents have the following definitions.

(1) Substituted or Unsubstituted Aryl Group

The number of ring carbon atoms of "an unsubstituted aryl group" of "a substituted or unsubstituted aryl group" referred to in this description is, unless otherwise noted, 6 to 50, preferably 6 to 30, more preferably 6 to 18.

Specific examples (group G1 of specific examples) of the above-mentioned "substituted or unsubstituted aryl group" include the following unsubstituted aryl groups (Group G1A of specific examples) and substituted aryl groups (Group G1B of specific examples). Examples of the "substituted aryl group" include groups of the "unsubstituted aryl group" of the following Group G1A of specific examples in which one or more hydrogen atoms are substituted with substituent(s), and examples of substituted aryl groups of the following Group G1B of specific examples. Examples of the "unsubstituted aryl group" and examples of the "substituted aryl group" listed herein are some mere examples, and the "substituted aryl group" referred to in this description further includes groups of the "substituted aryl group" of the following Group G1B of specific examples in which the hydrogen atom bonding to the ring carbon atom of the aryl group itself is further substituted with a substituent, and groups of the "substituted aryl group" of the following Group G1B of specific examples in which the hydrogen atom of the substituent of the "substituted aryl group" is further substituted with a substituent.

Group G1A of Specific Examples: Unsubstituted Aryl Groups a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived from a cyclic structure represented by the following general formulae (TEMP-1) to (TEMP-15), by removing one hydrogen atom from the cyclic structure.

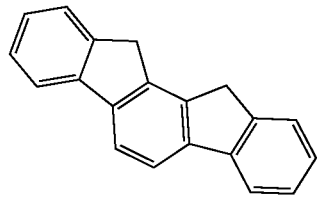

(TEMP-1)

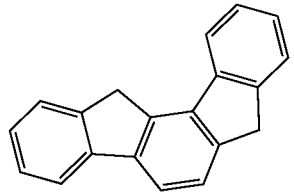

(TEMP-2)

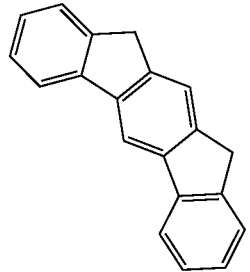

(TEMP-3)

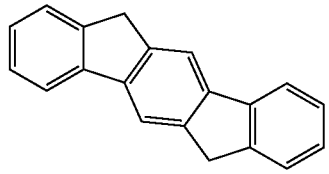

(TEMP-4)

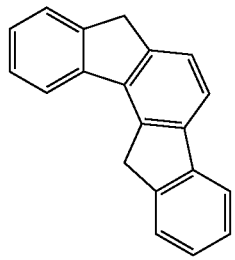

(TEMP-5)

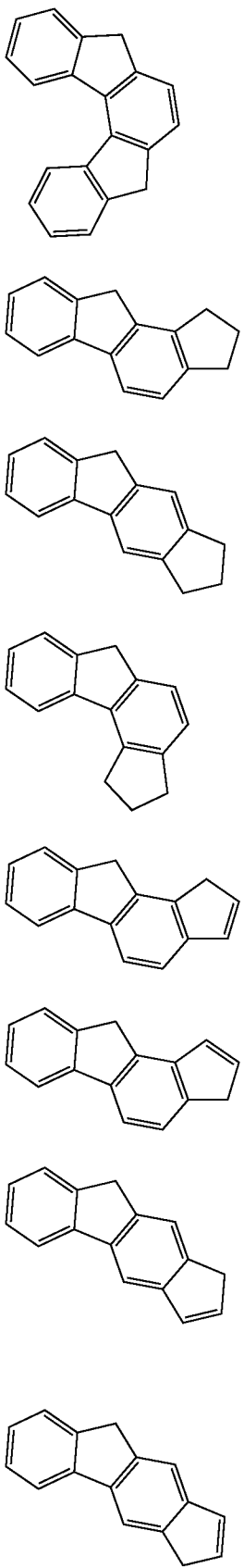

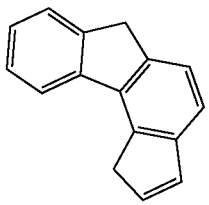

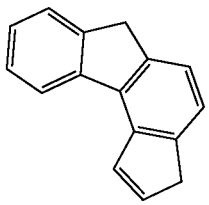

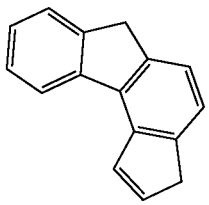

Group G1B of Specific Examples: Substituted Aryl Groups
an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
a group of the monovalent group derived from the cyclic structure represented by the general formulae (TEMP-1) to (TEMP-15) in which one or more hydrogen atoms are substituted with substituent(s).

Unless otherwise noted, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, and a 9,9-diphenylfluorenyl group.

(2) Substituted or Unsubstituted Heterocyclic Group

The number of the ring atoms of the "unsubstituted heterocyclic group" of the "substituted or unsubstituted heterocyclic group" referred to in this description is, unless otherwise noted, 5 to 50, preferably 5 to 30, more preferably 5 to 18.

The "heterocyclic group" is a cyclic group containing at least one hetero atom as the ring atom. Specific examples of the ring hetero atom include a nitrogen atom, an oxygen atom, a sulfur atom, a silicon atom, a phosphorus atom, and a boron atom.

The "heterocyclic group" is a monocyclic group, or a condensed cyclic group.

The "heterocyclic group" is an aromatic heterocyclic group or a nonaromatic heterocyclic group.

Specific examples (Group G2 of specific examples) of the "substituted or unsubstituted heterocyclic group" include the following unsubstituted heterocyclic groups (Group G2A of specific examples), and the following substituted heterocyclic groups (Group G2B of specific examples).

Specific examples of the "substituted heterocyclic group" include groups of the "unsubstituted heterocyclic group" of the following Group G2A of specific examples in which one ore more hydrogen atoms are substituted, and examples of the substituted heterocyclic group of the following Group G2B of specific examples. Examples of the "unsubstituted heterocyclic group" and examples of the "substituted heterocyclic group" listed herein are some mere examples, and the "substituted heterocyclic group" referred to in this description further includes groups of the "substituted heterocyclic group" of the following Group G2B of specific examples in which the hydrogen atom bonding to the ring atom of the heterocyclic group itself is further substituted with a substituent, and groups of the "substituted heterocyclic group" of the following Group G2B of specific examples in which the hydrogen atom of the substituent of the heterocyclic group is further substituted with a substituent.

Examples of Group G2A of specific examples include the following nitrogen atom-containing, unsubstituted heterocyclic groups (Group G2A1 of specific examples), the following oxygen atom-containing, unsubstituted heterocyclic groups (Group G2A2 of specific examples), the following sulfur atom-containing, unsubstituted heterocyclic groups (Group G2A3 of specific examples), and monovalent heterocyclic groups derived from cyclic structures represented by the following general formulae (TEMP-16) to (TEMP-33) by removing one hydrogen atom from each cyclic structure (Group G2A4 of specific examples).

Examples of Group G2B of specific examples include the following nitrogen atom-containing, substituted heterocyclic groups (Group G2B1 of specific examples), the following oxygen atom-containing, substituted heterocyclic groups (Group G2B2 of specific examples), the following sulfur atom-containing, substituted heterocyclic groups (Group G2B3 of specific examples), and monovalent heterocyclic groups derived from cyclic structures represented by the following general formulae (TEMP-16) to (TEMP-33) by substituting one or more hydrogen atoms with substituent(s) (Group G2B4 of specific examples).

Group G2A1 of Specific Examples: Nitrogen Atom-Containing, Unsubstituted Heterocyclic Groups
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolidinyl group,
a quinolidinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Group G2A2 of Specific Examples: Oxygen Atom-Containing, Unsubstituted Heterocyclic Groups
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Group G2A3 of Specific Examples: Sulfur Atom-Containing, Unsubstituted Heterocyclic Groups
a thienyl group,
a thiazolyl group,
an isothiazolyl group,
a thiadiazolyl group,
a benzothiophenyl group (a benzothienyl group),
an isobenzothiophenyl group (an isobenzothienyl group),
a dibenzothiophenyl group (a dibenzothienyl group),
a naphthobenzothiophenyl group (a naphthobenzothienyl group),
a benzothiazolyl group,
a benzisothiazolyl group,
a phenothiazinyl group,
a dinaphthothiophenyl group (a dinaphthothienyl group),
an azadibenzothiophenyl group (an azadibenzothienyl group),
a diazadibenzothiophenyl group (a diazadibenzothienyl group), an azanaphthobenzothiophenyl group (an azanaphthobenzothienyl group), and a diazanaphthobenzothiophenyl group (a diazanaphthobenzothienyl group).

Group G2A4 of Specific Examples: Monovalent Heterocyclic Groups Derived from Cyclic Structures Represented by the Following General Formulae (TEMP-16) to (TEMP-33)

(TEMP-16)
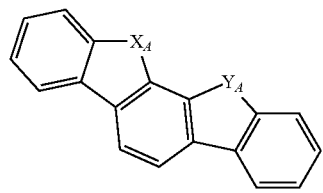

(TEMP-17)
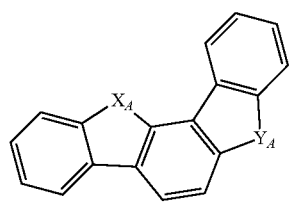

(TEMP-18)
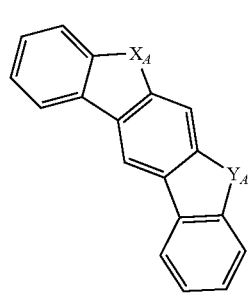

(TEMP-19)
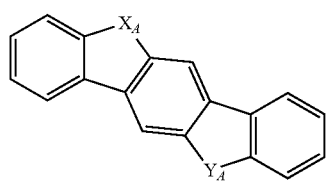

(TEMP-20)
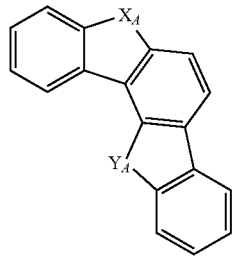

(TEMP-21)
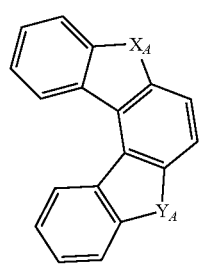

(TEMP-22)
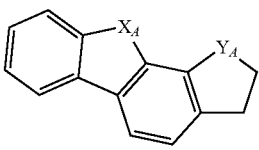

(TEMP-23)
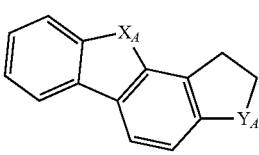

(TEMP-24)
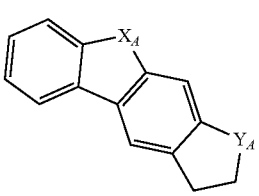

(TEMP-25)
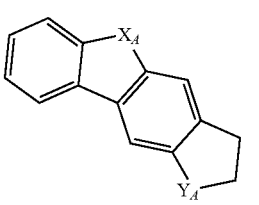

(TEMP-26)
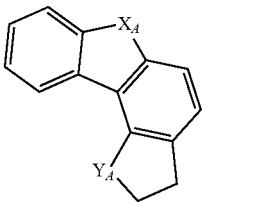

(TEMP-27)
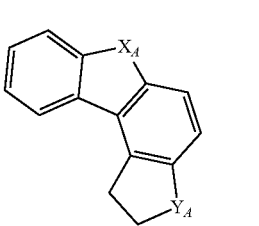

(TEMP-28)
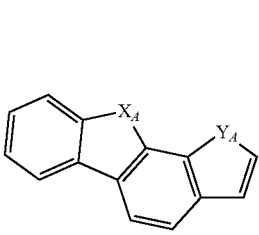

(TEMP-29)
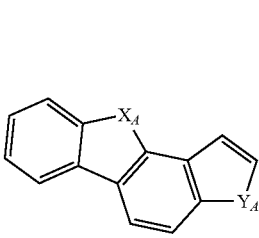

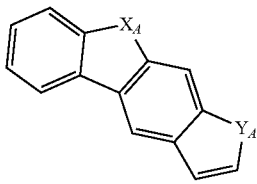
(TEMP-30)

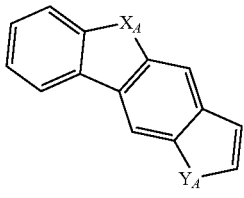
(TEMP-31)

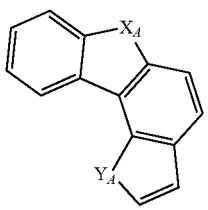
(TEMP-32)

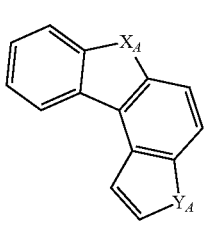
(TEMP-33)

In the above general formulae (TEMP-16) to (TEMP-33), $X_A$ and $Y_A$ each independently represent an oxygen atom, a sulfur atom, NH or $CH_2$, provided that at least one of $X_A$ and $Y_A$ is an oxygen atom, a sulfur atom or NH.

In the case where at least any of $X_A$ and $Y_A$ is NH in the above general formulae (TEMP-16) to (TEMP-33), or one of $X_A$ and $Y_A$ is $CH_2$, the monovalent heterocyclic groups derived from the cyclic structures represented by the general formulae (TEMP-16) to (TEMP-33) include monovalent groups derived from these by removing one hydrogen atom from NH or $CH_2$.

Group G2B1 of Specific Examples: Nitrogen Atom-Containing, Substituted Heterocyclic Groups
a (9-phenyl)carbazolyl group,
a (9-biphenylyl)carbazolyl group,
a (9-phenyl)phenylcarbazolyl group,
a (9-naphthyl)carbazolyl group,
a diphenylcarbazole-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Group G2B2 of Specific Examples: Oxygen Atom-Containing, Substituted Heterocyclic Groups
a phenyldibenzofuranyl group,
a methyklibenzofuranyl group,
a t-butyldibenzofuranyl group, and
a monovalent residue of spiro[9H-xanthene-9,9'-[9H]fluorene].

Group G2B3 of Specific Examples: Sulfur Atom-Containing, Substituted Heterocyclic Groups
a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Group G2B4 of Specific Examples: Monovalent Heterocyclic Groups Derived from Cyclic Structures Represented by the Above-Mentioned General Formulae (TEMP-16) to (TEMP-33) by Substituting One or More Hydrogen Atoms with Substituent(s)

The above-mentioned "one or more hydrogen atoms of a monovalent heterocyclic group" mean one or more hydrogen atoms selected from a hydrogen atom bonding to the ring carbon atom of the monovalent heterocyclic group, a hydrogen atom bonding to the nitrogen atom in the case where at least any of $X_A$ and $Y_A$ is NH, and a hydrogen atom of a methylene group in the case where one of $X_A$ and $Y_A$ is $CH_2$.

Unless otherwise noted, preferred examples of the substituted or unsubstituted heterocyclic group include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a 9-phenylcarbazolyl group (a 9-phenylcarbazol-1-yl group, a 9-phenylcarbazol-2-yl group, a 9-phenylcarbazol-3-yl group, or a 9-phenylcarbazol-4-yl group), a 9-biphenylylcarbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, and a phenyldibenzothiophenyl group.

In this description, the carbazolyl group is, unless otherwise noted, a group of any of the following:

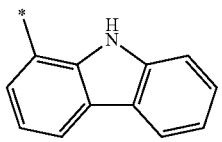
(TEMP-Cz1)

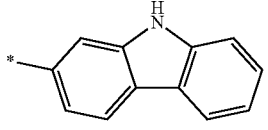
(TEMP-Cz2)

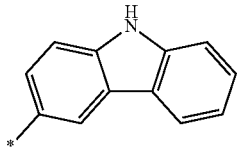
(TEMP-Cz3)

(TEMP-Cz4)
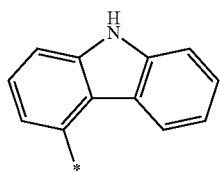

(TEMP-Cz5)
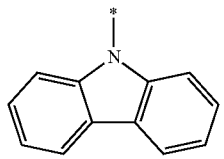

In these formulae, * indicates a bonding position.

In this description, the 9-phenylcarbazolyl group is, unless otherwise noted, a group of any of the following:

(TEMP-Cz6)
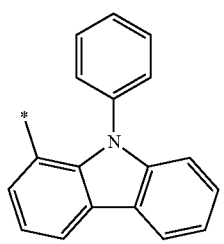

(TEMP-Cz7)
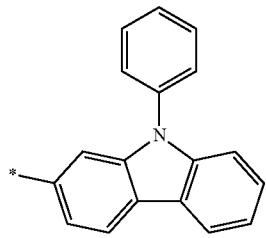

(TEMP-Cz8)
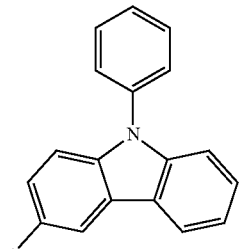

(TEMP-Cz9)
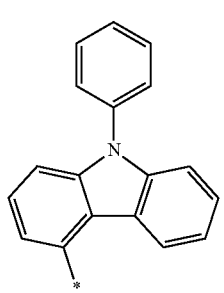

In these formulae, * indicates a bonding position.

In this description, the dibenzofuranyl group and the dibenzothiophenyl group are, unless otherwise noted, groups of any of the following:

(TEMP-34)
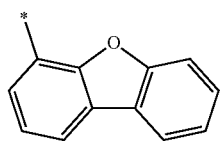

(TEMP-35)
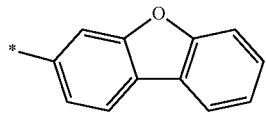

(TEMP-36)
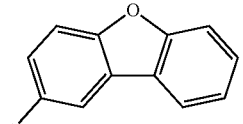

(TEMP-37)
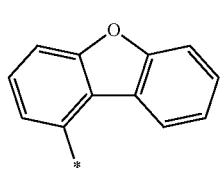

(TEMP-38)
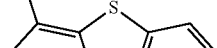

(TEMP-39)
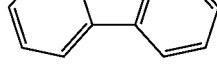

(TEMP-40)
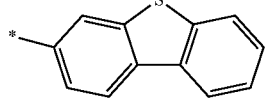

(TEMP-41)
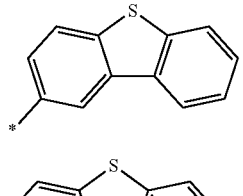

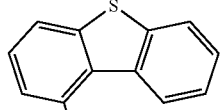

In these formulae, * indicates a bonding position.

(3) Substituted or Unsubstituted Alkyl Group

The carbon number of the "unsubstituted alkyl group" of the "substituted or unsubstituted alkyl group" referred to in this description is, unless otherwise noted, 1 to 50, preferably 1 to 20, more preferably 1 to 6.

Specific examples of the "substituted or unsubstituted alkyl group" (Group G3 of specific examples) include the following unsubstituted alkyl groups (Group G3A of specific examples) and the following substituted alkyl groups (Group G3B of specific examples).

Specific examples of the "substituted alkyl group" include groups of the following "unsubstituted alkyl group" (Group G3A of specific examples) in which one or more hydrogen atoms are substituted, and examples of the substituted alkyl group (Group G3B of specific examples).

In this description, the alkyl group in the "unsubstituted alkyl group" means a chainlike alkyl group, and includes a linear alkyl group and a branched alkyl group. Examples of the "unsubstituted alkyl group" and examples of the "substituted alkyl group" listed herein are some mere examples, and the "substituted alkyl group" further includes groups of the "substituted alkyl group" of Group G3B of specific examples in which the hydrogen atom of the alkyl group itself is further substituted with a substituent, and groups of the "substituted alkyl group" of Group G3B of specific examples in which the hydrogen atom of the substituent of the alkyl group is further substituted with a substituent.

Group G3A of Specific Examples: Unsubstituted Alkyl Groups
a methyl group,
an ethyl group,
an n-propyl group,
an isopropyl group,
an n-butyl group,
an isobutyl group,
an s-butyl group, and
a t-butyl group.

Group G3B of Specific Examples: Substituted Alkyl Groups
a heptafluoropropyl group (including isomers),
a pentafluoroethyl group,
a 2,2,2-trifluoroethyl group, and
a trifluoromethyl group.

Unless otherwise noted, the substituted or unsubstituted alkyl group is preferably a methyl group, an ethyl group, a propyl group, an isopropyl group, an n-butyl group, an isobutyl group or a t-butyl group.

(4) Substituted or Unsubstituted Alkenyl Group

Unless otherwise noted, the carbon number of the "unsubstituted alkenyl group" of the "substituted or unsubstituted alkenyl group" referred to in this description is 2 to 50, preferably 2 to 20, more preferably 2 to 6.

Specific examples of the "substituted or unsubstituted alkenyl group" (Group G4 of specific examples) include the following unsubstituted alkenyl groups (Group G4A of specific examples) and the following substituted alkenyl groups (Group G4B of specific examples).

Specific examples of the "substituted alkenyl group" include groups of the following "unsubstituted alkenyl group" (Group G4A of specific examples) in which one or more hydrogen atoms are substituted, and examples of the substituted alkenyl group (Group G4B of specific examples). Examples of the "unsubstituted alkenyl group" and examples of the "substituted alkenyl group" listed herein are some mere examples, and the "substituted alkenyl group" referred to in this description further includes groups of the "substituted alkenyl group" of Group G4B of specific examples in which the hydrogen atom of the alkenyl group itself is further substituted with a substituent, and groups of the "substituted alkenyl group" of Group G4B of specific examples in which the hydrogen atom of the substituent of the alkenyl group is further substituted with a substituent.

Group G4A of Specific Examples: Unsubstituted Alkenyl Groups
a vinyl group,
an allyl group,
a 1-butenyl group,
a 2-butenyl group, and
a 3-butenyl group.

Group G4B of Specific Examples: Substituted Alkenyl Groups
a 1,3-butanedienyl group,
a 1-methylvinyl group,
a 1-methylallyl group,
a 1,1-dimethylallyl group,
a 2-methylallyl group, and
a 1,2-dimethylallyl group.

(5) Substituted or Unsubstituted Alkynyl Group

Unless otherwise noted, the carbon number of the "unsubstituted alkynyl group" of the "substituted or unsubstituted alkynyl group" referred to in this description is 2 to 50, preferably 2 to 20, more preferably 2 to 6.

Specific examples of the "substituted or unsubstituted alkynyl group" (Group G5 of specific examples) include the following unsubstituted alkynyl groups (Group G5A of specific examples).

Specific examples of the "substituted alkynyl group" include groups of the following "unsubstituted alkynyl group" (Group G5A of specific examples) in which one or more hydrogen atoms are substituted.

Group G5A of Specific Examples: Unsubstituted Alkynyl Groups an ethynyl group.

(6) Substituted or Unsubstituted Cycloalkyl Group

Unless otherwise noted, the ring carbon number of the "unsubstituted cycloalkyl group" of the "substituted or unsubstituted cycloalkyl group" referred to in this description is 3 to 50, preferably 3 to 20, more preferably 3 to 6.

Specific examples of the "substituted or unsubstituted cycloalkyl group" (Group G6 of specific examples) include the following unsubstituted cycloalkyl groups (Group G6A of specific examples) and the following substituted cycloalkyl groups (Group G6B of specific examples).

Specific examples of the "substituted cycloalkyl group" include groups of the following "unsubstituted cycloalkyl group" (Group G6A of specific examples) in which one or more hydrogen atoms are substituted, and examples of the substituted cycloalkyl group (Group G6B of specific examples). Examples of the "unsubstituted cycloalkyl group" and examples of the "substituted cycloalkyl group" listed herein are some mere examples, and the "substituted cycloalkyl group" referred to in this description further includes groups of the "substituted cycloalkyl group" of Group G6B of specific examples in which one or more hydrogen atoms bonding to the ring carbon atom of the cycloalkyl group itself are further substituted with a substituent, and groups of the "substituted cycloalkyl group" of Group G6B of specific examples in which the hydrogen atom of the substituent is further substituted with a substituent.

Group G6A of Specific Examples: Unsubstituted Cycloalkyl Groups
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Group G6B of Specific Examples: Substituted Cycloalkyl Groups
a 4-methylcyclohexyl group.

(7) Group Represented by —Si($R^{901}$)($R^{902}$)($R^{903}$)

Specific examples of the group represented by —Si($R^{901}$)($R^{902}$)($R^{903}$) include substituted silyl groups of Group G7 of specific examples mentioned below.

Group G7 of Specific Examples; Substituted Silyl Groups
—Si(G1)(G1)(G1),
—Si(G1)(G2)(G2),
—Si(G1)(G1) (G2),
—Si(G2)(G2)(G2),
—Si(G3)(G3)(G3), and
—Si(G6)(G6)(G6)

In these,

G1 is a "substituted or unsubstituted aryl group" of Group G1 of specific examples.

G2 is a "substituted or unsubstituted heterocyclic group" of Group G2 of specific examples.

G3 is a "substituted or unsubstituted alkyl group" of Group G3 of specific examples.

G6 is a "substituted or unsubstituted cycloalkyl group" of Group G6 of specific examples.

Plural G1's in —Si(G1)(G1)(G1) are the same as or different from each other.

Plural G2's in —Si(G1)(G2)(G2) are the same as or different from each other.

Plural G1's in —Si(G1)(G1)(G2) are the same as or different from each other.

Plural G2's in —Si(G2)(G2)(G2) are the same as or different from each other.

Plural G3's in —Si(G3)(G3)(G3) are the same as or different from each other.

Plural G6's in —Si(G6)(G6)(G6) are the same as or different from each other.

(8) Group Represented by —O—($R^{904}$)

Specific examples of the group represented by —O—($R^{904}$) include the following groups of Group G8 of specific examples.

Group G8 of specific examples: Groups represented by —O—($R^{904}$)
—O(G1),
—O(G2),
—O(G3), and
—O(G6).

In these,

G1 is a "substituted or unsubstituted aryl group" of Group G1 of specific examples.

G2 is a "substituted or unsubstituted heterocyclic group" of Group G2 of specific examples.

G3 is a "substituted or unsubstituted alkyl group" of Group G3 of specific examples.

G6 is a "substituted or unsubstituted cycloalkyl group" of Group G6 of specific examples.

(9) Group Represented by —S—($R^{905}$)

Specific examples of the group represented by —S—($R^{905}$) include groups of the following Group G9 of specific examples.

Group G9 of Specific Examples: Group Represented by —S—($R^{905}$)
—S(G1),
—S(G2),
—S(G3), and
—S(G6).

In these,

G1 is a "substituted or unsubstituted aryl group" of Group G1 of specific examples.

G2 is a "substituted or unsubstituted heterocyclic group" of Group G2 of specific examples.

G3 is a "substituted or unsubstituted alkyl group" of Group G3 of specific examples.

G6 is a "substituted or unsubstituted cycloalkyl group" of Group G6 of specific examples.

(10) Group Represented by —N($R^{906}$)($R^{907}$)

Specific examples of the group represented by —N($R^{906}$)($R^{907}$) include substituted amino groups of Group G10 of specific examples.

Group G10 of specific examples: Group represented by —N($R^{906}$)($R^{907}$)
—N(G1)(G1),
—N(G2)(G2),
—N(G1)(G2),
—N(G3)(G3), and
—N(G6)(G6).

In these,

G1 is a "substituted or unsubstituted aryl group" of Group G1 of specific examples.

G2 is a "substituted or unsubstituted heterocyclic group" of Group G2 of specific examples.

G3 is a "substituted or unsubstituted alkyl group" of Group G3 of specific examples.

G6 is a "substituted or unsubstituted cycloalkyl group" of Group G6 of specific examples.

Plural G1's in N(G1)(G1) are the same as or different from each other.

Plural G2's in N(G2)(G2) are the same as or different from each other.

Plural G3's in N(G3)(G3) are the same as or different from each other.

Plural G6's in N(G6)(G6) are the same as or different from each other.

(11) Halogen Atom

Specific examples of "a halogen atom" referred to in this description (Group G11 of specific examples) include the following:

Group G11 of Specific Examples: Halogen Atom
a fluorine atom,
a chlorine atom,
a bromine atom, and
an iodine atom.

(12) Substituted or Unsubstituted Haloalkyl Group

The carbon number of the "unsubstituted haloalkyl group" of the "substituted or unsubstituted haloalkyl group" referred to in this description is, unless otherwise noted, 1 to 50, preferably 1 to 30, more preferably 1 to 18.

The "substituted or unsubstituted haloalkyl group" means a group of "a substituted or unsubstituted alkyl group" in which at least one hydrogen atom bonding to the carbon atom that constitutes the alkyl group is substituted with a halogen atom, and includes a group of "a substituted or unsubstituted alkyl group" in which all the hydrogen atoms bonding to the carbon atoms that constitute the alkyl group are substituted with halogen atoms.

The "substituted haloalkyl group" means a "haloalkyl group" in which one or more hydrogen atoms are substituted with substituent(s). The "substituted haloalkyl group" referred to in this description also includes a "substituted haloalkyl group" in which one or more hydrogen atoms bonding to the carbon atom of the alkyl chain therein are further substituted with substituent(s), and a "substituted haloalkyl group" in which one or more hydrogen atoms of the substituent are further substituted with a substituent.

Specific examples of the "unsubstituted haloalkyl group" include examples of the above-mentioned "alkyl group" (Group G3 of specific examples) in which one or more hydrogen atoms are substituted with halogen atom(s). A haloalkyl group may be referred to as a halogenated alkyl group.

(13) Substituted or Unsubstituted Alkoxy Group

The carbon number of the "unsubstituted alkoxy group" of the "substituted or unsubstituted alkoxy group" referred to in this description is, unless otherwise noted, 1 to 50, preferably 1 to 30, more preferably 1 to 18.

The "substituted or unsubstituted alkoxy group" is a group represented by —O(G3), and G3 is a "substituted or unsubstituted alkyl group" of Group G3 of specific examples.

(14) Substituted or Unsubstituted Alkylthio Group

The carbon number of the "unsubstituted alkylthio group" of the "substituted or unsubstituted alkylthio group" referred to in this description is, unless otherwise noted, 1 to 50, preferably 1 to 30, more preferably 1 to 18.

The "substituted or unsubstituted alkoxy group" is a group represented by —S(G3), and G3 is a "substituted or unsubstituted alkyl group" of Group G3 of specific examples.

(15) Substituted or Unsubstituted Aryloxy Group

The ring carbon number of the "unsubstituted aryloxy group" of the "substituted or unsubstituted aryloxy group" referred to in this description is, unless otherwise noted, 6 to 50, preferably 6 to 30, more preferably 6 to 18.

The "substituted or unsubstituted aryloxy group" is a group represented by —O(G1), and G1 is a "substituted or unsubstituted aryl group" of Group G1 of specific examples.

(16) Substituted or Unsubstituted Arylthio Group

The ring carbon number of the "unsubstituted arylthio group" of the "substituted or unsubstituted arylthio group" referred to in this description is, unless otherwise noted, 6 to 50, preferably 6 to 30, more preferably 6 to 18.

The "substituted or unsubstituted aryloxy group" is a group represented by —S(G1), and G1 is a "substituted or unsubstituted aryl group" of Group G1 of specific examples.

(17) Substituted or Unsubstituted Haloalkoxy Group

The carbon number of the "unsubstituted haloalkoxy group" of the "substituted or unsubstituted haloalkoxy group" referred to in this description is, unless otherwise noted, 1 to 50, preferably 1 to 30, more preferably 1 to 18.

The "substituted or unsubstituted haloalkoxy group" is a group represented by —O(G12), and G12 is a "substituted or unsubstituted haloalkyl group" of "(12) substituted or unsubstituted haloalkyl group".

(18) Substituted or Unsubstituted Aralkyl Group

The carbon number of the "unsubstituted aralkyl group" of the "substituted or unsubstituted aralkyl group" referred to in this description is, unless otherwise noted, 7 to 50, preferably 7 to 30, more preferably 7 to 18.

The "substituted or unsubstituted aralkyl group" is a group represented by -(G3)-(G1), in which G3 is a "substituted or unsubstituted alkyl group" of Group G3 of specific examples, and G1 is a "substituted or unsubstituted aryl group" of Group G1 of specific examples. Accordingly, the "aralkyl group" is a group of an "alkyl group" in which the hydrogen atom is substituted with a substituent "aryl group", and is one embodiment of a "substituted alkyl group". The "unsubstituted aralkyl group" is an "unsubstituted alkyl group" in which the hydrogen atom is substituted with an "unsubstituted aryl group".

Specific examples of the "substituted or unsubstituted aralkyl group" include a benzyl group, a 1-phenylethyl group, a 2-phenylethyl group, a 1-phenyl-isopropyl group, a 2-phenyl-isopropyl group, a phenyl-t-butyl group, an a-naphthylmethyl group, a 1-α-naphthylethyl group, a 2-α-naphthylethyl group, a 1-α-naphthyl-isopropyl group, a 2-α-naphthyl-isopropyl group, a β-naphthylmethyl group, a 1-β-naphthylethyl group, a 2-β-naphthylethyl group, a 1-β-naphthyl-isopropyl group and a 2-β-naphthyl-isopropyl group.

(19) Substituted or Unsubstituted Arylene Group

The ring carbon number of the "unsubstituted arylene group" of the "substituted or unsubstituted arylene group" referred to in this description is, unless otherwise noted, 6 to 50, preferably 6 to 30, more preferably 6 to 18.

The "substituted or unsubstituted arylene group" referred is, unless otherwise noted, a divalent group derived from the above-mentioned "substituted or unsubstituted aryl group" by removing one hydrogen atom from the aryl ring therein. Specific examples of the "substituted or unsubstituted arylene group" (Group G12 of specific examples) include a divalent group derived from the "substituted or unsubstituted aryl group" of Group G1 of specific examples by removing one hydrogen atom from the aryl ring therein.

Unless otherwise noted, the substituted or unsubstituted arylene group is preferably a group represented by any of the following formulae (TEMP-42) to (TEMP-67):

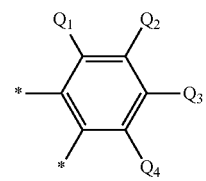
(TEMP-42)

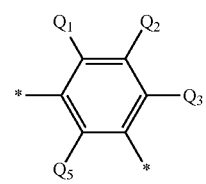
(TEMP-43)

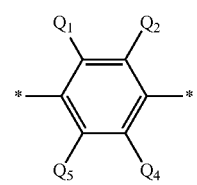
(TEMP-44)

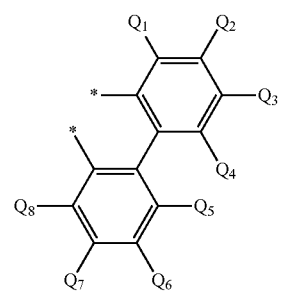
(TEMP-45)

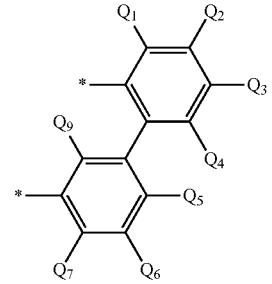
(TEMP-46)

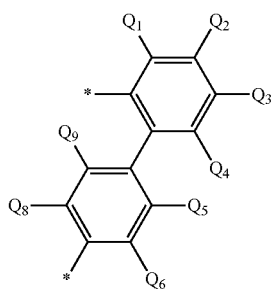
(TEMP-47)
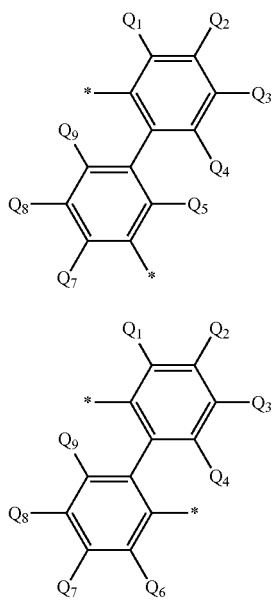
(TEMP-48)
(TEMP-49)
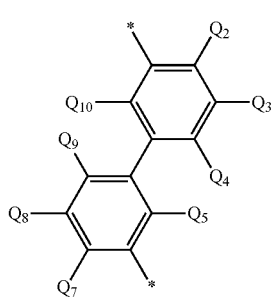
(TEMP-50)
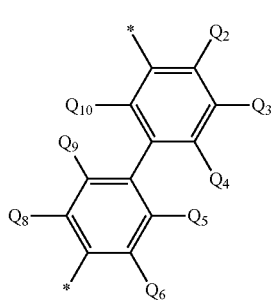
(TEMP-51)
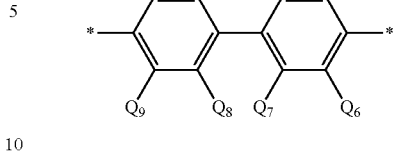
(TEMP-52)
In these formulae (TEMP-42) to (TEMP-52),
$Q_1$ to $Q_{10}$ each are independently a hydrogen atom or a substituent selected from the following "arbitrary substituents",
* indicates a bonding position.
(TEMP-53)
(TEMP-54)
(TEMP-55)
(TEMP-56)
(TEMP-57)
(TEMP-58)

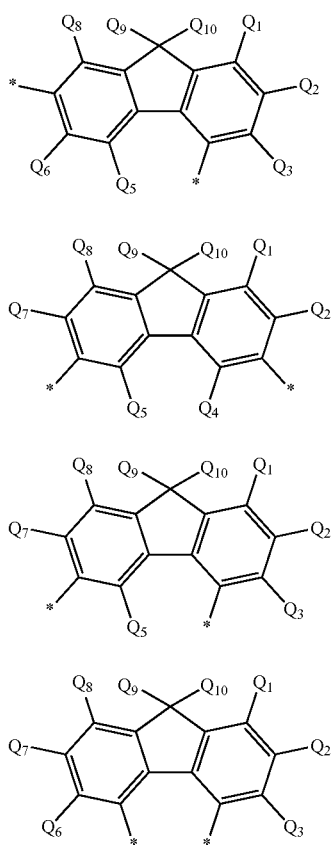

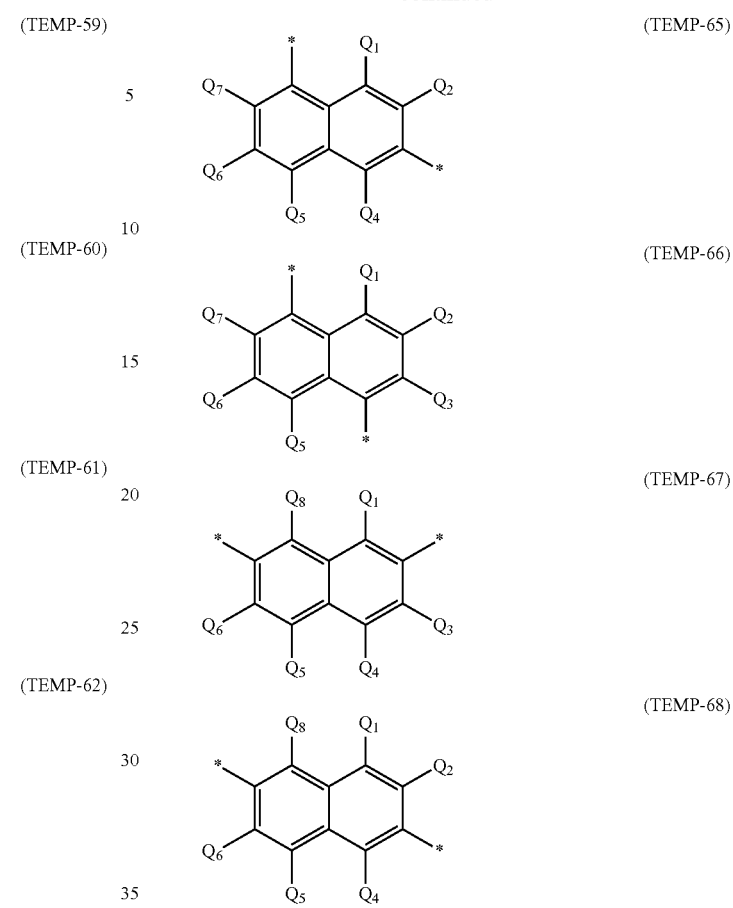

In these formulae (TEMP-53) to (TEMP-62), $Q_1$ to $Q_{10}$ each are independently a hydrogen atom or a substituent selected from the following "arbitrary substituents", $Q_9$ and $Q_{10}$ may bond to each other via a single bond to form a ring,

* indicates a bonding position.

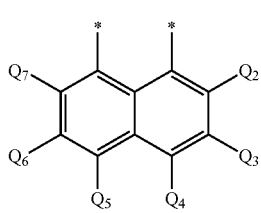

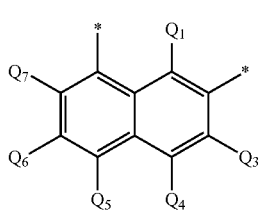

In these formulae (TEMP-63) to (TEMP-68), $Q_1$ to $Q_8$ each are independently a hydrogen atom or a substituent selected from the following "arbitrary substituents",

* indicates a bonding position.

(20) Substituted or Unsubstituted Divalent Heterocyclic Group

The ring atom number of the "unsubstituted divalent heterocyclic group" of the "substituted or unsubstituted divalent heterocyclic group" referred to in this description is, unless otherwise noted, 5 to 50, preferably 5 to 30, more preferably 5 to 18.

The "substituted or unsubstituted divalent heterocyclic group" is, unless otherwise noted, a divalent group derived from the above-mentioned "substituted or unsubstituted heterocyclic group" by removing one hydrogen atom from the hetero ring therein. Specific examples of the "substituted or unsubstituted divalent heterocyclic group" (Group G13 of specific examples) include a divalent group derived from the "substituted or unsubstituted heterocyclic group" of Group G2 of specific examples by removing one hydrogen atom from the hetero ring therein.

Unless otherwise noted, the substituted or unsubstituted divalent heterocyclic group is preferably a group represented by any of the following formulae (TEMP-69) to (TEMP-102):

(TEMP-69)
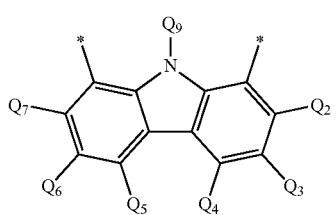
(TEMP-70)
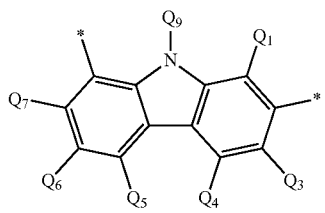
(TEMP-71)
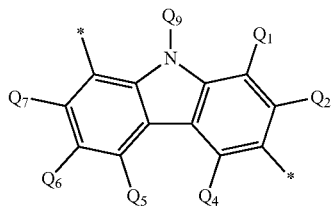
(TEMP-72)
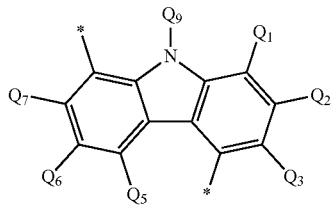
(TEMP-73)
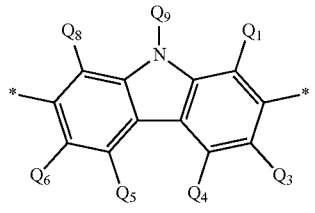
(TEMP-74)
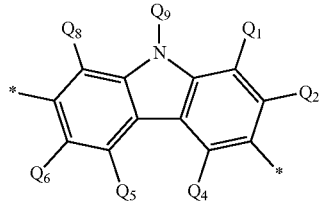
(TEMP-75)
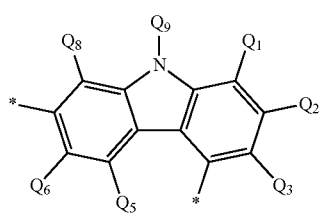
(TEMP-76)
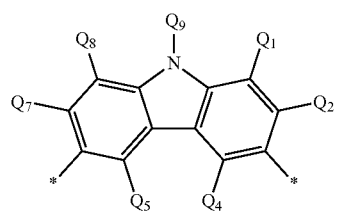
(TEMP-77)
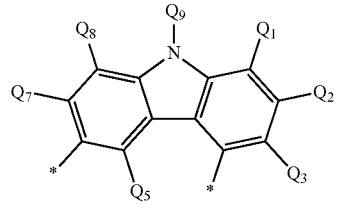
(TEMP-78)
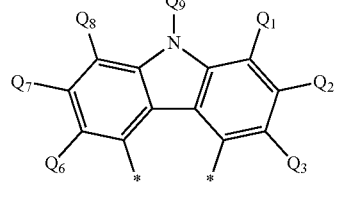
(TEMP-79)
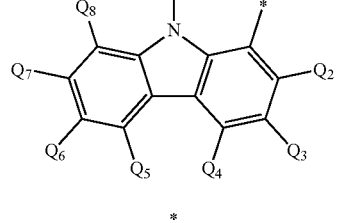
(TEMP-80)
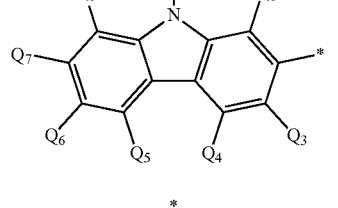
(TEMP-81)
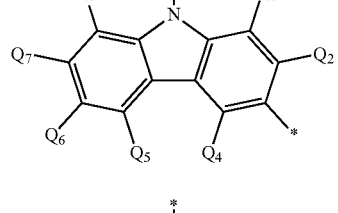
(TEMP-82)
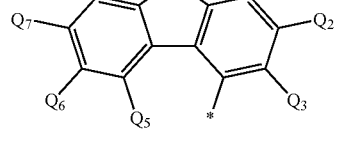
In these formulae (TEMP-69) to (TEMP-82), $Q_1$ to $Q_9$ each are independently a hydrogen atom or a substituent selected from the following "arbitrary substituents".

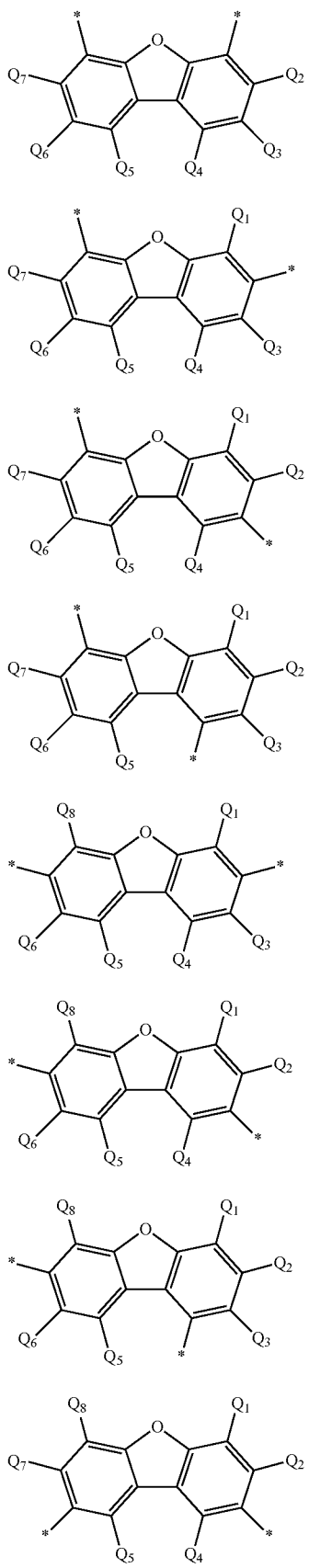
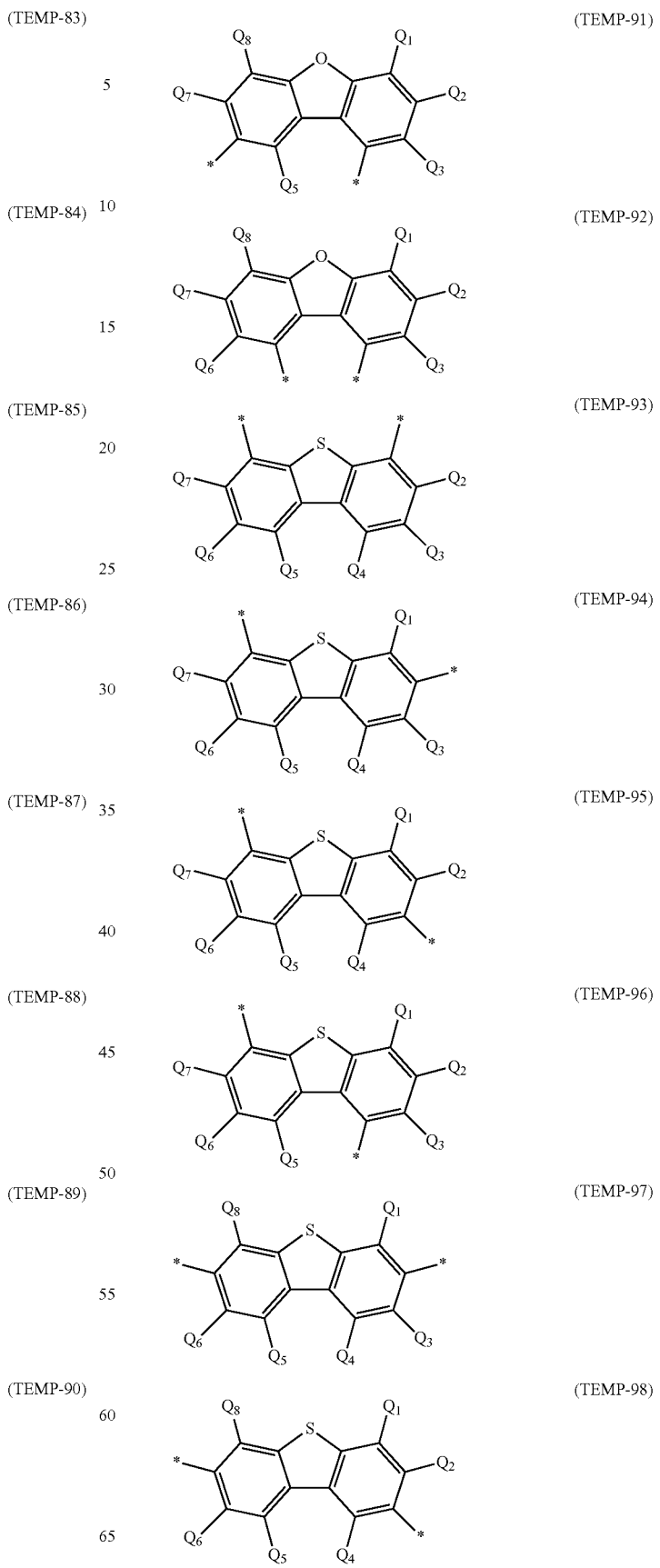

-continued

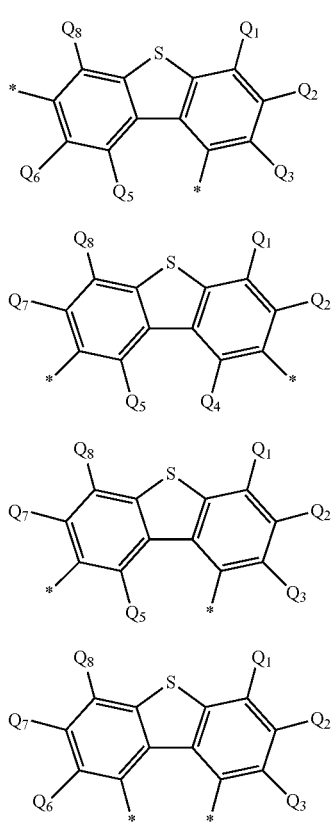

(TEMP-99)

(TEMP-100)

(TEMP-101)

(TEMP-102)

In these formulae (TEMP-83) to (TEMP-102), $Q_1$ to $Q_8$ each are independently a hydrogen atom or a substituent selected from the following "arbitrary substituents".

(21) Substituted or Unsubstituted Alkylene Group

The carbon number of the "unsubstituted alkylene group" of the "substituted or unsubstituted alkylene group" referred to in this description is, unless otherwise noted, 1 to 50, preferably 1 to 20, more preferably 1 to 6.

The "substituted or unsubstituted alkylene group" is, unless otherwise noted, a divalent group derived from the above-mentioned "substituted or unsubstituted alkyl group" by removing one hydrogen atom from the alkyl chain therein. Specific examples of the "substituted or unsubstituted alkylene group" (Group G14 of specific examples) include a divalent group derived from the "substituted or unsubstituted alkyl group" of Group G3 of specific examples by removing one hydrogen atom from the alkyl chain therein.

The above is a description of the "substituents referred to in this description".

(22) Ring Formed by Bonding of Neighboring Two

In this description, "in one or more pairs each formed of neighboring 2 or more selected from . . . , the neighboring two bond to each other to form a substituted or unsubstituted single ring, or bond to each other to form a substituted or unsubstituted condensed ring, or do not bond to each other and form a ring" includes a case where "one pair or more of combinations formed of neighboring two or more bond to each other to form a substituted or unsubstituted single ring", a case where "one pair or more of combinations formed of neighboring two or more bond to each other to form a substituted or unsubstituted condensed ring", and a case where "one pair or more of combinations formed of neighboring two or more do not bond to each other".

As referred to in this description, the case where "one pair or more of combinations formed of neighboring two or more bond to each other to form a substituted or unsubstituted single ring", and the case where "one pair or more of combinations formed of neighboring two or more bond to each other to form a substituted or unsubstituted condensed ring" (hereinafter these cases may be collectively referred to as "a case of bonding to form a ring") are described below with reference to a case of an anthracene compound having an anthracene skeleton represented by the following general formula (TEMP-103):

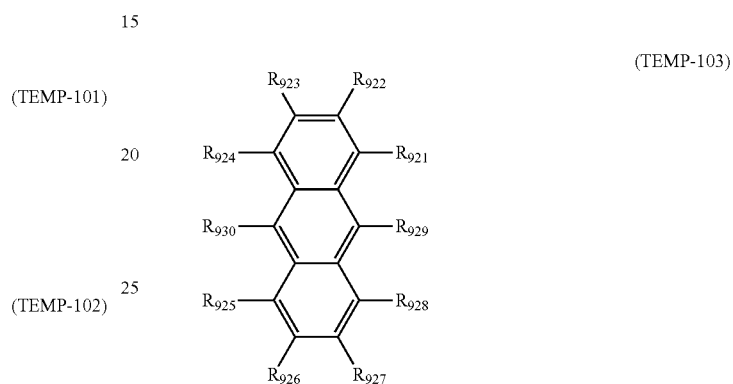

(TEMP-103)

For example, in the case where "one pair or more of combinations formed of neighboring two or more bond to each other to form a ring" among $R_{921}$ to $R_{930}$, the neighboring two to form each pair includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The above-mentioned expression "one pair or more" means that two or more pairs of combinations formed of neighboring two or more may form a ring at the same time. For example, in the case where $R_{921}$ and $R_{922}$ in one pair bond to each other to form a ring $Q_A$ and at the same time where $R_{925}$ and $R_{926}$ in the other pair bond to each other to form a ring $Q_B$, the anthracene compound represented by the general formula (TEMP-103) is represented by the following general formula (TEMP-104).

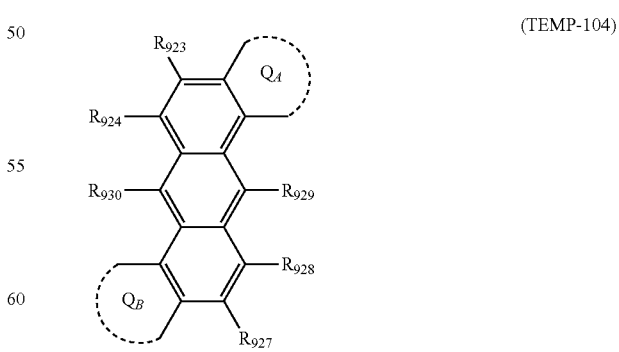

(TEMP-104)

The case where neighboring two in "a combination of neighboring two or more" form a ring includes not only the case where the neighboring two in the neighboring "two" combinations bond like in the above-mentioned case, but also a case where the first neighboring two and the second neighboring two in the neighboring "three or more" combinations bond. Examples of the case include, as in the following general formula (TEMP-105), a case where in a combination of neighboring three ($R_{921}$, $R_{922}$ and $R_{923}$), the first neighboring two ($R_{921}$ and $R_{922}$) bond to each other to form a ring $Q_A$, and the second neighboring two ($R_{922}$ and $R_{923}$) bond to each other to form a ring $Q_C$, thereby forming an ortho-peri-condensed structure as shown in the following general formula (TEMP-105). In the general formula (TEMP-105), the ring $Q_A$ and the ring $Q_C$ share $R_{922}$.

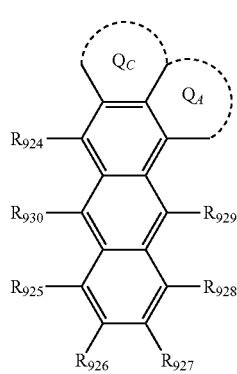

(TEMP-105)

The "single ring" or "condensed ring" to be formed by neighboring two along with the two carbon atoms of the skeleton to which the neighboring two bond may be a saturated ring or an unsaturated ring. Also in the case where "one pair of neighboring two" form "a single ring" or "a condensed ring", the "single ring" or the "condensed ring" may form a saturated ring or an unsaturated ring. For example, the ring $Q_A$ and the ring $Q_B$ formed in the general formula (TEMP-104) each are a "single ring" or a "condensed ring". In the general formula (TEMP-105), the $Q_A$ and the $Q_C$ are condensed to form a condensed ring. When the ring $Q_A$ in the general formula (TEMP-104) is a benzene ring, the ring $Q_A$ is a single ring. When the ring $Q_A$ in the general formula (TEMP-104) is a naphthalene ring, the ring $Q_A$ is a condensed ring.

The "unsaturated ring" means an aromatic hydrocarbon ring, a partially hydrogenated aromatic hydrocarbon ring, an aromatic heterocyclic ring, and a partially hydrogenated aromatic heterocyclic ring. The "saturated ring" means a saturated aliphatic hydrocarbon ring or a saturated nonaromatic hetero ring.

Specific examples of the aromatic hydrocarbon ring include structures formed by terminating the aryl groups listed as specific examples in Group G1 of specific examples with a hydrogen atom.

Specific examples of the aromatic hetero ring include structures formed by terminating the aromatic heterocyclic groups listed as specific examples in Group G2 of specific examples with a hydrogen atom.

Specific examples of the aliphatic hydrocarbon ring include structures formed by terminating the cycloalkyl groups listed as specific examples in Group G6 of specific examples with a hydrogen atom.

"To form a ring" means that plural atoms alone of the mother skeleton, or plural atoms of the mother skeleton and any other one or more elements form a ring. For example, in the general formula (TEMP-104), the ring $Q_A$ formed by $R_{921}$ and $R_{922}$ bonding to each other means a ring formed of the carbon atom of the anthracene skeleton to which $R_{921}$ bonds, the carbon atom of the anthracene skeleton to which $R_{922}$ bonds, and one or more other elements. One example is described. In the case where $R_{921}$ and $R_{922}$ bond to each other to form the ring $Q_A$, the carbon atom of the anthracene skeleton to which $R_{921}$ bonds, the carbon atom of the anthracene skeleton to which $R_{922}$ bonds, and four carbon atoms form a monocyclic unsaturated ring, the ring formed of $R_{921}$ and $R_{922}$ is a benzene ring.

Here, "any other element" is, unless otherwise specifically noted in this description, preferably at least one element selected from the group consisting of a carbon element, a nitrogen element, an oxygen element, and a sulfur element. In the case where the other element is, for example, a carbon element or a nitrogen element, a hydrogen atom may bond thereto, or may be substituted with "an arbitrary substituent" to be mentioned hereinunder. In the case of containing any other atom than a carbon atom, the ring to be formed is a hetero ring.

The number of "one or more other arbitrary elements" constituting a single ring or a condensed ring is, unless otherwise specifically noted in this description, preferably 2 to 15, more preferably 3 to 12, even more preferably 3 to 5.

Unless otherwise specifically noted in this description, among the "single ring" and the "condensed ring", the "single ring" is preferred.

Unless otherwise specifically noted in this description, among the "saturated ring" and the "unsaturated ring", the "unsaturated ring" is preferred.

Unless otherwise specifically noted in this description, the "single ring" is preferably a benzene ring.

Unless otherwise specifically noted in this description, the "unsaturated ring" is preferably a benzene ring.

In the case where in each pair of "one or more combinations formed of neighboring two or more" "bond to each other to form a substituted or unsubstituted single ring", or "bond to each other to form a substituted or unsubstituted condensed ring", unless otherwise specifically noted in this description, preferably, one pair or more of combinations formed of neighboring two or more bond to each other to form a substituted or unsubstituted "unsaturated ring" composed of plural two atoms of the mother skeleton, and at least one element selected from a group consisting of 1 to 15 elements of a carbon element, a nitrogen element, an oxygen element and a sulfur element.

In the case where the "single ring" or the "condensed ring" has a substituent, the substituent may be "any arbitrary substituent" to be mentioned below. Specific examples of the substituent in the case where the "single ring" or the "condensed ring" has a substituent include the substituents referred to in the section of "substituents referred to in this description" given hereinabove.

In the case where the "saturated ring" or the "unsaturated ring" has a substituent, the substituent may be "any arbitrary substituent" to be mentioned below. Specific examples of the substituent in the case where the "single ring" or the "condensed ring" has a substituent include the substituents referred to in the section of "substituents referred to in this description" given hereinabove.

The above is a description of a case where "in one or more pairs each formed of neighboring 2 or more selected from . . . , the neighboring two bond to each other to form a substituted or unsubstituted single ring" and a case where "in one or more pairs each formed of neighboring 2 or more selected from . . . , the neighboring two bond to each other to form a substituted or unsubstituted condensed ring" ("a case of bonding to form a ring").

(23) Substituent in a Case of "Substituted or Unsubstituted"

In one embodiment of this description, examples of the substituent in a case of the above-mentioned "substituted or unsubstituted" (in this description, this may be referred to as "any arbitrary substituent") include groups selected from the group consisting of an unsubstituted aryl group having 6 to 50 ring carbon atoms,
an unsubstituted heterocyclic group having 5 to 50 ring atoms,
an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R^{901}$)($R^{902}$)($R^{903}$),
—O—($R^{904}$),
—S—($R^{905}$),
—N($R^{906}$)($R^{907}$),
a halogen atom,
a cyano group, and
a nitro group.

$R^{901}$ to $R^{907}$ each independently represent:
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted heterocyclic group having 5 to 50 ring atoms.

In the case of having two or more $R^{901}$'s, the two or more $R^{901}$'s are the same as or different from each other,
in the case of having two or more $R^{902}$'s, the two or more $R^{902}$'s are the same as or different from each other,
in the case of having two or more $R^{903}$'s, the two or more $R^{903}$'s are the same as or different from each other,
in the case of having two or more $R^{904}$'s, the two or more $R^{904}$'s are the same as or different from each other,
in the case of having two or more $R^{905}$'s, the two or more $R^{905}$'s are the same as or different from each other,
in the case of having two or more $R^{906}$'s, the two or more $R^{906}$'s are the same as or different from each other,
in the case of having two or more $R^{907}$'s, the two or more $R^{907}$'s are the same as or different from each other.

In one embodiment, the "arbitrary substituent" is a group selected from the group consisting of:
an alkyl group having 1 to 50 carbon atoms,
an aryl group having 6 to 50 ring carbon atoms, and
a heterocyclic group having 5 to 50 ring atoms.

In one embodiment, the "arbitrary substituent" is a group selected from
the group consisting of
an alkyl group having 1 to 18 carbon atoms,
an aryl group having 6 to 18 ring carbon atoms, and
a heterocyclic group having 5 to 18 ring atoms.

Specific examples of the group of the above-mentioned arbitrary substituent are the specific examples of the substituent described in the section of "substituents referred to in this description" given hereinabove.

Unless otherwise specifically indicated in this description, arbitrary neighboring substituents may bond to each other to form "a saturated ring" or "an unsaturated ring", and preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring.

Unless otherwise specifically indicated in this description, arbitrary substituents may further have a substituent. The substituents that arbitrary substituents may further have are the same as the arbitrary substituents mentioned above.

In this description, the numeral range expressed as "to" means a range that includes the numeral value before "to" as the lower limit and the numeral value after "to" as the upper limit.

The compound of the present invention is represented by the following formula (1).

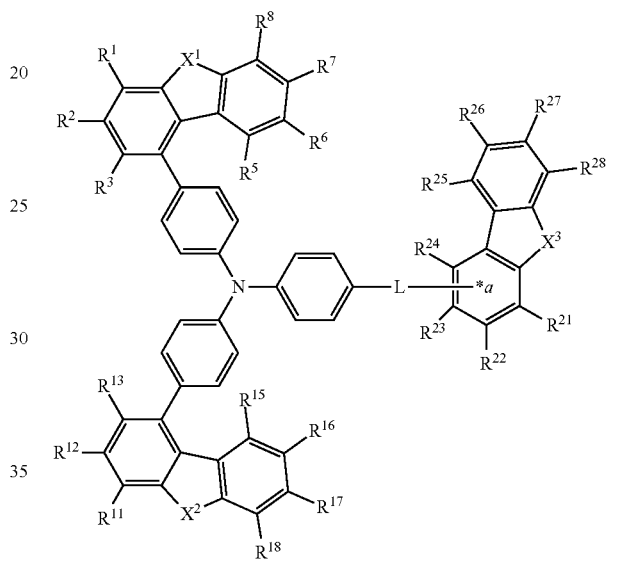

(1)

The compound of the present invention is preferably represented by any of the following formulae (2) to (5):

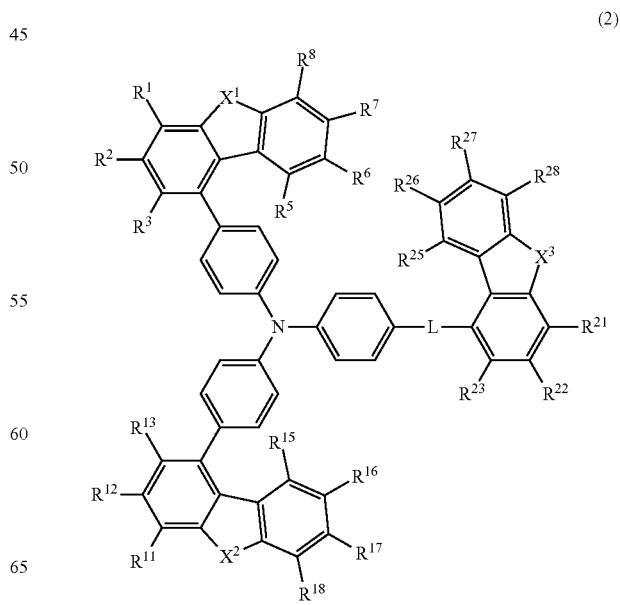

(2)

-continued (3)
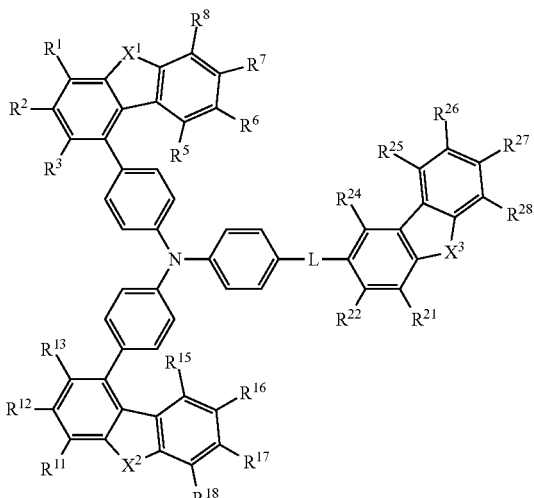

(4)
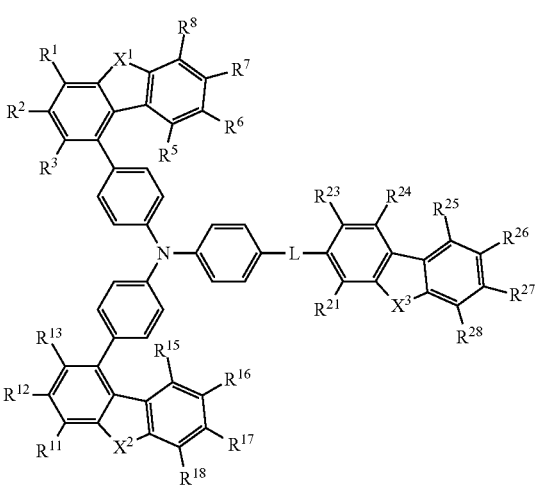

(5)
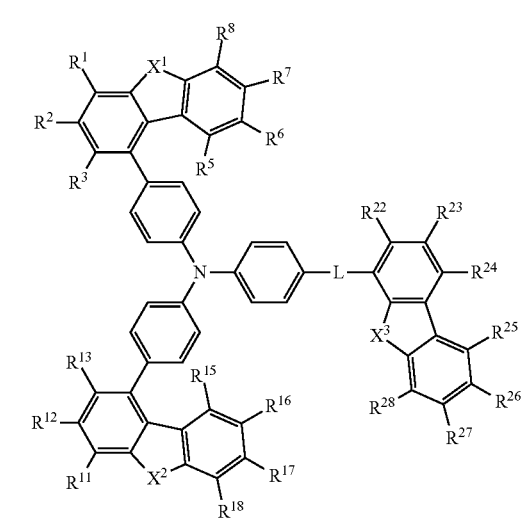

Hereinunder the symbols in the above formulae and in the formulae to be mentioned below are described.

One of $X^1$ and $X^2$ is an oxygen atom, and the other is an oxygen atom or a sulfur atom, preferably both $X^1$ and $X^2$ are oxygen atoms.

$X^3$ is selected from an oxygen atom or a sulfur atom. In one embodiment of the present invention, $X^3$ is an oxygen atom, and in another embodiment, $X^3$ is a sulfur atom.

In one embodiment of the present invention, $X^1$, $X^2$ and $X^3$ are all oxygen atoms. In another embodiment, $X^1$ and $X^2$ are oxygen atoms and $X^3$ is a sulfur atom. In still another embodiment, one of $X^1$ and $X^2$ is an oxygen atom, the other is a sulfur atom, and $X^3$ is an oxygen atom. In still another embodiment, one of $X^1$ and $X^2$ is an oxygen atom, the other is a sulfur atom, and $X^3$ is an oxygen atom.

$R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R^{901}$)($R^{902}$)($R^{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, and preferably, each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R^{901}$)($R^{902}$)($R^{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, and a substituted or unsubstituted aralkyl group having 7 to 50 carbon atoms, even more preferably, each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R^{901}$)($R^{902}$)($R^{903}$), a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, and a substituted or unsubstituted aralkyl group having 7 to 50 carbon atoms.

However, one of $R^{21}$ to $R^{24}$ is a single bond bonding to L via *a.

Details of the substituted or unsubstituted aryl group having 6 to 50 ring carbon atoms are as described in "(1) substituted or unsubstituted aryl group", more preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, or a 2-naphthyl group, even more preferably a phenyl group, a p-biphenyl group, a m-biphenyl group, an o-biphenyl group, a 1-naphthyl group, or a 2-naphthyl group.

Details of the substituted or unsubstituted heterocyclic group having 5 to 50 ring atoms are as described in "(2) substituted or unsubstituted heterocyclic group", and are more preferably a monocyclic aromatic heterocyclic group or a condensed aromatic heterocyclic group. More preferred are a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, and a diazadibenzothiophenyl group, and even more preferred are a pyridyl group, a pyrimidinyl group, a triazinyl group, a quinolyl group, an isoquinolyl group, a quinazolinyl group, a benzimidazolyl group, a phenanthrolinyl group, and a carbazolyl group (a 1-carbazolyl group, a 2-carbazolyl group, a 3-carbazolyl group, a 4-carbazolyl group, or a 9-carbazolyl group).

Details of the substituted or unsubstituted alkyl group having 1 to 50 carbon atoms are as described in "(3) substituted or unsubstituted alkyl group", and are preferably a methyl group, an ethyl group, an isopropyl group or a t-butyl group, more preferably a methyl group, an isopropyl group or a t-butyl group.

Details of the substituted or unsubstituted cycloalkyl group having 3 to 50 ring carbon atoms are as described in "(6) substituted or unsubstituted cycloalkyl group", and are preferably a cyclopentyl group, a cyclohexyl group, a 1-adamantyl group, a 2-adamantyl group, a 1-norbornyl group or a 2-norbornyl group, more preferably a cyclohexyl group, a 1-adamantyl group, a 2-adamantyl group, a 1-norbornyl group or a 2-norbornyl group.

$R^{901}$, $R^{902}$, and $R^{903}$ in the group represented by —Si($R^{901}$)($R^{902}$)($R^{903}$) each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms.

Details of the substituted or unsubstituted aryl group having 6 to 50 carbon atoms, details of the substituted or unsubstituted heterocyclic group having 5 to 50 ring atoms, details of the substituted or unsubstituted alkyl group having 1 to 50 carbon atoms, and details of the substituted or unsubstituted cycloalkyl group having 3 to 50 ring carbon atoms each are as described in "(7) group represented by —Si($R^{901}$)($R^{902}$)($R^{903}$)", and in relation to $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$.

The group represented by —Si($R^{901}$)($R^{902}$)($R^{903}$) is preferably a tri-substituted silyl group, more preferably a trimethylsilyl group, a triethylsilyl group, a t-butyldimethylsilyl group, a propyldimethylsilyl group, an isopropyklimethylsilyl group, a triphenylsilyl group, a phenyldimethylsilyl group, a t-butyldiphenylsilyl group or a tritolylsilyl group.

Details of the halogen atom are as described in "(11) halogen atom", and a fluorine atom is preferred.

Details of the substituted or unsubstituted haloalkyl group having 1 to 50 carbon atoms are as described in "(12) substituted or unsubstituted haloalkyl group", and are preferably a fluoroalkyl group, more preferably a heptafluoropropyl group, a pentafluoroethyl group, a 2,2,2-trifluoroethyl group, or a trifluoromethyl group, even more preferably a pentafluoroethyl group, a 2,2,2-trifluoroethyl group or a trifluoromethyl group, and a trifluoromethyl group is especially preferred.

Details of the substituted or unsubstituted alkoxy group having 1 to 50 carbon atoms are as described in "(13) substituted or unsubstituted alkoxy group", and are preferably a t-butoxy group, a propoxy group, an ethoxy group or a methoxy group, more preferably an ethoxy group or a methoxy group, even more preferably a methoxy group.

Details of the substituted or unsubstituted aryloxy group having 6 to 50 ring carbon atoms are as described in "(15) substituted or unsubstituted aryloxy group", and are preferably a terphenyloxy group, a biphenyloxy group, or a phenoxy group, more preferably a biphenyloxy group or a phenoxy group, even more preferably a phenoxy group.

Details of the substituted or unsubstituted haloalkoxy group having 1 to 50 carbon atoms are as described in "(17) substituted or unsubstituted haloalkoxy group", and preferred is a fluoroalkoxy group, more preferred is a heptafluoropropoxy group, a pentafluoroethoxy group, a 2,2,2-trifluoroethoxy group, or a trifluoromethoxy group, even more preferred is a pentafluoroethoxy group, a 2,2,2-trifluoroethoxy group, or a trifluoromethoxy group, and especially preferred is a trifluoromethoxy group.

Details of the substituted or unsubstituted aralkyl group having 7 to 50 carbon atoms are as described in "(18) substituted or unsubstituted aralkyl group", and are preferably a benzyl group, a phenethyl group, or a phenylpropyl group, more preferably a benzyl group.

In one or more pairs each containing 2 or more neighboring groups selected from $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$, the neighboring two bond to each other to form a substituted or unsubstituted ring, or do not bond to each other.

The substituted or unsubstituted ring that the above-mentioned two along with the two ring carbon atoms to which they bond optionally form is a substituted or unsubstituted single ring or a substituted or unsubstituted condensed ring.

The substituted or unsubstituted single ring or the substituted or unsubstituted condensed ring is selected, for example, from a substituted or unsubstituted aromatic hydrocarbon ring, a substituted or unsubstituted aliphatic hydrocarbon ring, a substituted or unsubstituted aromatic hetero ring, and a substituted or unsubstituted aliphatic hetero ring.

For example, the aromatic hydrocarbon ring is a benzene ring, a biphenylene ring, a naphthalene ring, an anthracene ring, a benzanthracene ring, a phenanthrene ring, a benzophenanthrene ring, a phenalene ring, a pyrene ring, a chrysene ring, a 1,1-dimethylindene ring, or a triphenylene ring, preferably a benzene ring or a naphthalene ring, more preferably a benzene ring.

The aliphatic hydrocarbon ring is, for example, a cyclopentene ring, a cyclopentadiene ring, a cyclohexene ring, a cyclohexadiene ring, or an aliphatic hydrocarbon ring formed by partially hydrogenating the aromatic hydrocarbon ring.

The aromatic hetero ring is, for example, a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, or a benzocarbazole ring.

The aliphatic hetero ring is, for example, an aliphatic hetero ring formed by partially hydrogenating the aromatic hetero ring.

Other details of the substituted or unsubstituted ring that the neighboring two optionally form are as described in "(22) Ring formed by bonding of neighboring two".

In one embodiment of the present invention, preferably, $R^1$ and $R^{11}$ are the same, $R^2$ and $R^{12}$ are the same, $R^3$ and $R^{13}$ are the same, $R^5$ and $R^{15}$ are the same, $R^6$ and $R^{16}$ are the same, $R^7$ and $R^{17}$ are the same, and $R^8$ and $R^{18}$ are the same.

In one embodiment of the present invention, $R^1$ to $R^3$, $R^5$ to $R^8$, $R^{11}$ to $R^{13}$, $R^{15}$ to $R^{18}$, $R^{25}$ to $R^{28}$, and $R^{21}$ to $R^{24}$ bonding to L not a single bond may all be hydrogen atoms.

L is selected from a single bond, a substituted or unsubstituted phenylene group, and a substituted or unsubstituted naphthylene group, preferably from a single bond and a substituted or unsubstituted phenylene group.

The phenylene group of the substituted or unsubstituted phenylene group is an o-phenylene group, a m-phenylene group or a p-phenylene group.

The naphthylene group of the substituted or unsubstituted naphthylene group is preferably selected from a 1,4-naphthylene group and a 2,6-naphthylene group.

In one embodiment of the present invention, L is preferably a single bond. In the case where L is a single bond, the compound of the present invention is represented by any of the following formulae (6) to (9):

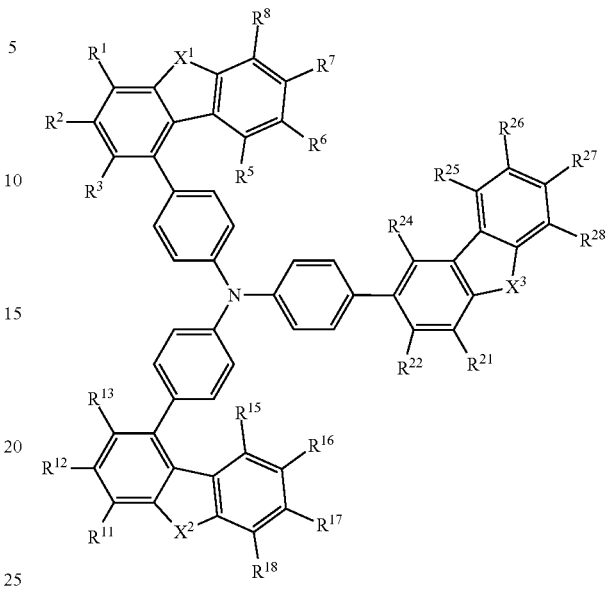

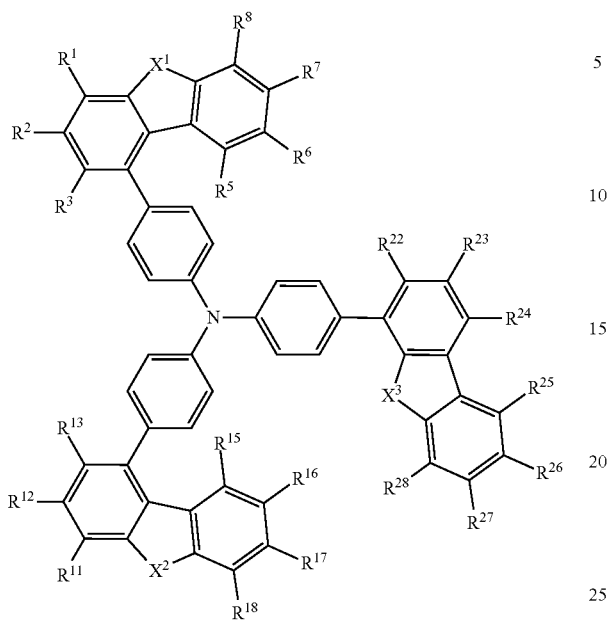

(9)

In the formulae (6) to (9), $X^1$, $X^2$, $X^3$, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the formula (1).

In one embodiment of the present invention, L is preferably a substituted or unsubstituted phenylene group. In the case where L is a substituted or unsubstituted phenylene group, the compound of the present invention is represented by any of the following formulae (10) to (13):

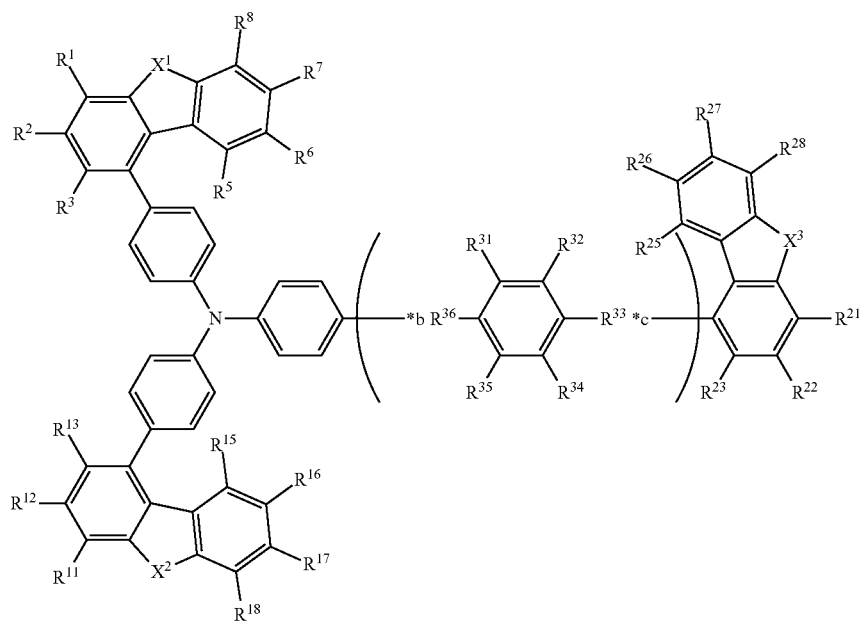

(10)

(11)
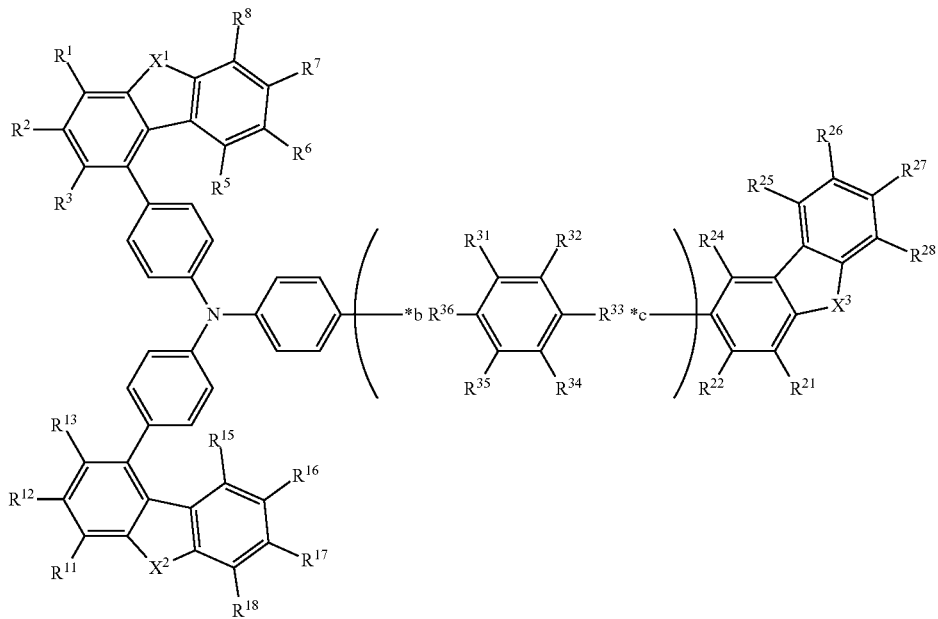
(12)
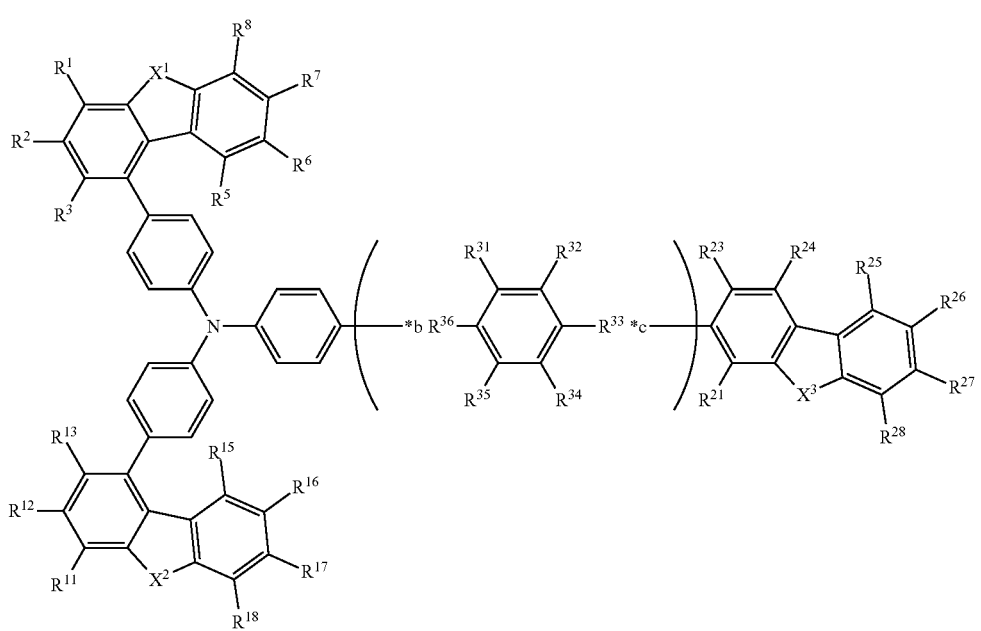

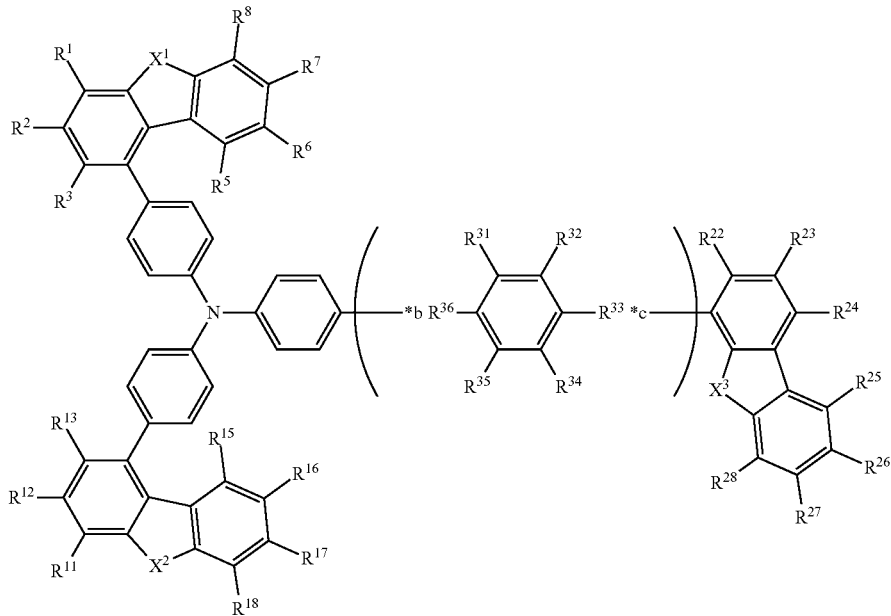

(13)

In the formulae (10) to (13):

$X^1$, $X^2$, $X^3$, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the formula (1), $R^{31}$ to $R^{36}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R^{901}$)($R^{902}$)($R^{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, provided that one selected from $R^{31}$ to $R^{36}$ is a single bond bonding to *b, and the other selected from $R^{31}$ to $R^{36}$ is a single bond bonding to *c.

Details of the groups represented by $R^{31}$ to $R^{36}$ each are as described in relation to $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$.

In one embodiment of the present invention, $R^{36}$ is a single bond bonding to *b, and $R^{33}$ is a single bond bonding to *c. In another embodiment, $R^{36}$ is a single bond bonding to *b, and $R^{32}$ is a single bond bonding to *c. In still another embodiment, $R^{36}$ is a single bond bonding to *b, and $R^{31}$ is a single bond bonding to *c.

In one embodiment of the present invention, $R^{31}$ to $R^{36}$ that are not a single bond bonding to *b and are not a single bond bonding to *c may all be hydrogen atoms.

In one embodiment of the present invention, L is preferably a substituted or unsubstituted naphthylene group. When L is a substituted or unsubstituted naphthylene group, the compound of the present invention is represented by any of the following formulae (14) to (17):

(14)
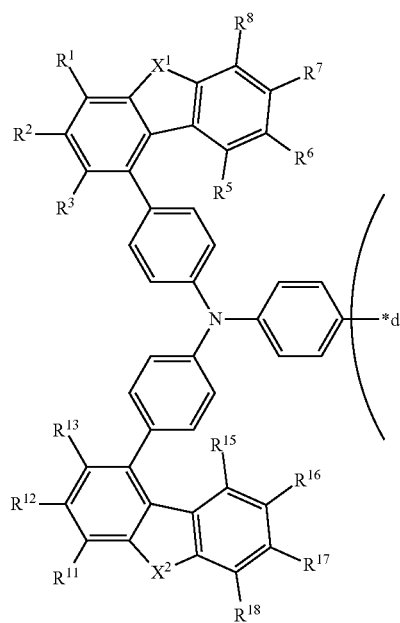 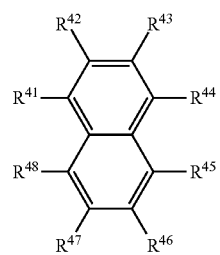 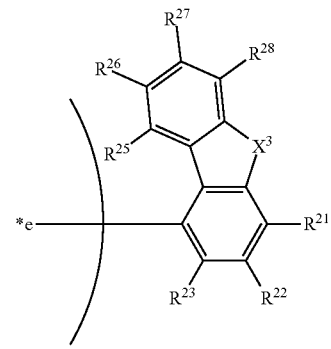
(15)
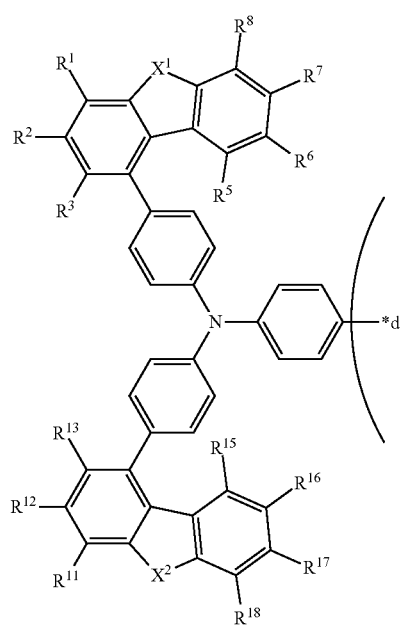 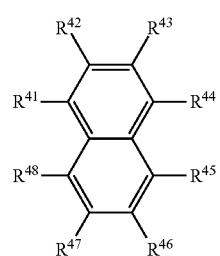 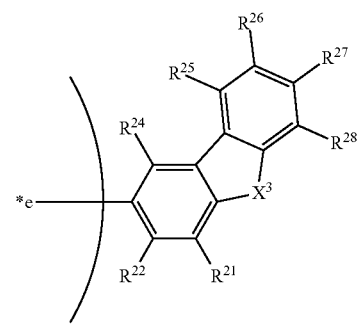

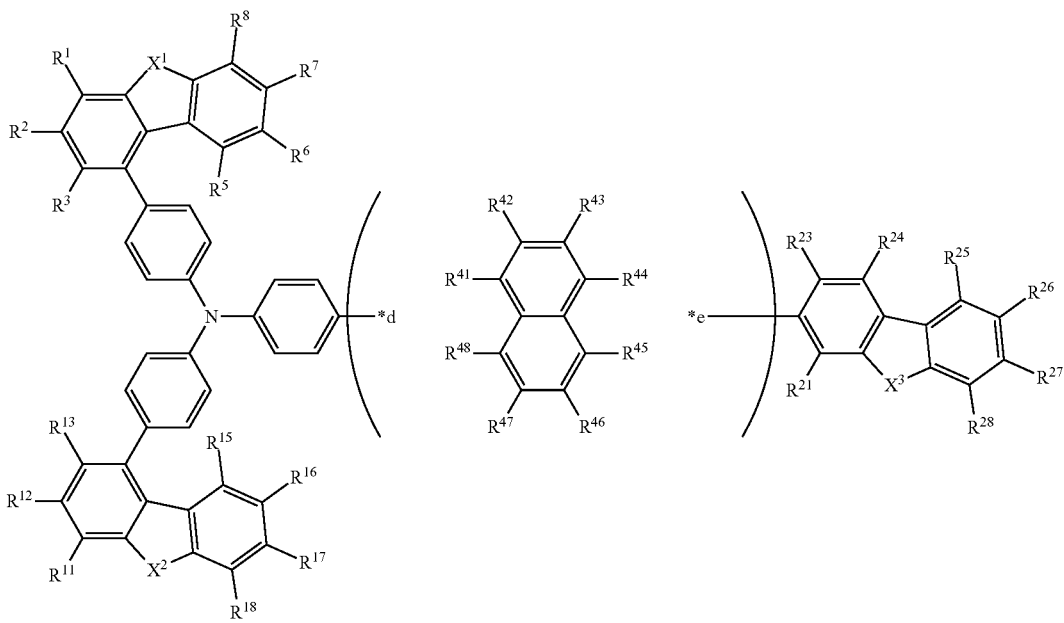

(16)

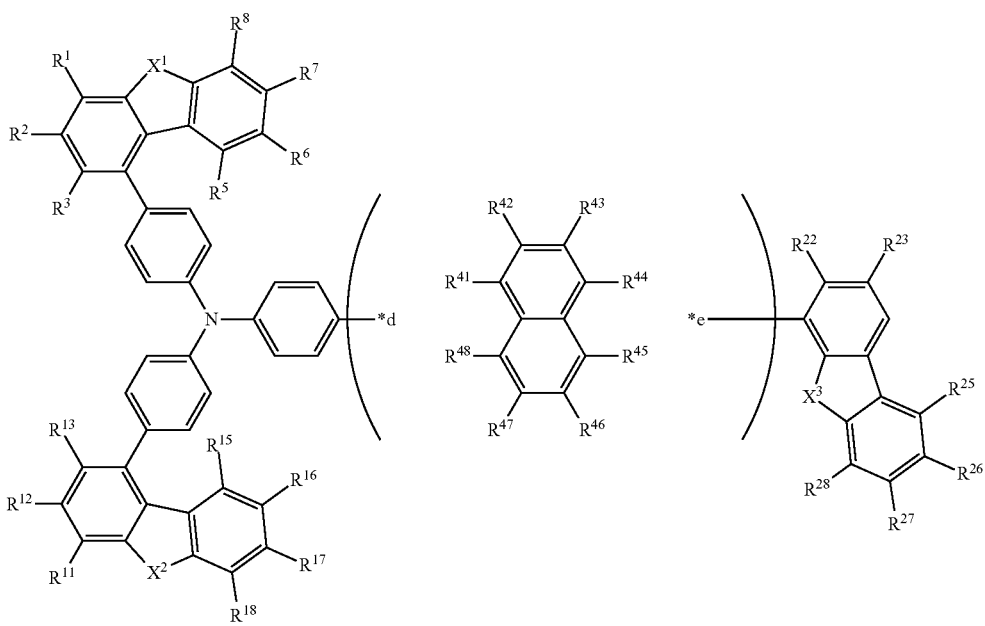

(17)

In these formulae, $X^1$, $X^2$, $X^3$, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the formula (1), $R^{41}$ to $R^{48}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si($R^{901}$)($R^{902}$)($R^{903}$), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, provided that one selected from $R^{41}$ to $R^{48}$ is a single bond bonding to *d, and the other one selected from $R^{41}$ to $R^{48}$ is a single bond bonding to *e.

Details of the groups represented by $R^{41}$ to $R^{48}$ each are as described in relation to $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$.

In one embodiment of the present invention, $R^{4'}$ is a single bond bonding to *d, and $R^{44}$ is a single bond bonding to *e. In another embodiment, $R^{42}$ is a single bond bonding to *d, and $R^{46}$ is a single bond bonding to *e.

In one embodiment of the present invention, $R^{41}$ to $R^{48}$ that are not a single bond bonding to *d and are not a single bond bonding to *e may all be hydrogen atoms.

Details of the substituent (arbitrary substituent) in the case of "substituted or unsubstituted" described in relation to the above formulae are as described in "(23) substituent in a case of "substituted or unsubstituted"".

As noted above, the "hydrogen atom" referred to in this description includes a light hydrogen (protium) atom, a heavy hydrogen (deuterium) atom, and a tritium atom. Therefore, the compound of the present invention may include a naturally occurring heavy hydrogen atom.

In addition, a heavy hydrogen atom may be intentionally introduced into the compound of the present invention by using a deuterated compound as a part or whole of the raw material compounds. Thus, in an embodiment of the invention, the compound of the present invention contains at least one heavy hydrogen atom. Therefore, the compound of the present invention may be a compound represented by the formula (1) or any other formula, in which at least one hydrogen atom contained in the compound is a heavy hydrogen atom.

At least one hydrogen atom selected from the hydrogen atom represented by any of $R^1$ to $R^3$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^1$ to $R^3$ has; the hydrogen atom represented by any of $R^5$ to $R^8$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^5$ to $R^8$ has; the hydrogen atom represented by any of $R^{11}$ to $R^{13}$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{11}$ to $R^{13}$ has; the hydrogen atom represented by any of $R^{15}$ to $R^{18}$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{15}$ to $R^{18}$ has; the hydrogen atom represented by any of $R^{21}$ to $R^{24}$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{21}$ to $R^{24}$ has; the hydrogen atom represented by any of $R^{25}$ to $R^{28}$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{25}$ to $R^{28}$ has; the hydrogen atom that the substituted or unsubstituted, aryl group, heterocyclic group, alkyl group or cycloalkyl group represented by any of $R^{901}$ to $R^{903}$ has; the hydrogen atom represented by any of $R^{31}$ to $R^{36}$; the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{31}$ to $R^{36}$ has; the hydrogen atom represented by any of $R^{41}$ to $R^{48}$; and the hydrogen atom that the substituted or unsubstituted, aryl group, heterocyclic group, alkyl group, cycloalkyl group, haloalkyl group, alkoxy group, aryloxy group, haloalkoxy group or aralkyl group represented by any of $R^{41}$ to $R^{48}$ has may be a heavy hydrogen atom.

The deuteration rate of the compound of the present invention (the ratio of the number of heavy hydrogen atoms to the total number of hydrogen atoms in the compound of the present invention) depends on the deuteration rate of the raw material compound to be used. It is generally difficult to use the raw material compounds each having a deuteration rate of 100%. Therefore, the deuteration rate of the compound of the present invention is less than 100% and 1% or more, preferably 3% or more, more preferably 5% or more, and still more preferably 10% or more.

The compound of the present invention may be a mixture of a deuterated compound (a compound into which a heavy hydrogen atom has been intentionally introduced) and a non-deuterated compound or a mixture of two or more compounds having different deuteration rates. The deuteration rate of such a mixture (the ratio of the number of heavy hydrogen atoms to the total number of hydrogen atoms in the compound of the present invention contained in the mixture) is 1% or more, preferably 3% or more, more preferably 5% or more, and still more preferably 10% or more, and less than 100%.

In the compound of the present invention, at least one hydrogen atom selected from the hydrogen atom represented by any of $R^1$ to $R^3$ and $R^5$ to $R^8$, as well as the hydrogen atom that the substituted or unsubstituted aryl group, heterocyclic group, alkyl group, cycloalkyl group, haloalkyl group, alkoxy group, aryloxy group, haloalkoxy group or aralkyl group, as represented by any of $R^1$ to $R^3$ and $R^5$ to $R^8$, has may be a heavy hydrogen atom. The deuteration rate (the ratio of the number of heavy hydrogen atoms to the total number of hydrogen atoms that $R^1$ to $R^3$ and $R^5$ to $R^8$ have) is 1% or more, preferably 3% or more, more preferably 5% or more, and still more preferably 10% or more, and less than 100%.

In the compound of the present invention, at least one hydrogen atom selected from the hydrogen atom represented by any of $R^{11}$ to $R^{13}$ and $R^{15}$ to $R^{18}$, and the hydrogen atom that the substituted or unsubstituted aryl group, heterocyclic group, alkyl group, cycloalkyl group, haloalkyl group, alkoxy group, aryloxy group, haloalkoxy group or aralkyl group, as represented by any of $R^{11}$ to $R^{13}$ and $R^{15}$ to $R^{18}$, has may be a heavy hydrogen atom. The deuteration rate (the ratio of the number of heavy hydrogen atoms to the total number of hydrogen atoms that $R^{11}$ to $R^{13}$ and $R^{15}$ to $R^{18}$ have) is 1% or more, preferably 3% or more, more preferably 5% or more, and still more preferably 10% or more, and less than 100%.

In the compound of the present invention, at least one hydrogen atom selected from the hydrogen atom represented by any of $R^{21}$ to $R^{24}$ and $R^{25}$ to $R^{28}$, and the hydrogen atom that the substituted or unsubstituted, aryl group, heterocyclic group, alkyl group, cycloalkyl group, haloalkyl group, alkoxy group, aryloxy group, haloalkoxy group or aralkyl group, as represented by any of $R^{21}$ to $R^{24}$ and $R^{25}$ to $R^{28}$, has may be a heavy hydrogen atom. The deuteration rate (the ratio of the number of heavy hydrogen atoms to the total number of hydrogen atoms that $R^{21}$ to $R^{24}$ and $R^{25}$ to $R^{28}$ have) is 1% or more, preferably 3% or more, more preferably 5% or more, and still more preferably 10% or more, and less than 100%.

In the compound of the present invention, at least one hydrogen atom that the substituted or unsubstituted, aryl group, heterocyclic group, alkyl group or cycloalkyl group, as represented by any of $R^{901}$ to $R^{903}$, has may be a heavy hydrogen atom. The deuteration rate (the ratio of the number of heavy hydrogen atoms to the total number of hydrogen atoms that $R^{904}$ to $R^{903}$ have) is 1% or more, preferably 3% or more, more preferably 5% or more, and still more preferably 10% or more, and less than 100%.

In the compound of the present invention, at least one hydrogen atom selected from the hydrogen atom represented by any of $R^{31}$ to $R^{36}$, and the hydrogen atom that the substituted or unsubstituted, aryl group, heterocyclic group, alkyl group, cycloalkyl group, haloalkyl group, alkoxy group, aryloxy group, haloalkoxy group or aralkyl group, as represented by any of $R^{31}$ to $R^{36}$, has may be a heavy hydrogen atom. The deuteration rate (the ratio of the number of heavy hydrogen atoms to the total number of hydrogen atoms that $R^{31}$ to $R^{36}$ have) is 1% or more, preferably 3% or more, more preferably 5% or more, and still more preferably 10% or more, and less than 100%.

In the compound of the present invention, at least one hydrogen atom selected from the hydrogen atom represented by any of $R^{41}$ to $R^{48}$, and the hydrogen atom that the substituted or unsubstituted, aryl group, heterocyclic group, alkyl group, cycloalkyl group, haloalkyl group, alkoxy group, aryloxy group, haloalkoxy group or aralkyl group, as represented by any of $R^{44}$ to $R^{48}$, has may be a heavy hydrogen atom. The deuteration rate (the ratio of the number of heavy hydrogen atoms to the total number of hydrogen atoms that $R^{41}$ to $R^{48}$ have) is 1% or more, preferably 3% or more, more preferably 5% or more, and still more preferably 10% or more, and less than 100%.

One of ordinary skill in the art could easily produce the compound of the present invention by referring to the Synthesis Examples mentioned below and known synthesis methods.

Specific examples of the compound of the present invention are shown below, although not limited thereto.

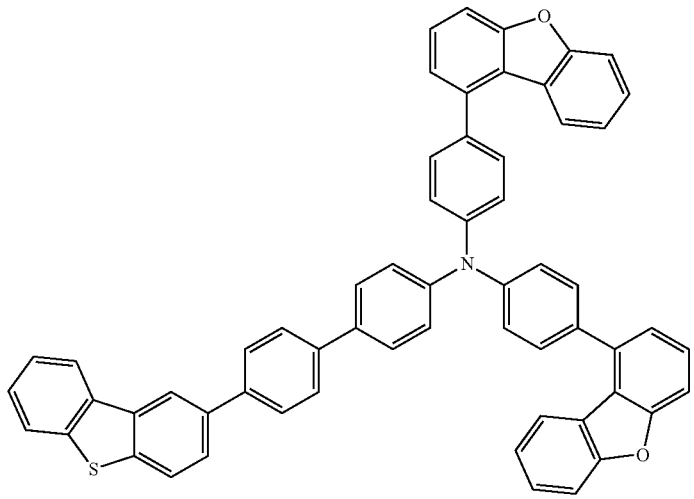

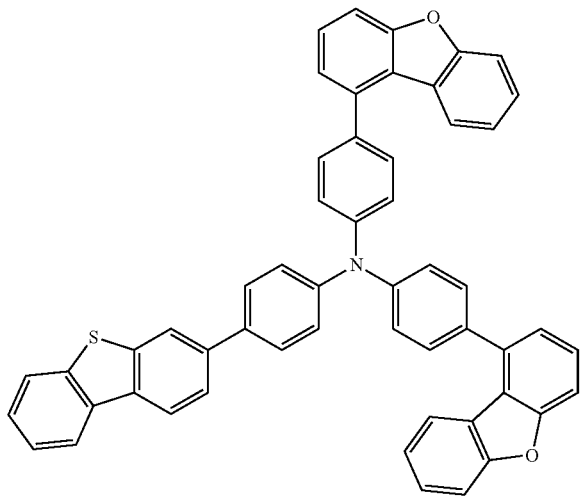

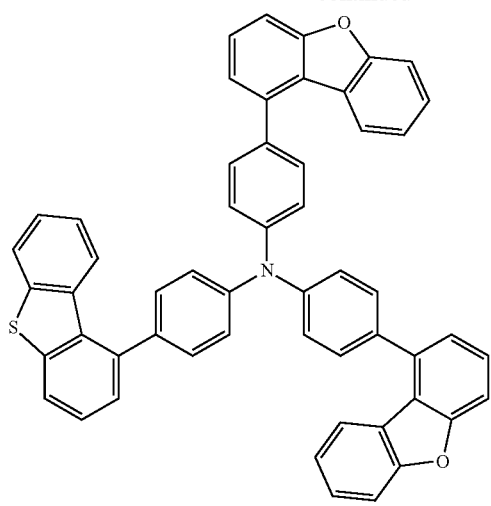
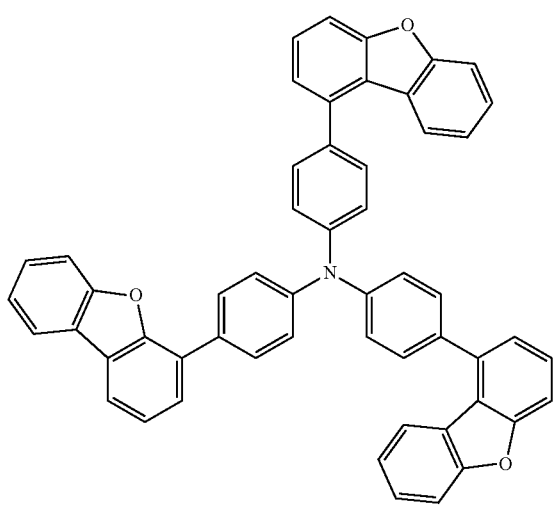
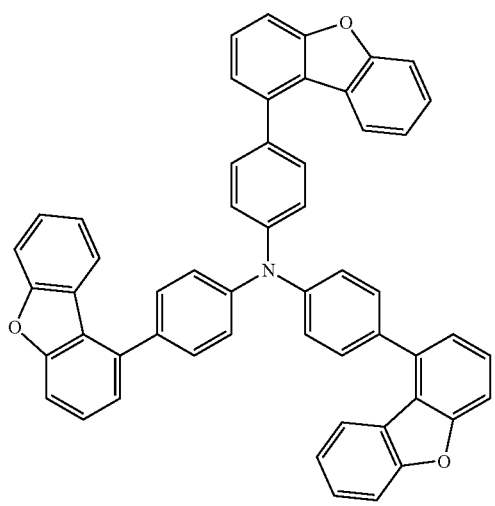

-continued
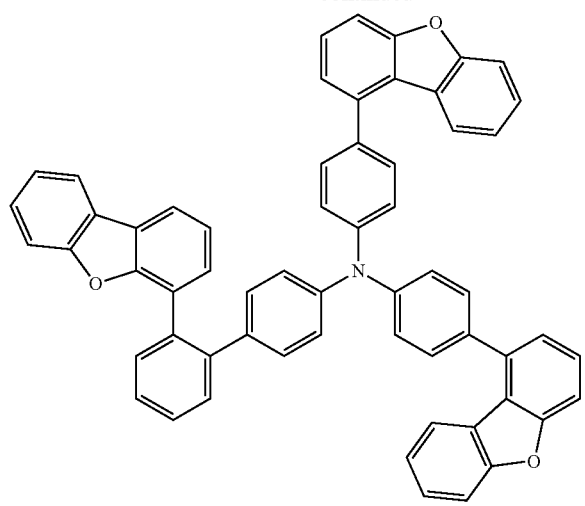
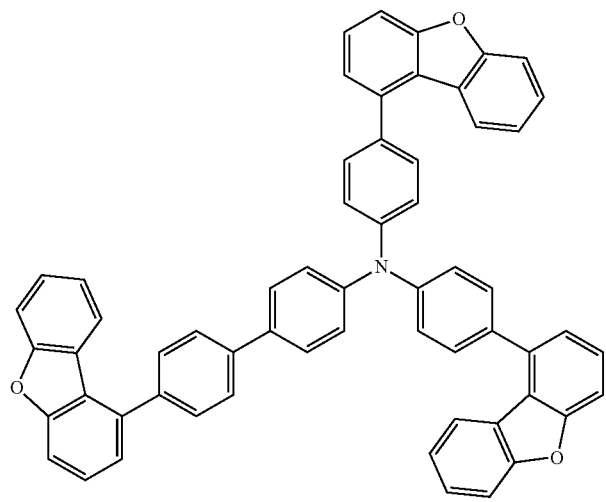
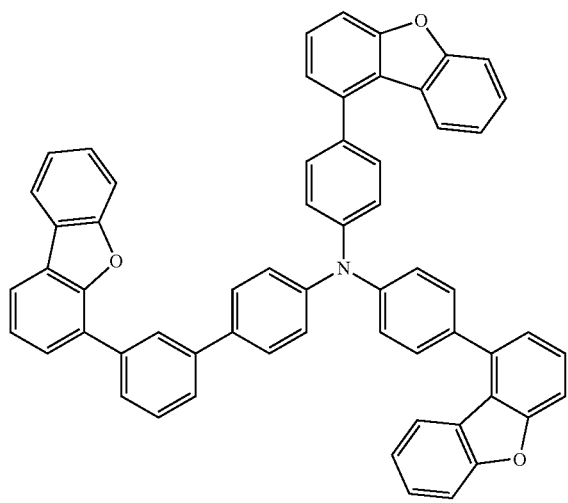

-continued
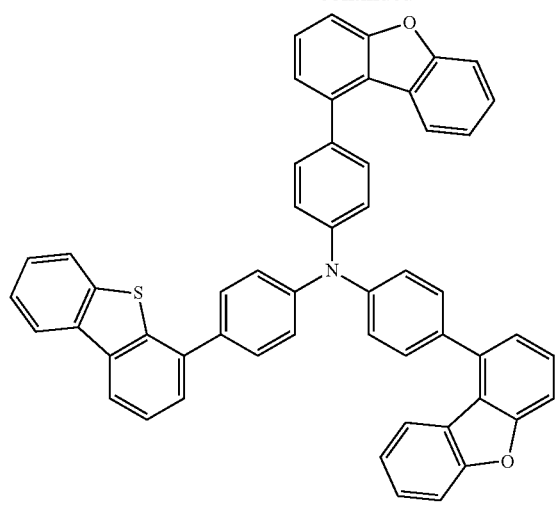
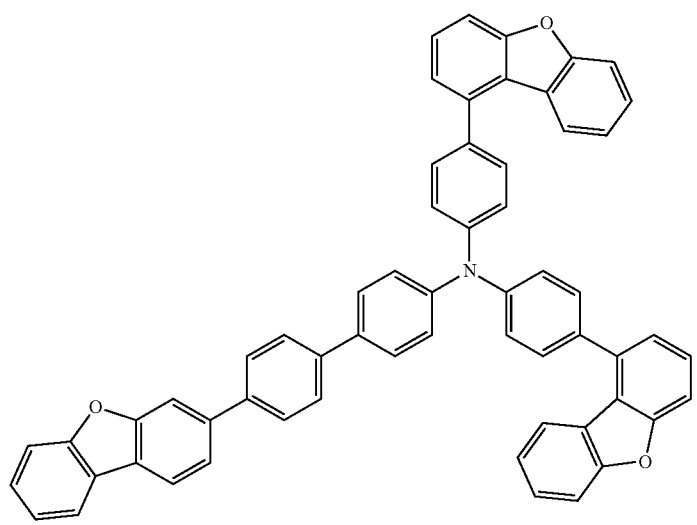
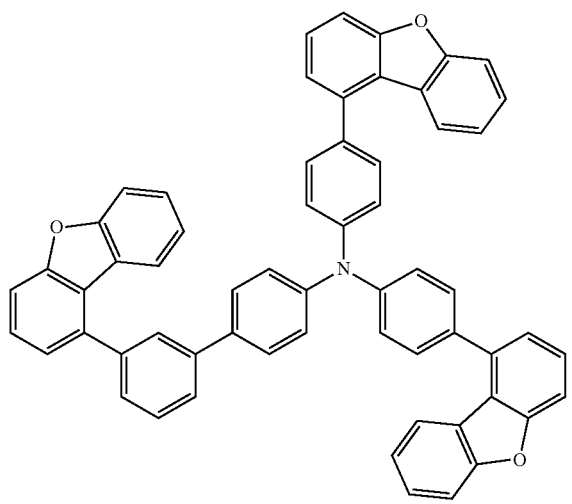

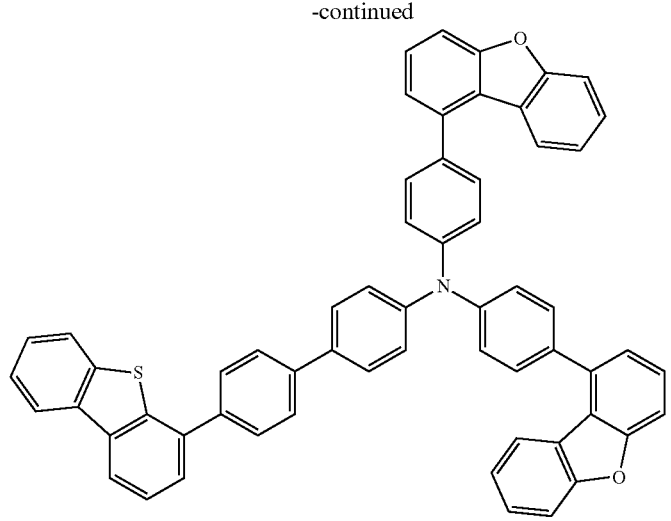
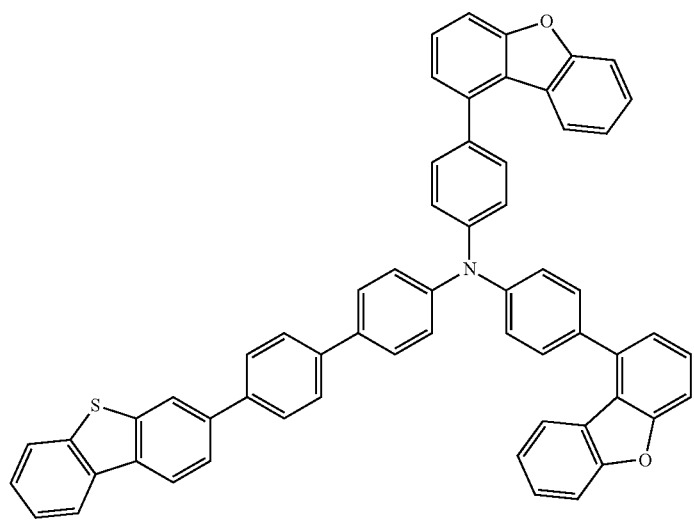
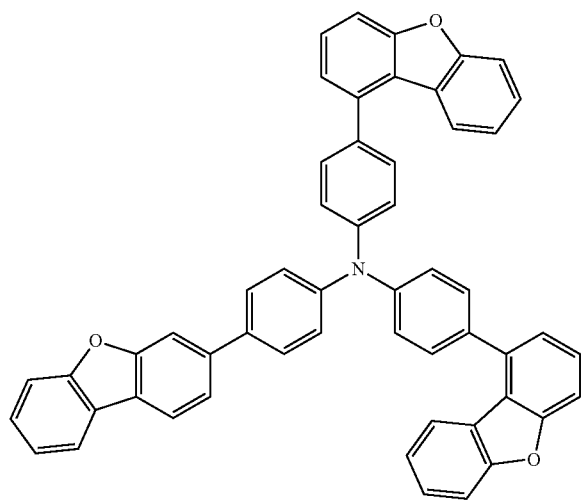

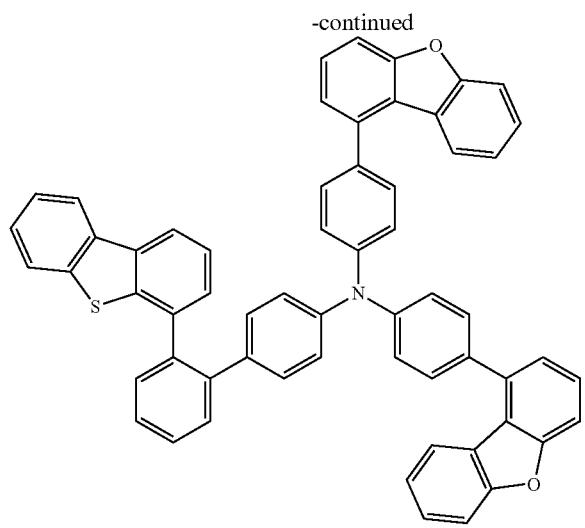
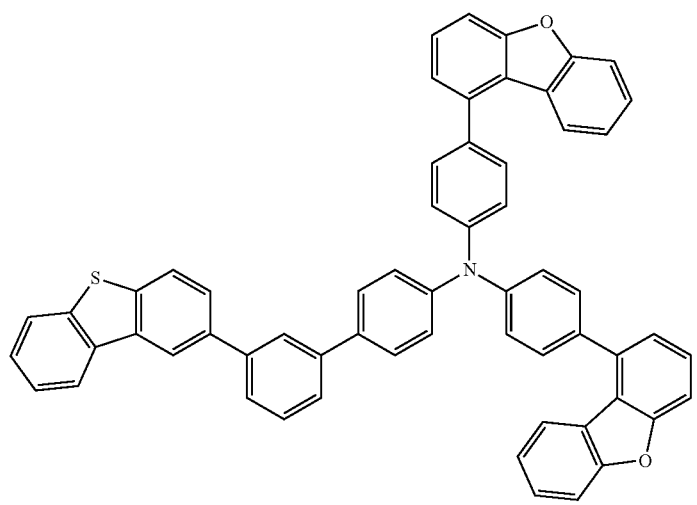
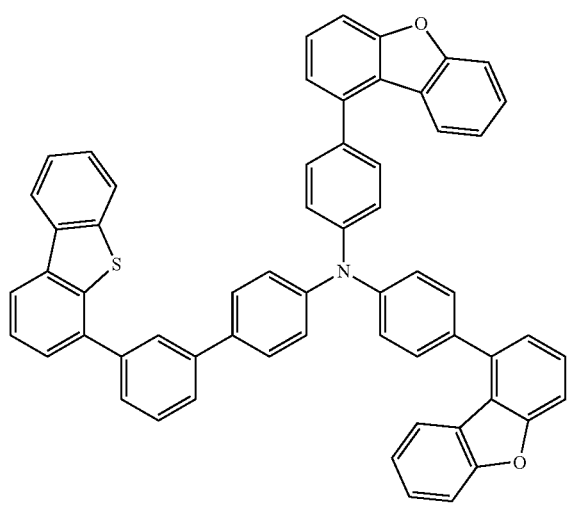

-continued
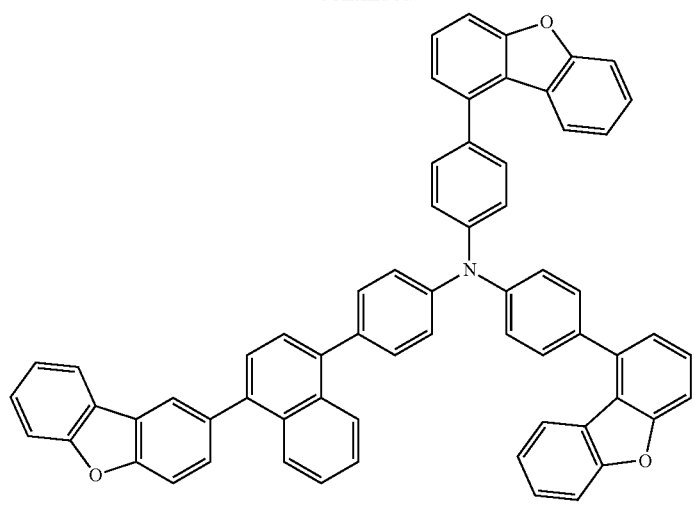
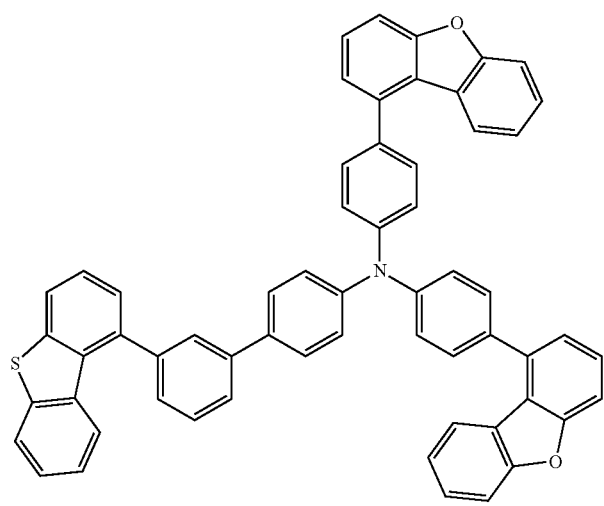
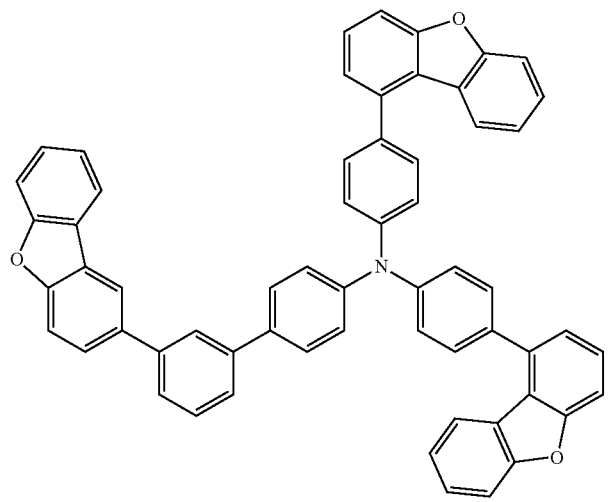

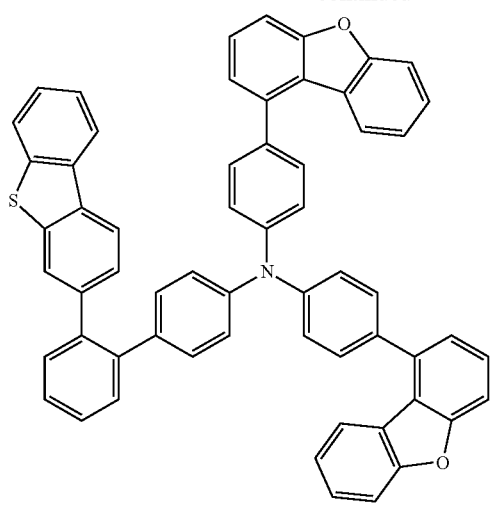
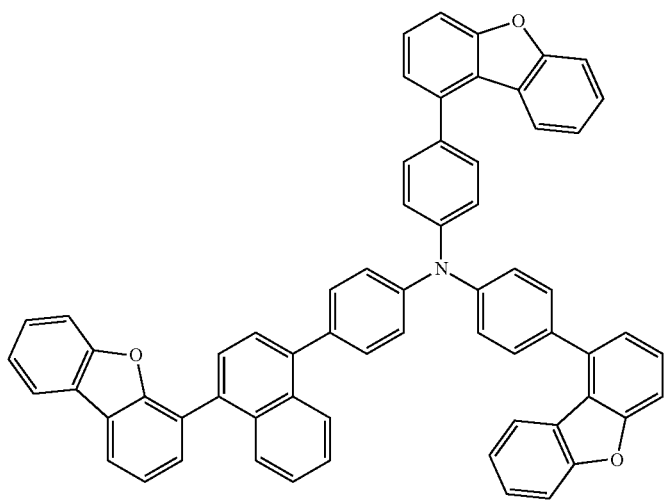
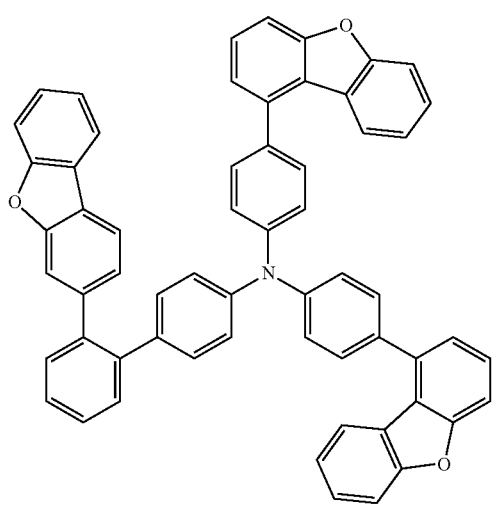

-continued
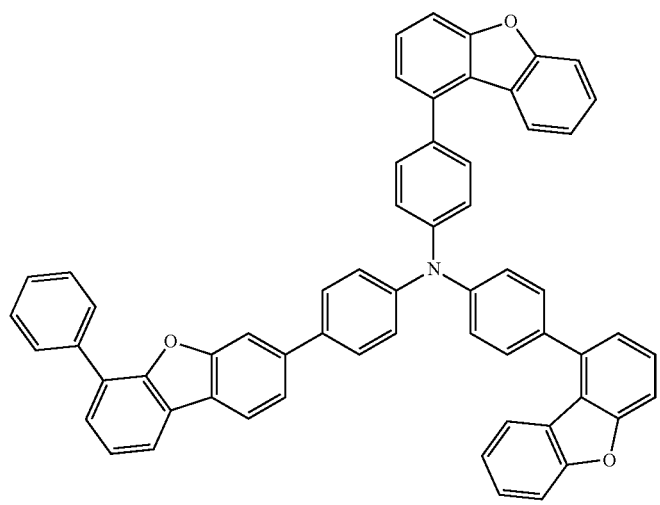
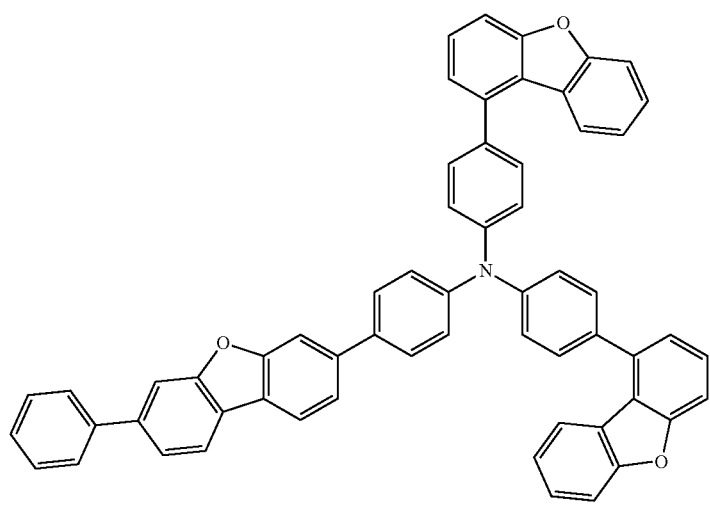
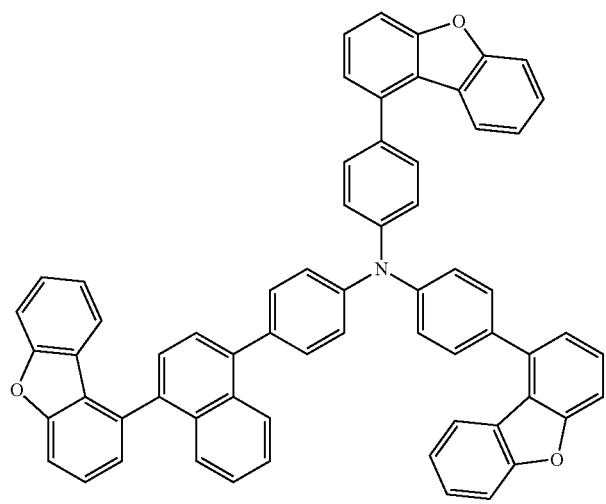

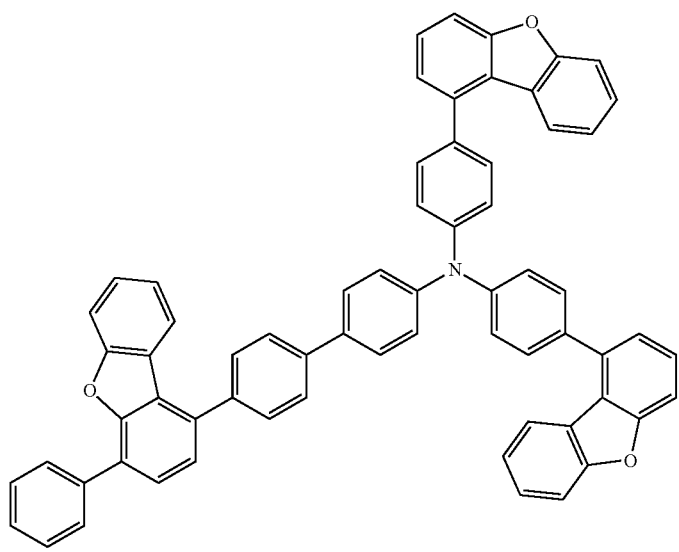
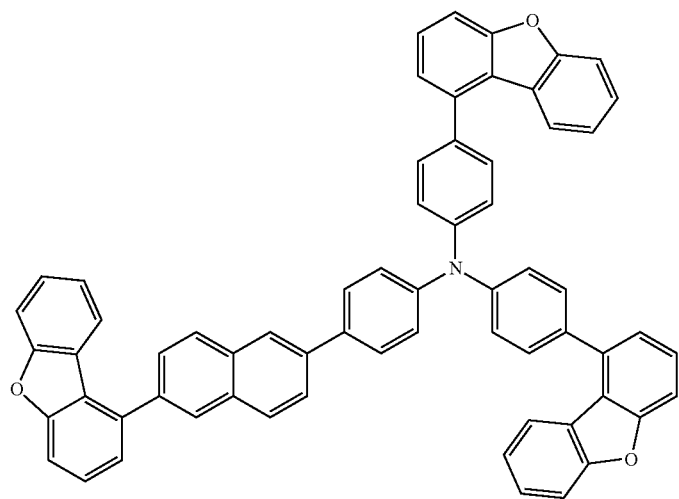
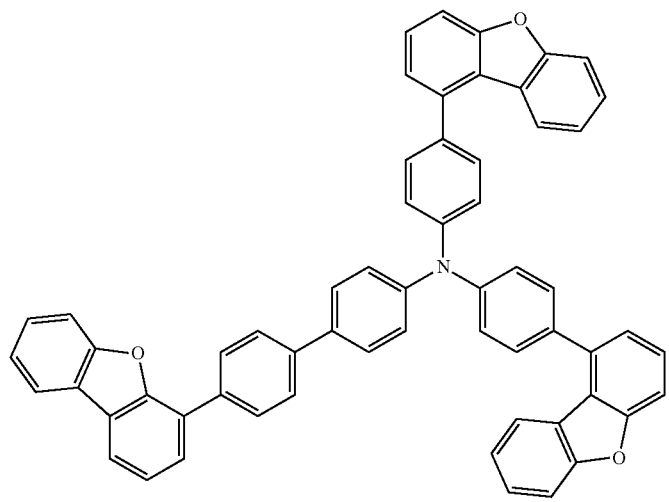

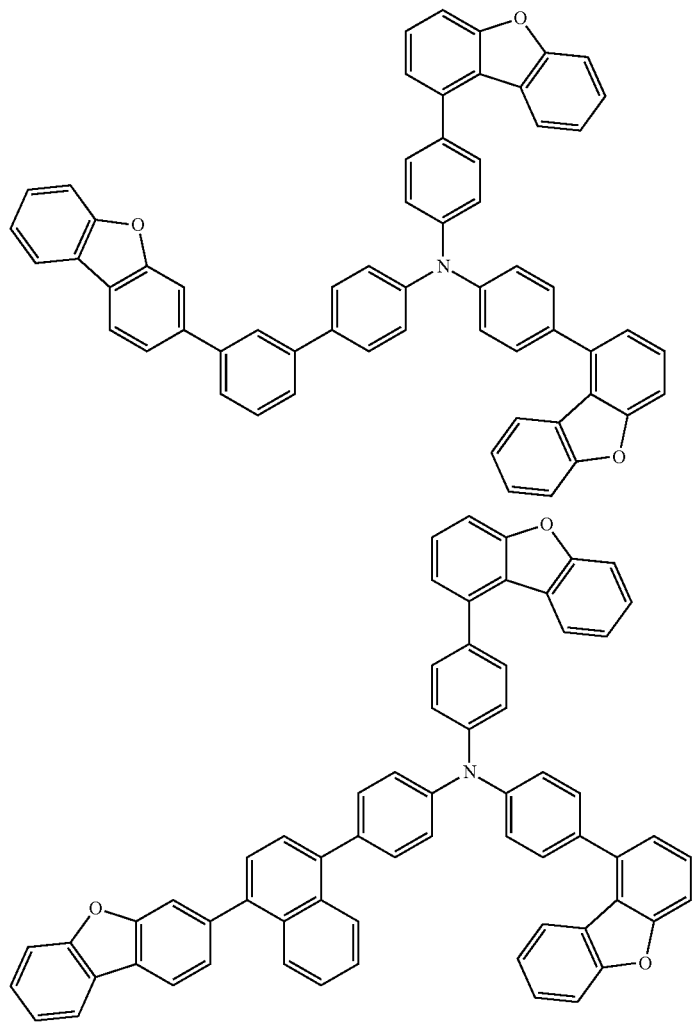
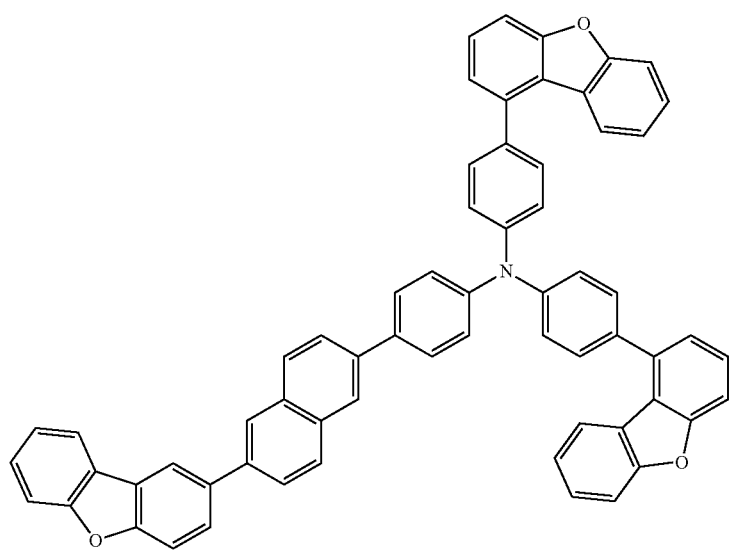

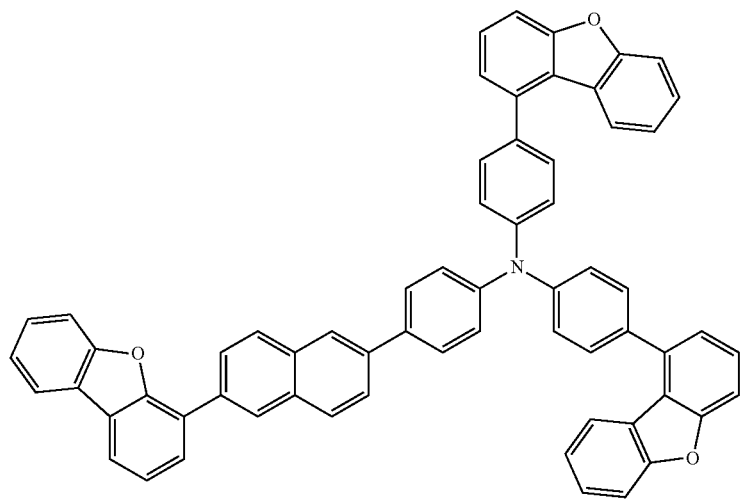
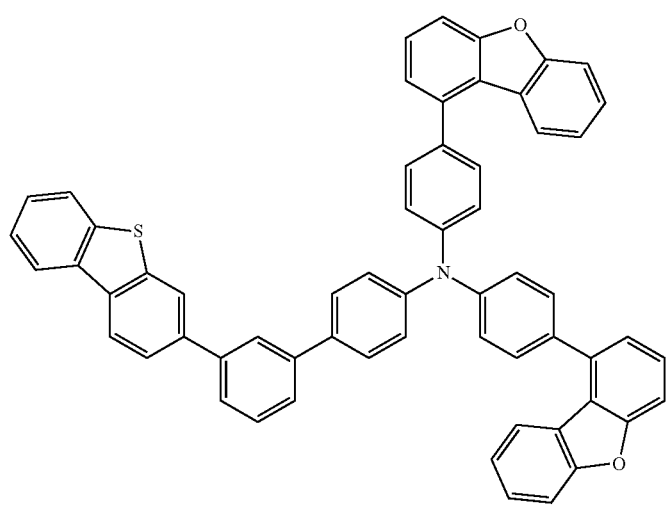
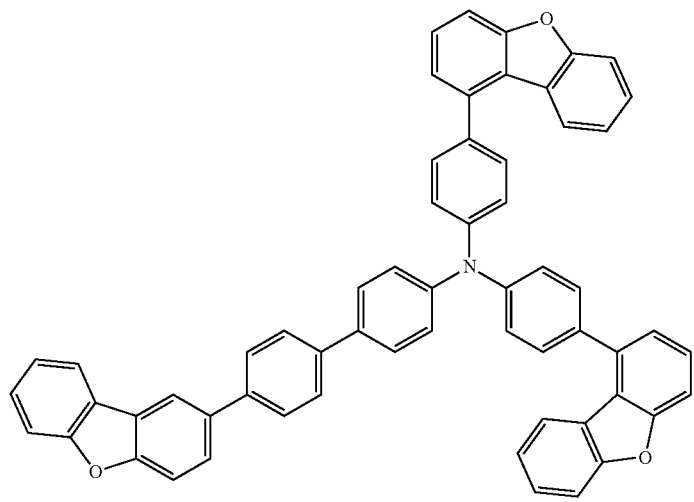

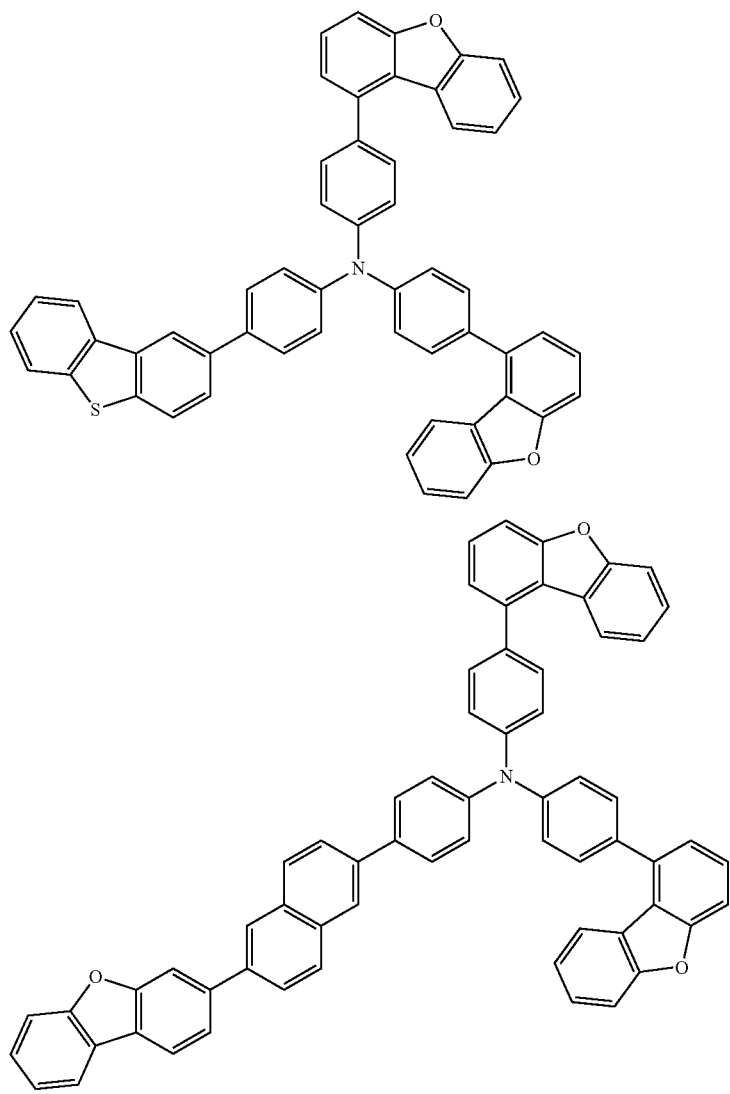
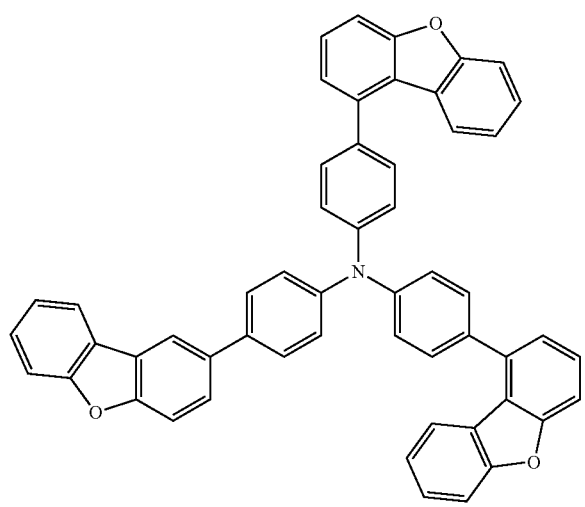

-continued
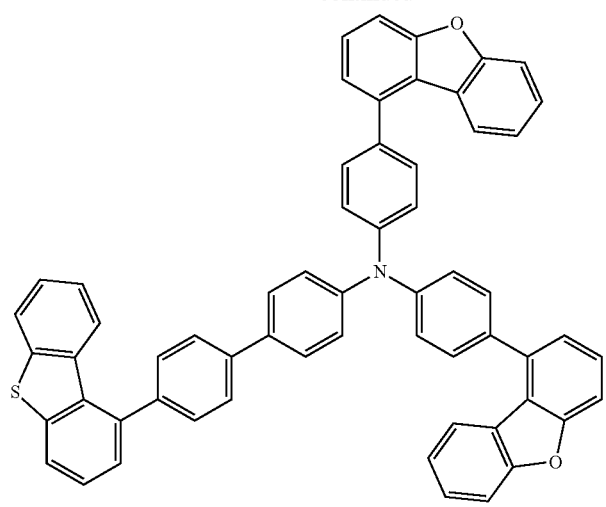
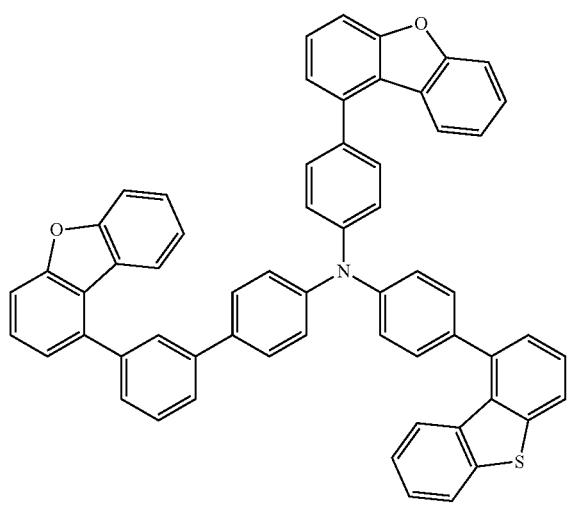
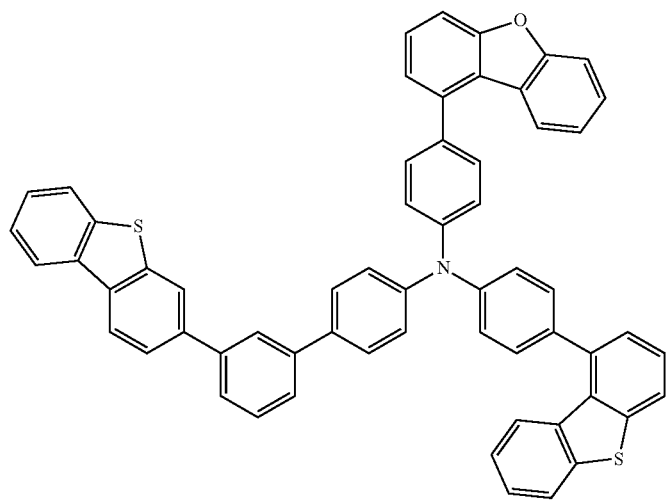

-continued
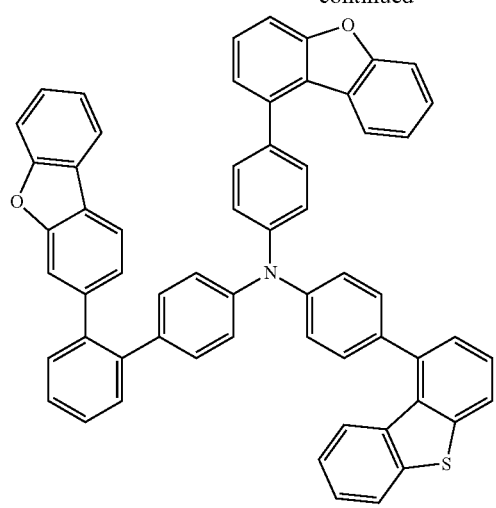
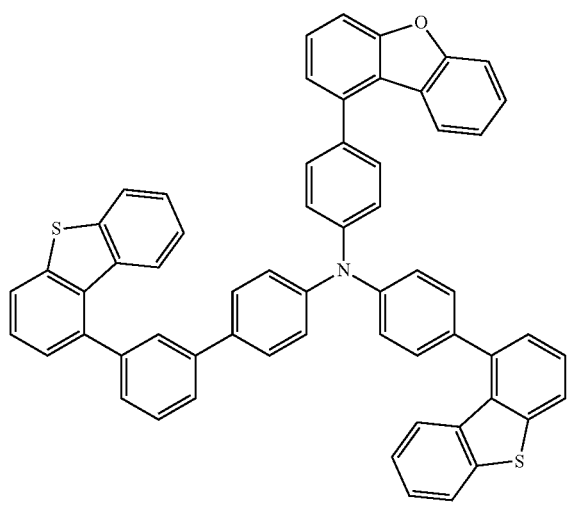
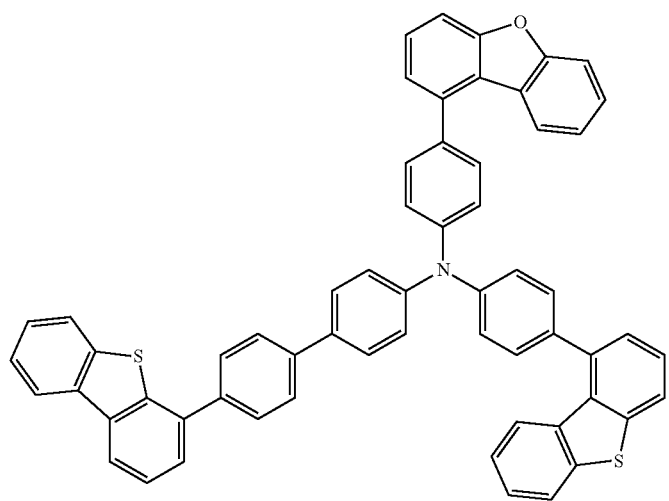

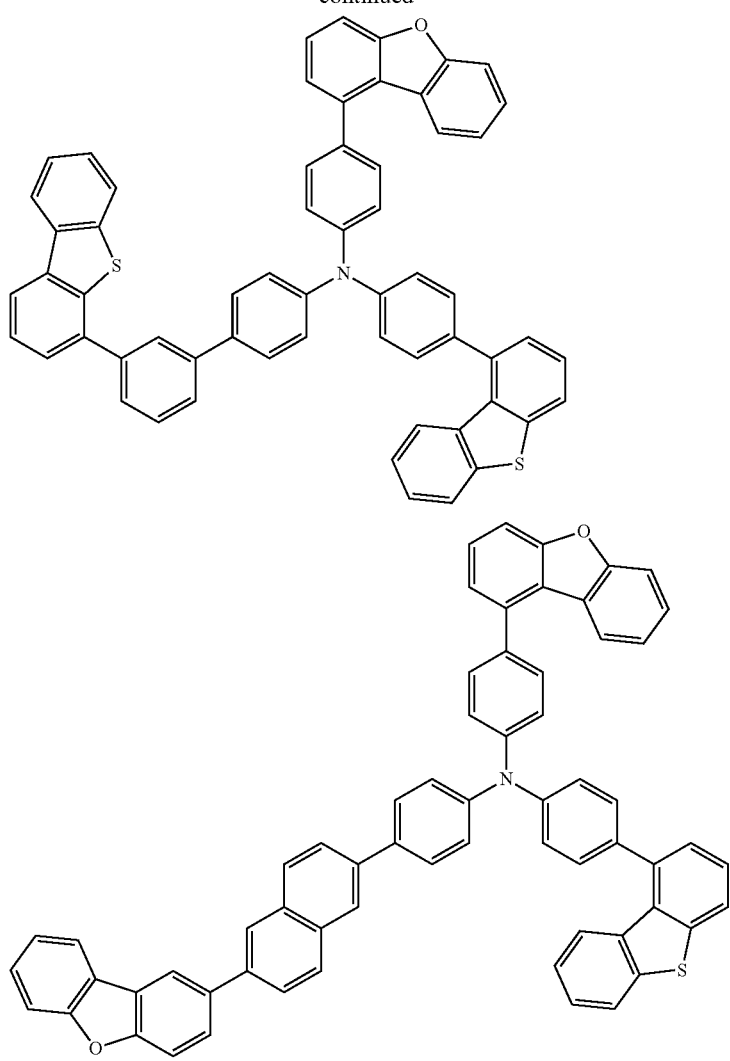
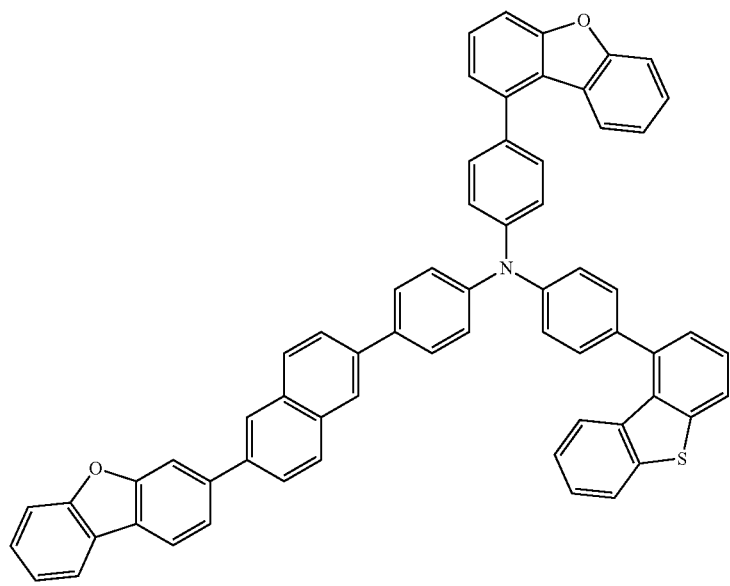

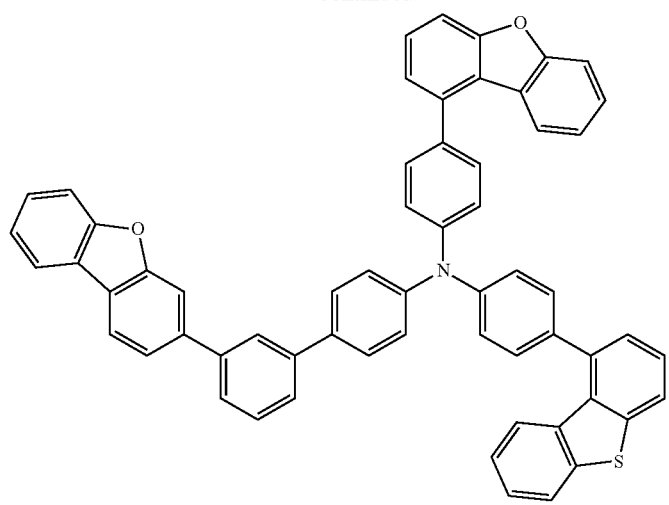
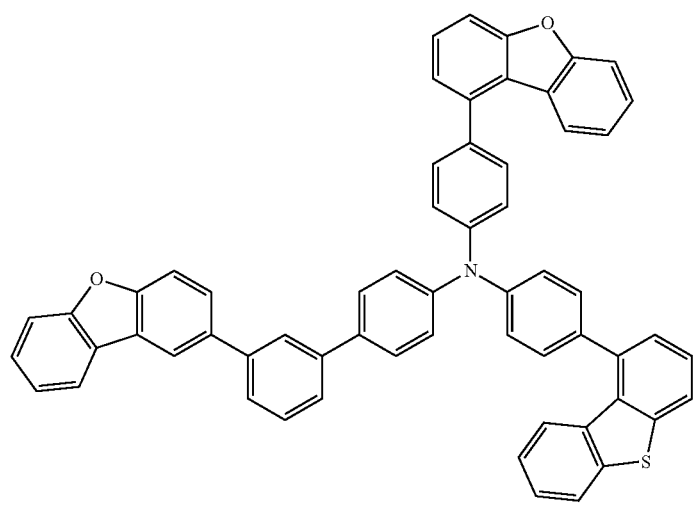
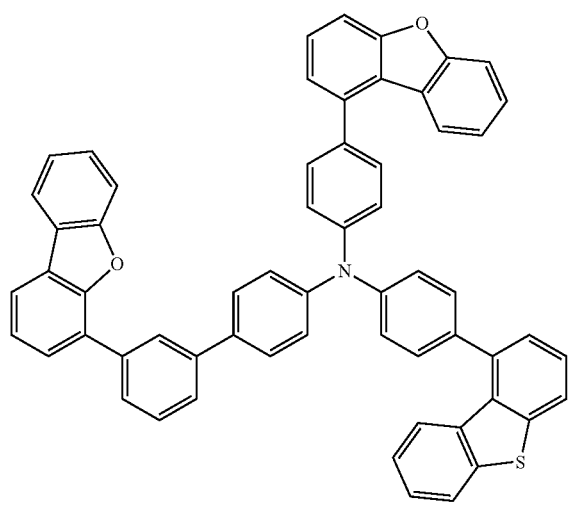

-continued
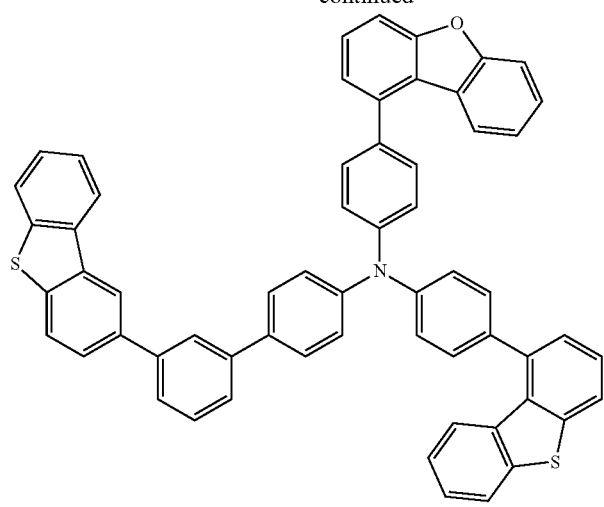
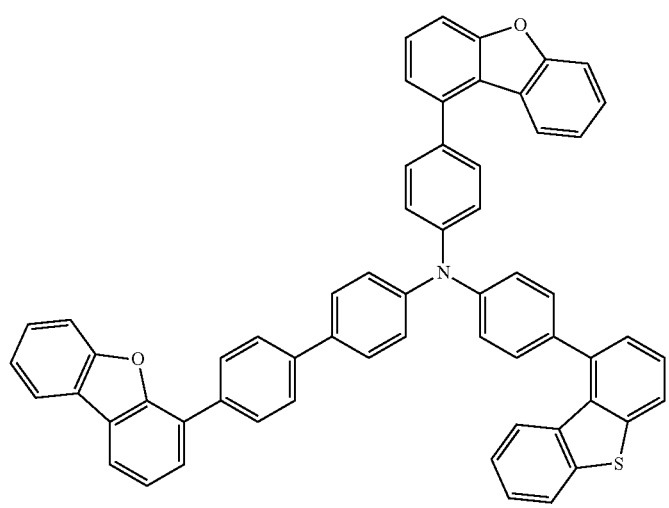
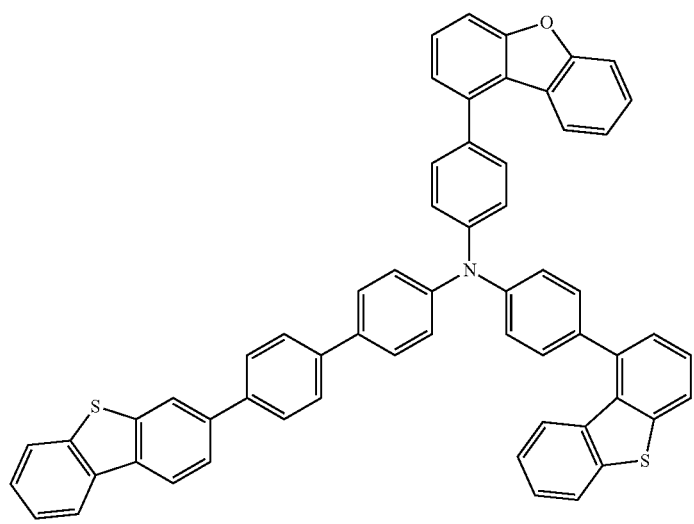

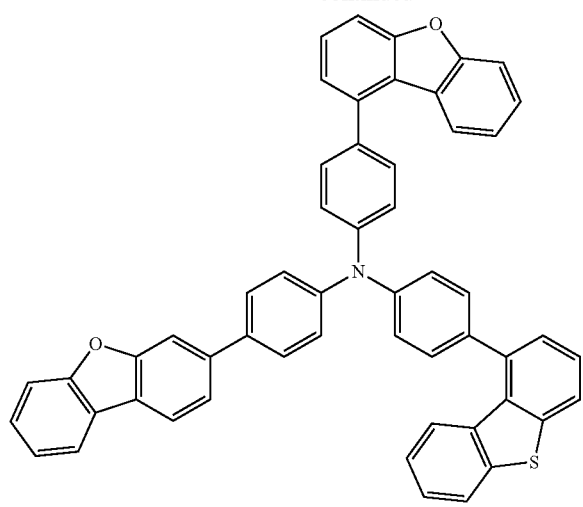
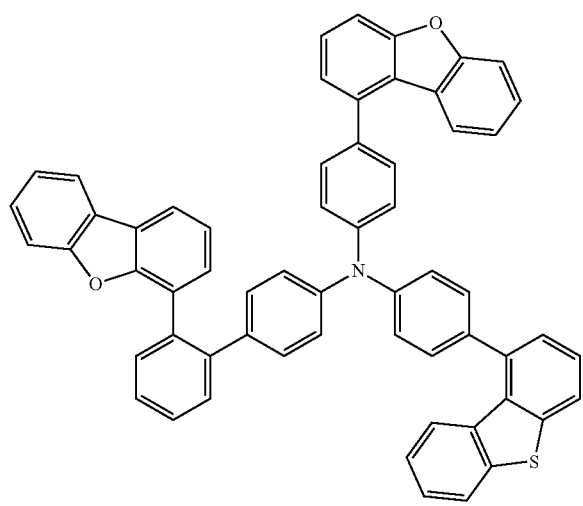
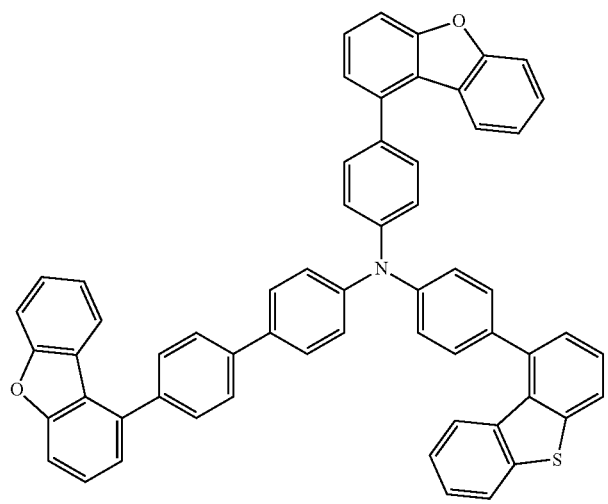

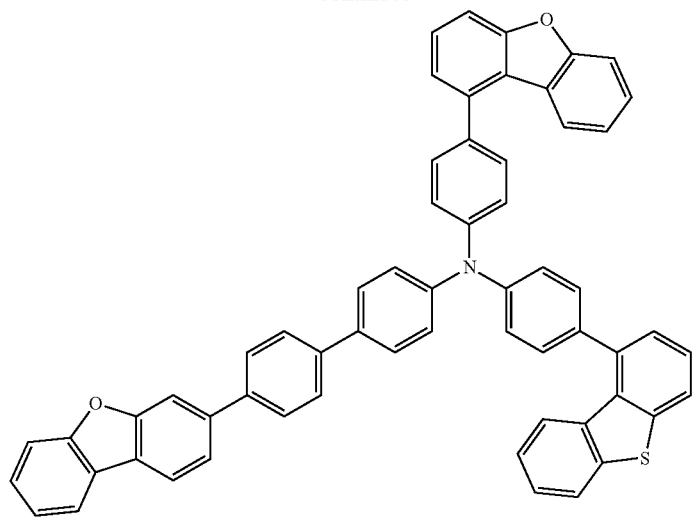
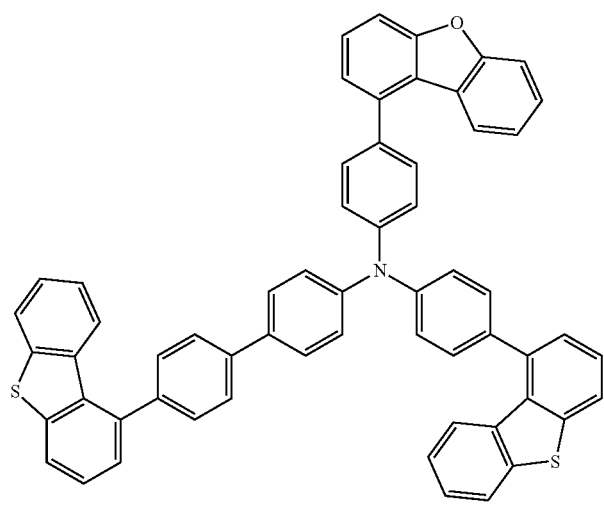
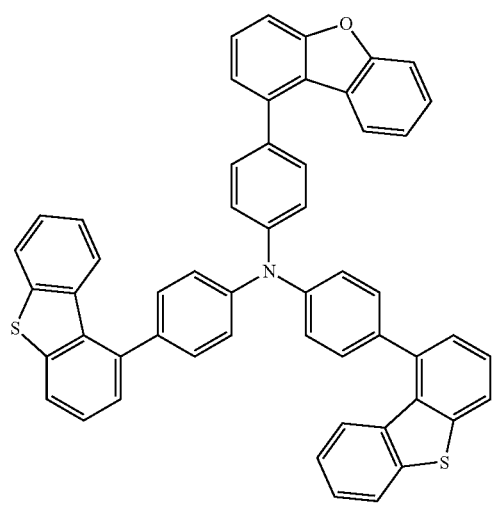

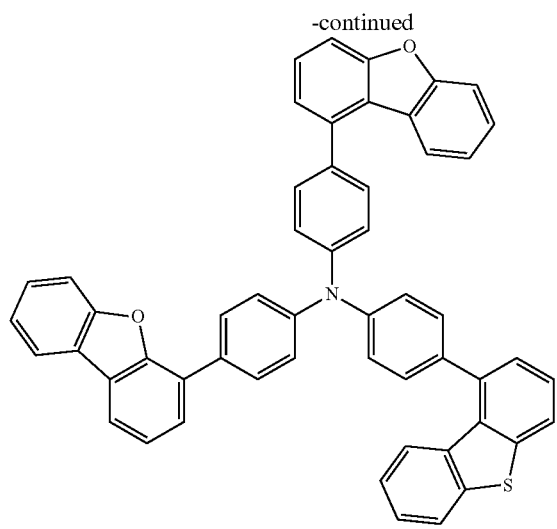
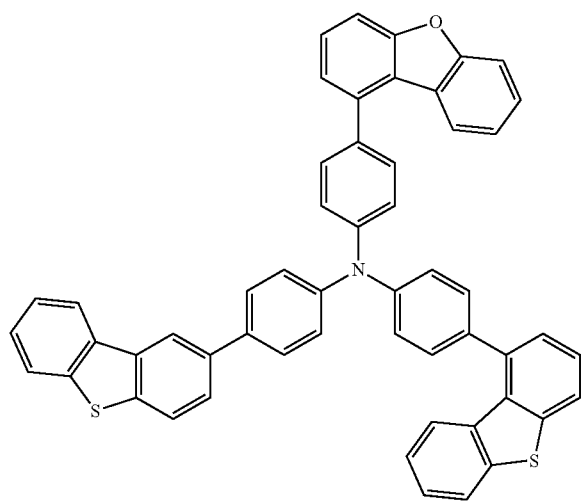
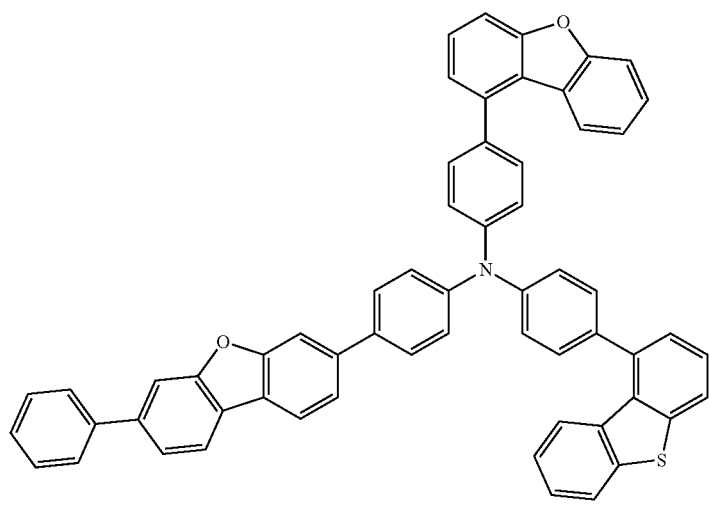

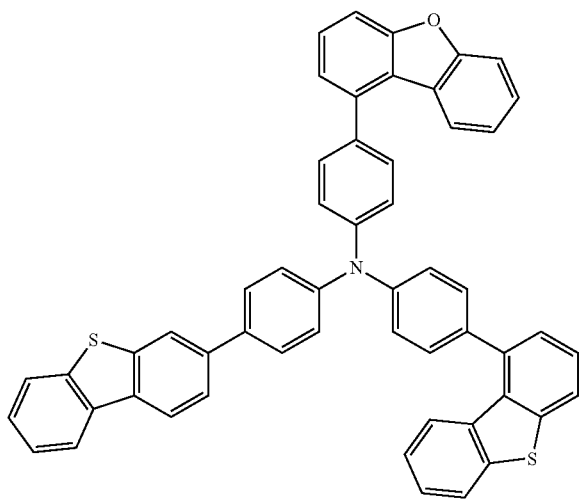
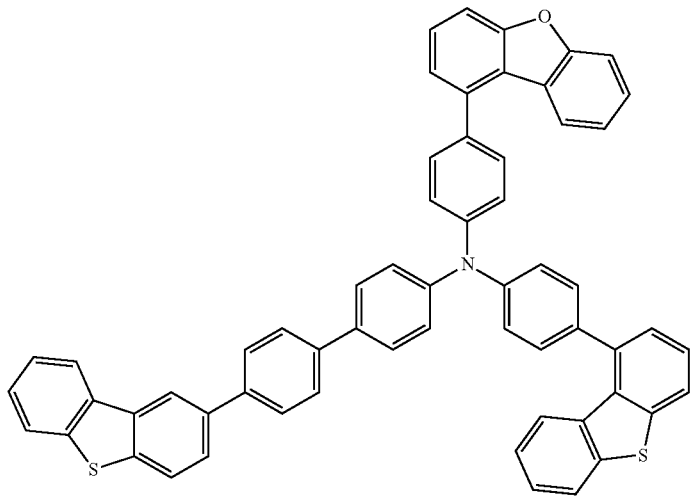
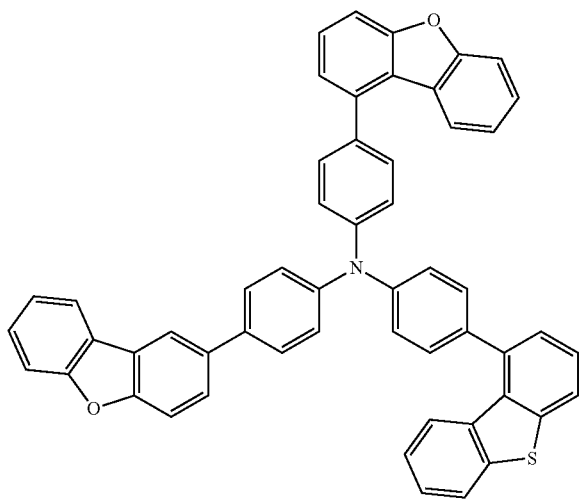

-continued
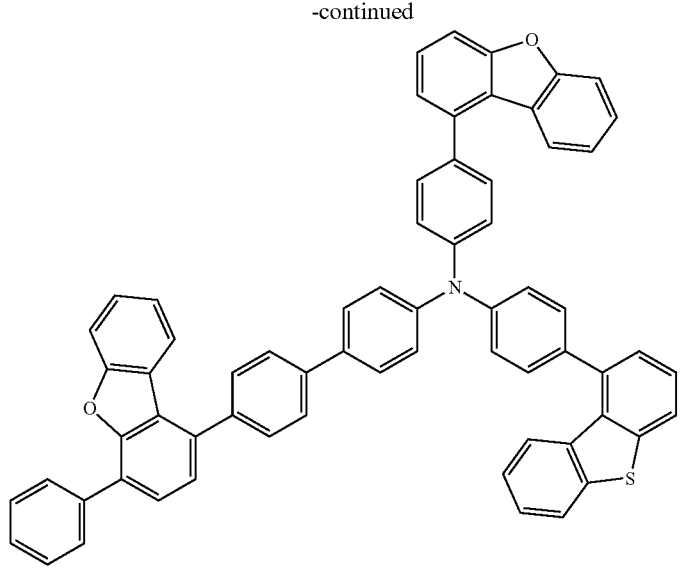
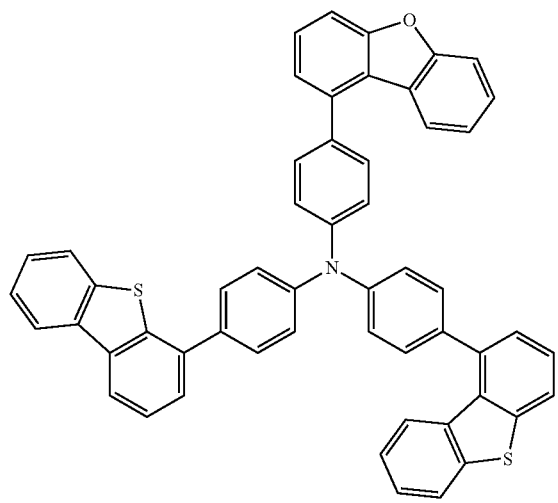
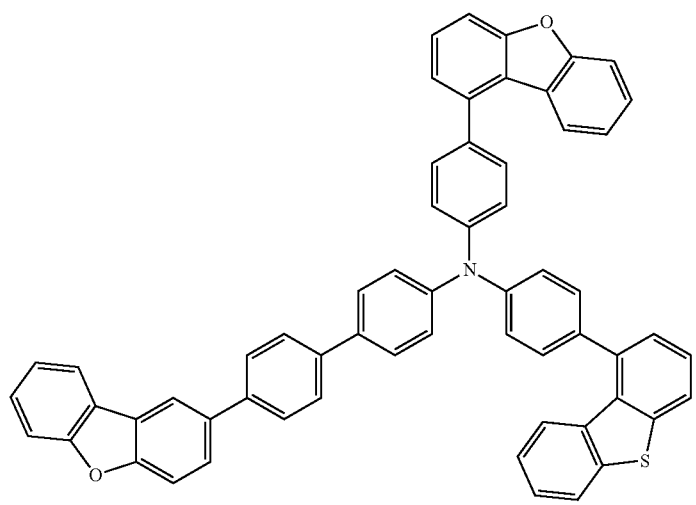

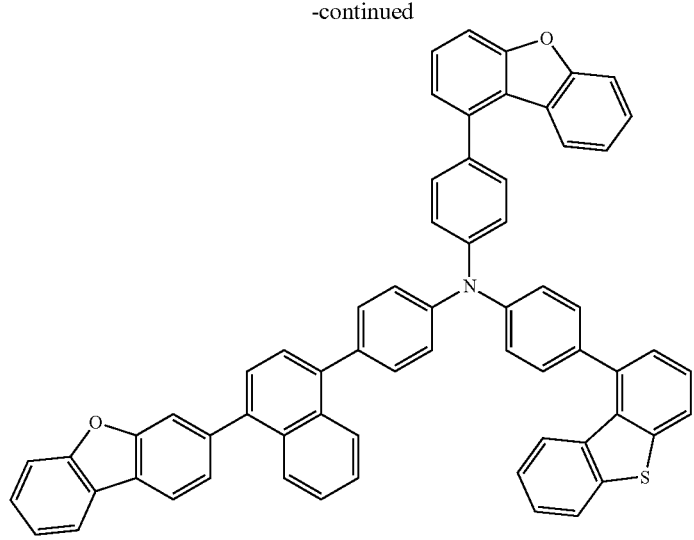
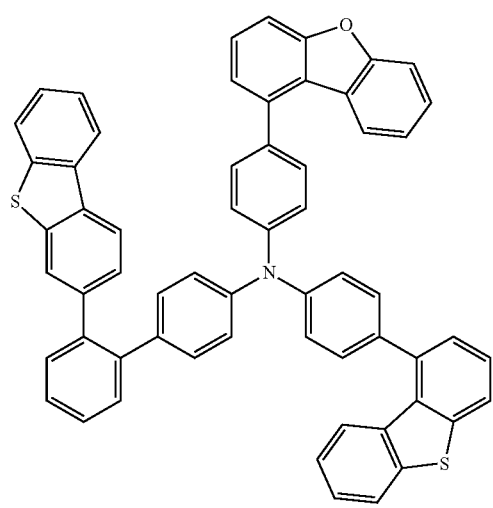
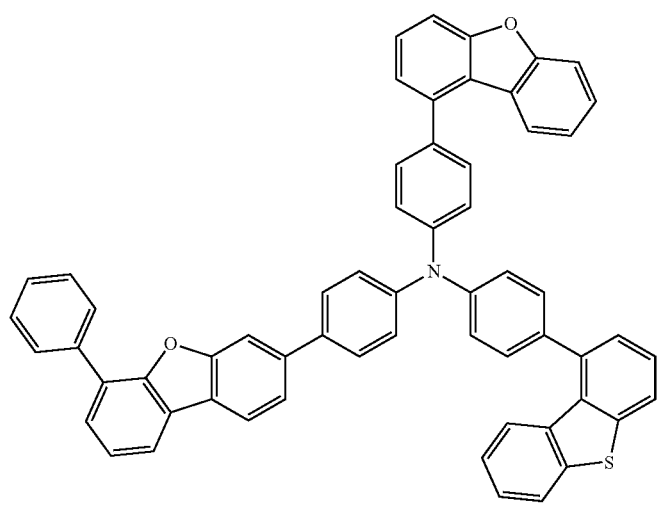

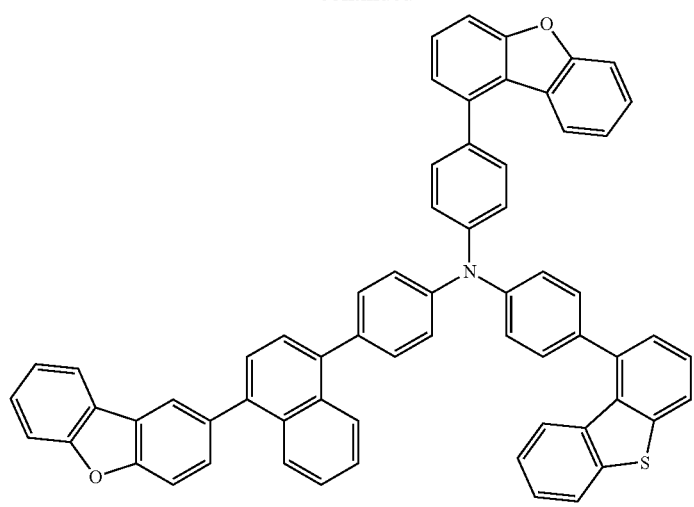
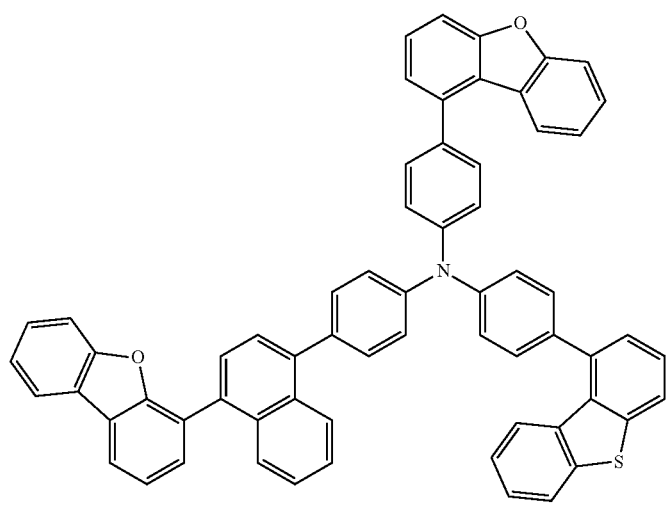
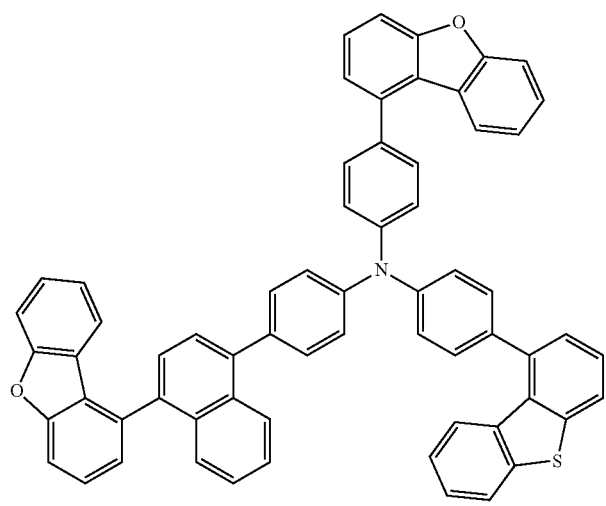

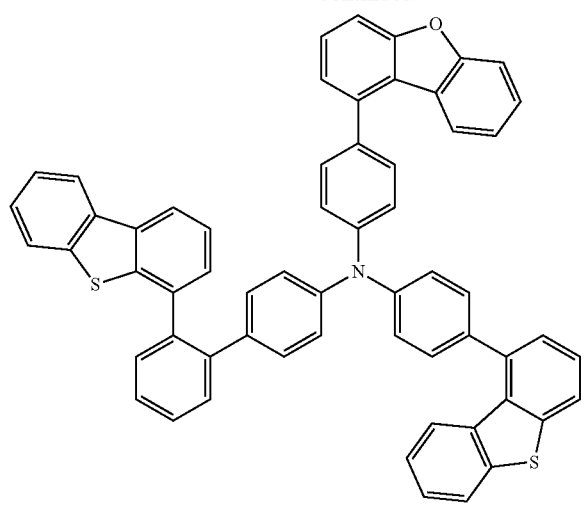
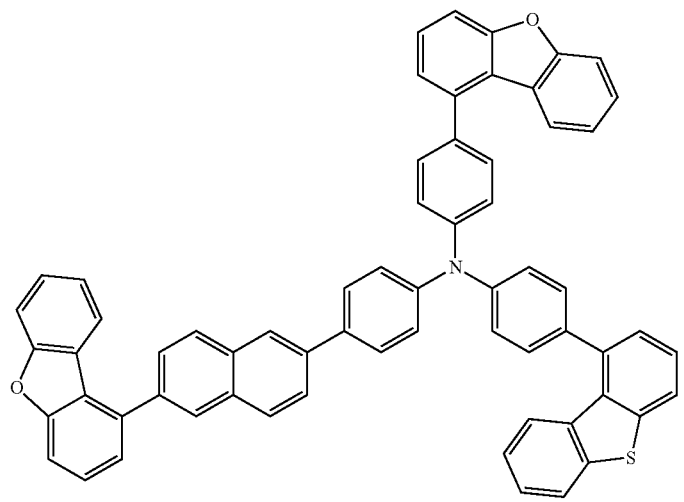
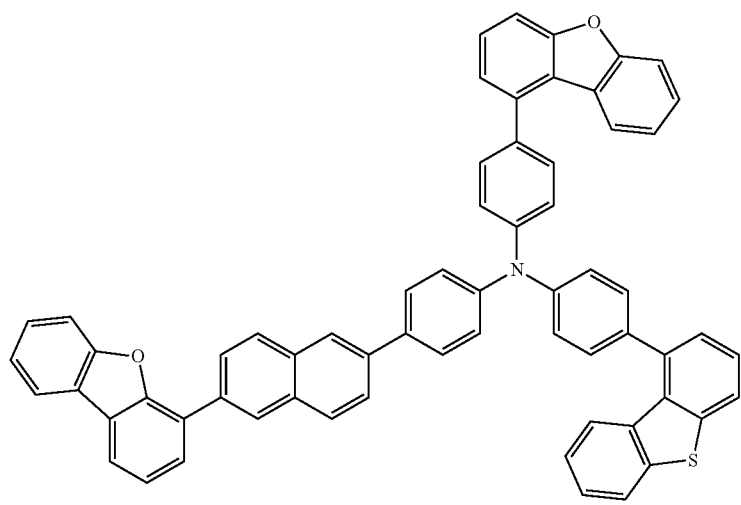

-continued
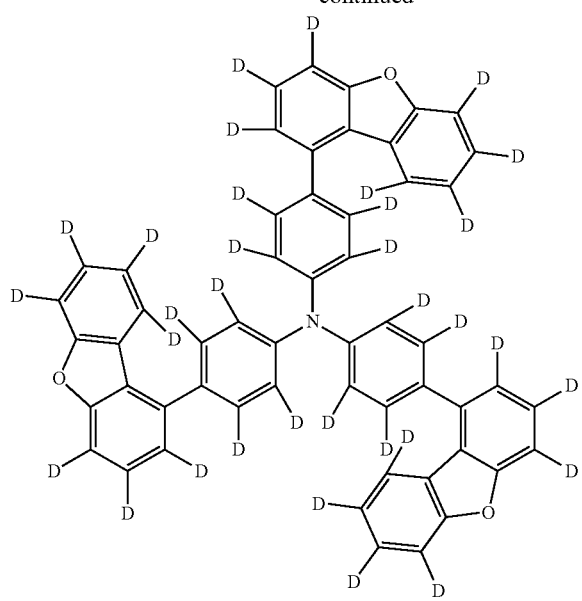
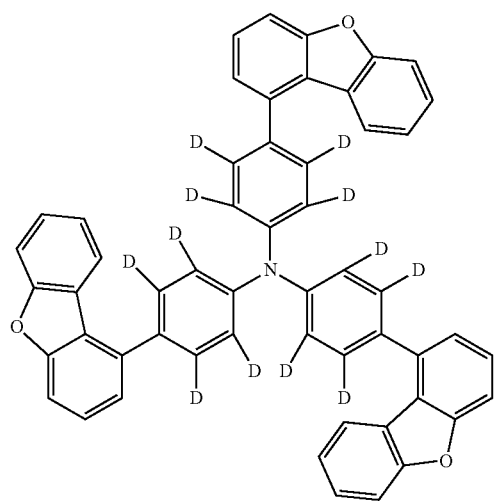
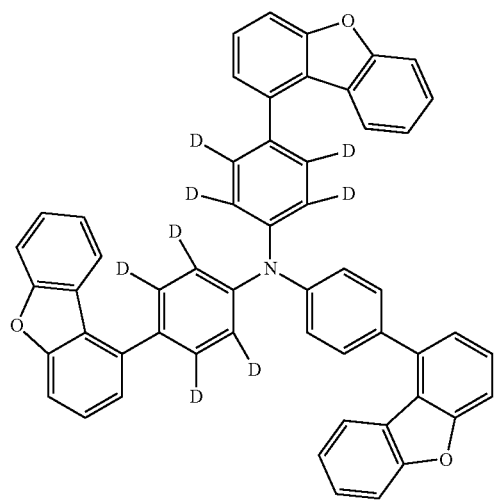

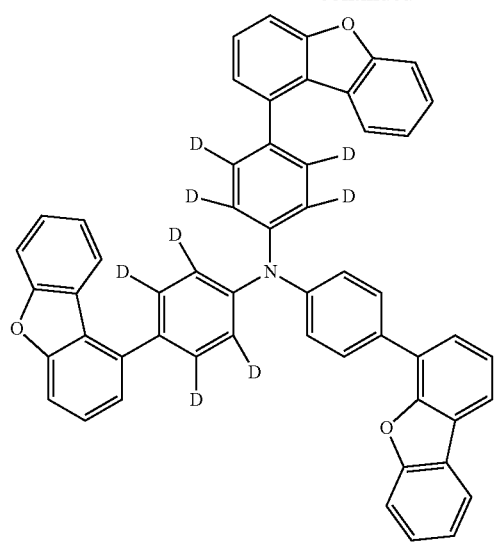
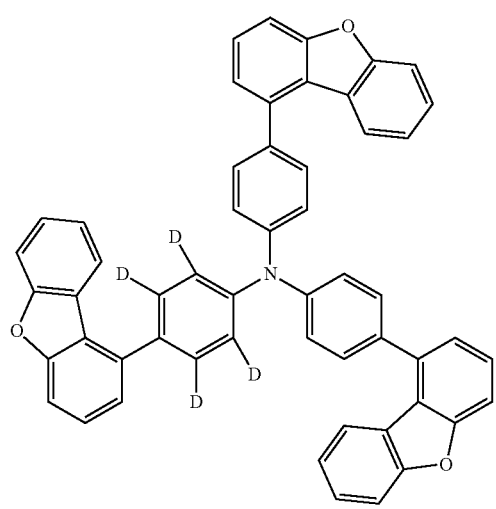
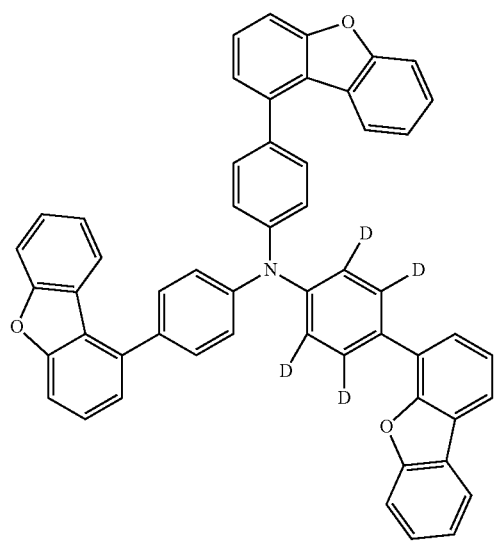

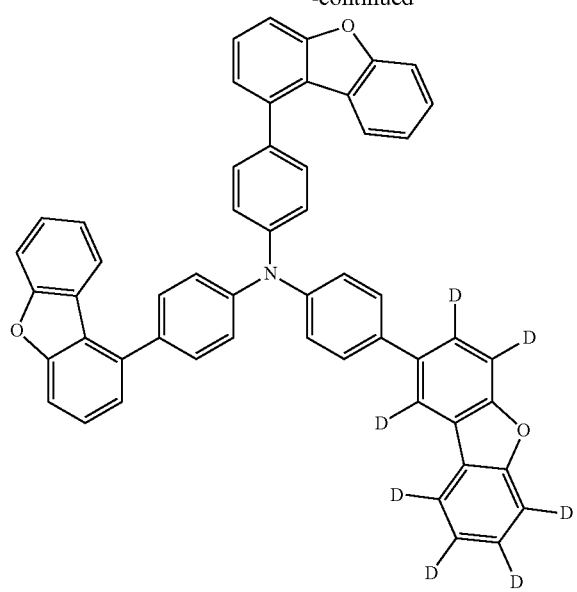
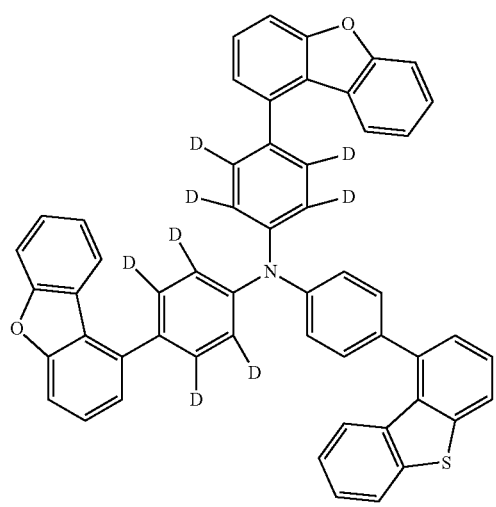
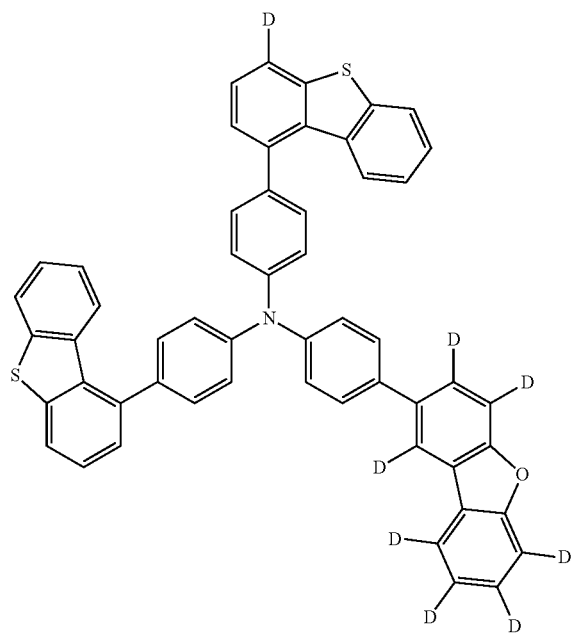

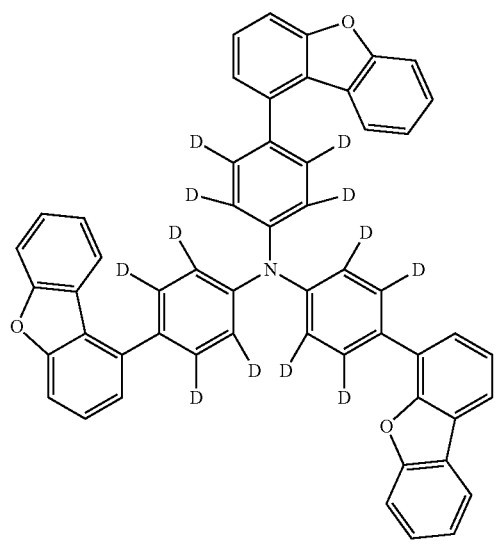
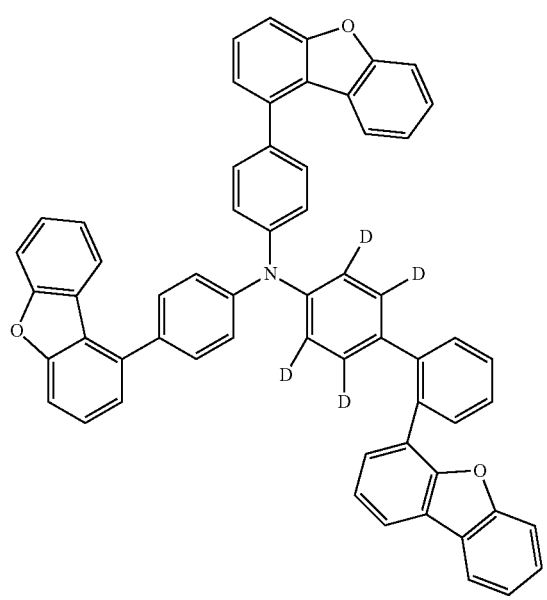

-continued

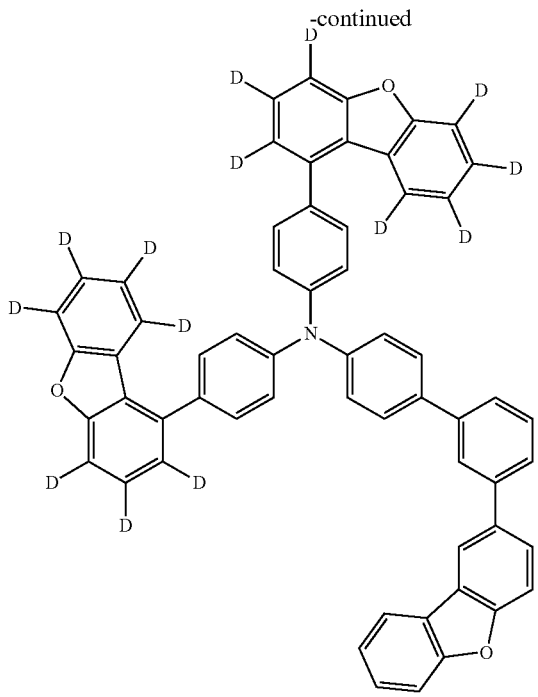

Material for Organic EL Devices

The material for organic electroluminescent devices contains the compound of the present invention. The content of the compound of the present invention in the material for organic electroluminescent devices is 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic electroluminescent devices is useful for the production of organic EL devices.

Organic EL Device

The organic EL device of the invention includes an anode, a cathode, and an organic layer disposed between the anode and the cathode. The organic layer includes a light emitting layer and at least one layer of the organic layer contains the compound of the present invention.

Examples of the organic layer which contains the compound of the present invention include a hole transporting region formed between an anode and a light emitting layer, such as a hole injecting layer, a hole transporting layer, an electron blocking layer, and an exciton blocking layer, a light emitting layer, a space layer, and an electron transporting region formed between a cathode and a light emitting layer, such as an electron injecting layer, an electron transporting layer, and a hole blocking layer, although not limited thereto. The compound of the present invention is used for the production of a fluorescent or phosphorescent EL device preferably as a material for a hole transporting region or a light emitting layer, more preferably as a material for a hole transporting region, still more preferably as a material for a hole transporting layer, an electron blocking layer or an exciton blocking layer, and particularly preferably as a material for an electron blocking layer or an exciton blocking layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to in this description is the smallest unit for emitting light by the recombination of injected holes and injected electrons, which includes an organic layer, wherein at least one layer is a light emitting layer.

Representative device structures of the simple-type organic EL device are shown below:

(1) Anode/Emission Unit/Cathode

The emission unit may be a multi-layered structure including two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer/Electron transporting layer(/Electron injecting layer);

(b) (Hole injecting layer/)Hole transporting layer/Phosphorescent emitting layer/Electron transporting layer(/Electron injecting layer);

(c) (Hole injecting layer/)Hole transporting layer/First fluorescent emitting layer/Second fluorescent emitting layer/Electron transporting layer(/Electron injecting layer);

(d) (Hole injecting layer/)Hole transporting layer/First phosphorescent emitting layer/Second phosphorescent emitting layer/Electron transporting layer(/Electron injecting layer);

(e) (Hole injecting layer/)Hole transporting layer/Phosphorescent emitting layer/Space layer/Fluorescent emitting layer/Electron transporting layer(/Electron injecting layer);

(f) (Hole injecting layer/)Hole transporting layer/First phosphorescent emitting layer/Second phosphorescent emitting layer/Space layer/Fluorescent emitting layer/Electron transporting layer(/Electron injecting layer);

(g) (Hole injecting layer/)Hole transporting layer/First phosphorescent emitting layer/Space layer/Second phosphorescent emitting layer/Space layer/Fluorescent emitting layer/Electron transporting layer(/Electron injecting layer);

(h) (Hole injecting layer/)Hole transporting layer/Phosphorescent emitting layer/Space layer/First fluorescent emitting layer/Second fluorescent emitting layer/Electron transporting layer(/Electron injecting layer);

(i) (Hole injecting layer/)Hole transporting layer/Electron blocking layer/Fluorescent emitting layer/Electron transporting layer(/Electron injecting layer);

(j) (Hole injecting layer/)Hole transporting layer/Electron blocking layer/Phosphorescent emitting layer/Electron transporting layer(/Electron injecting layer);

(k) (Hole injecting layer/)Hole transporting layer/Exciton blocking layer/Fluorescent emitting layer/Electron transporting layer(/Electron injecting layer);

(l) (Hole injecting layer/)Hole transporting layer/Exciton blocking layer/Phosphorescent emitting layer/Electron transporting layer(/Electron injecting layer);

(m) (Hole injecting layer/)First hole transporting layer/Second hole transporting layer/Fluorescent emitting layer/Electron transporting layer(/Electron injecting layer);

(n) (Hole injecting layer/)First hole transporting layer/Second hole transporting layer/Phosphorescent emitting layer/Electron transporting layer(/Electron injecting layer);

(o) (Hole injecting layer/)First hole transporting layer/Second hole transporting layer/Fluorescent emitting layer/First electron transporting layer/Second electron transporting layer(/Electron injecting layer);

(p) (Hole injecting layer/)First hole transporting layer/Second hole transporting layer/Phosphorescent emitting layer/First electron transporting layer/Second electron transporting layer(/Electron injecting layer);

(q) (Hole injecting layer/)Hole transporting layer/Fluorescent emitting layer/Hole blocking layer/Electron transporting layer(/Electron injecting layer);

(r) (Hole injecting layer/)Hole transporting layer/Phosphorescent emitting layer/Hole blocking layer/Electron transporting layer(/Electron injecting layer);

(s) (Hole injecting layer/)Hole transporting layer/Fluorescent emitting layer/Exciton blocking layer/Electron transporting layer(/Electron injecting layer); and (t) (Hole injecting layer/)Hole transporting layer/Phosphorescent emitting layer/Exciton blocking layer/Electron transporting layer(/Electron injecting layer).

The emission colors of phosphorescent emitting layers or fluorescent emitting layers may be different. For example, the layered structure of the emission unit (f) may be (Hole injecting layer)/Hole transporting layer/First phosphorescent emitting layer (red emission)/Second phosphorescent emitting layer (green emission)/Sp ace layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may use a known material configuration in which electrons are supplied to the first emission unit and holes are supplied to the second emission unit.

FIG. 1 is a schematic illustration showing the structure of an example of the organic EL device of the invention, wherein an organic EL device 1 includes a substrate 2, an anode 3, a cathode 4, and an emission unit 10 disposed between the anode 3 and the cathode 4. The emission unit 10 includes a light emitting layer 5. A hole transporting region 6 (for example, a hole injecting layer or a hole transporting layer) is disposed between the light emitting layer 5 and the anode 3, and an electron transporting region 7 (for example, an electron injecting layer or an electron transporting layer) is disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
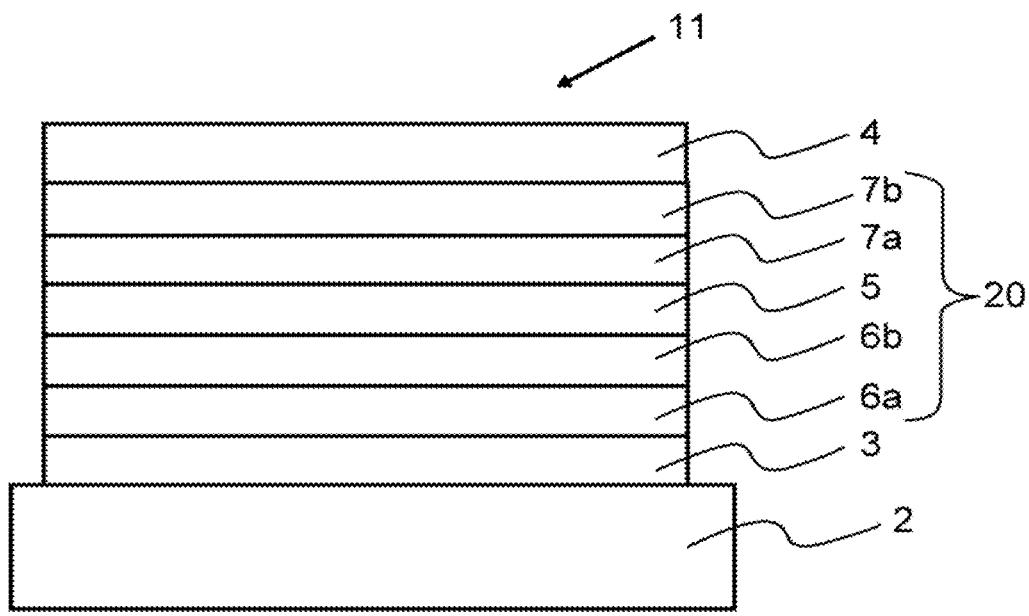
FIG. 2 is a schematic view showing another example of a layered configuration of an organic EL device of an embodiment of the invention.

FIG. 2 is a schematic illustration showing the structure of another example of the organic EL device of the present invention, wherein an organic EL device 11 includes a substrate 2, an anode 3, a cathode 4, and an emission unit 20 disposed between the anode 3 and the cathode 5. The emission unit 20 includes a light emitting layer 4. The hole transporting region disposed between the anode 3 and the light emitting layer 5 is formed by a first hole transporting layer 6a and a second hole transporting layer 6b. The electron transporting region disposed between the light emitting layer 5 and the cathode 4 is formed by a first electron transporting layer 7a and a second electron transporting layer 7b.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the organic EL device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode formed on the substrate is preferably made from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally used as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium (Eu) and ytterbium (Yb), and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer contains a material having a high hole injecting ability (hole injecting material) and formed between an anode and a light emitting layer or between an anode and a hole transporting layer, if present.

The hole injecting material includes molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following aromatic amine compounds, which are a low-molecular organic compound, are also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). A macromolecular compound doped with an acid, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used:

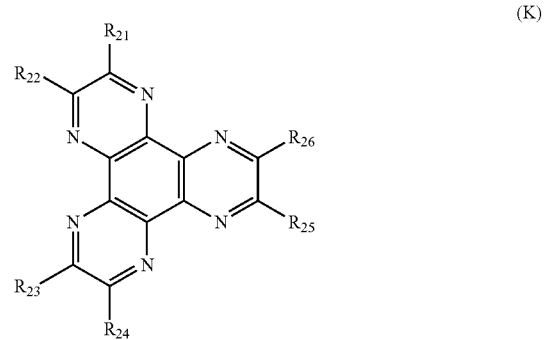

(K)

wherein:

$R_{21}$ to $R_{26}$ are each independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material) and formed between an anode and a light emitting layer or between a hole injecting layer, if present, and a light emitting layer. The compound of the present invention is preferably used in a hole transporting layer alone or in combination with the compound described below.

The hole transporting layer may be a single layer or a multi-layer of two or more layers. For example, the hole transporting layer may be a two-layered structure comprising a first hole transporting layer (anode side) and a second hole transporting layer (cathode side). In an embodiment of the invention, a hole transporting layer of a single-layered structure is preferably in contact with a light emitting layer and a hole transporting layer in a multi-layered structure which is closest to a cathode, for example, the second hole transporting layer in the two-layered structure mentioned above, is preferably in contact with a light emitting layer. In another embodiment of the invention, an electron blocking layer mentioned below may be disposed between the light emitting layer and the hole transporting layer of the single-layered structure or between the light emitting layer and the hole transporting layer in the multi-layered structure which is closest to the light emitting layer.

In the two-layered structure of the hole transporting layer, the compound of the present invention may be included in one or both of the first hole transporting layer and the second hole transporting layer.

In an embodiment of the invention, the compound of the present invention is preferably used only in the first hole transporting layer. In another embodiment, the compound of the present invention is preferably used only in the second hole transporting layer. In still another embodiment, the compound of the present invention is preferably used in both the first hole transporting layer and the second hole transporting layer.

Examples of the hole transporting material other than the compound of the present invention includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluorene-2-yl)-N-phenylamino]biphenyl (DFLDPBi), 4,4',4''-tris(N,N-diphenylamino)triphenylamine (TDATA), 4,4',4''-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ cm$^2$/Vs or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl)anthracene (t-BuDNA), 9,10-di(2-naphthyl) anthracene (DNA), and 9,10-diphenylanthracene (DPAnth).

In addition, a macromolecular compound, such as poly(N-vinylcarbazole) (PVK) and poly(4-vinyltriphenylamine) (PVTPA) are usable.

Compounds other than those mentioned above are also usable, if their hole transporting ability is higher than their electron transporting ability.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl) quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato) (monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoro acetonato](monophenanthroline) europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The host material preferably has a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a condensed aromatic compound, such as a carbazole derivative, an anthracene derivative, a phenanthrene derivative, a pyrene derivative, and a chrysene derivative; and (4) an aromatic amine compound, such as a triarylamine derivative and a condensed polycyclic aromatic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq2), bis(2-methyl-8-quinolinolato) (4-phenylphenolato)aluminum (III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a condensed aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl) anthracene (DPPA), 9,10-di(2-naphthyl) anthracene (DNA), 2-tert-butyl-9,10-di(2-naphthyl) anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-nanphthyl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

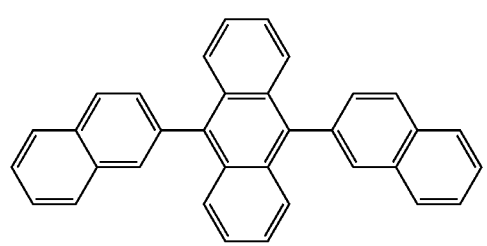

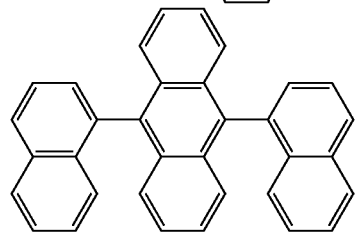

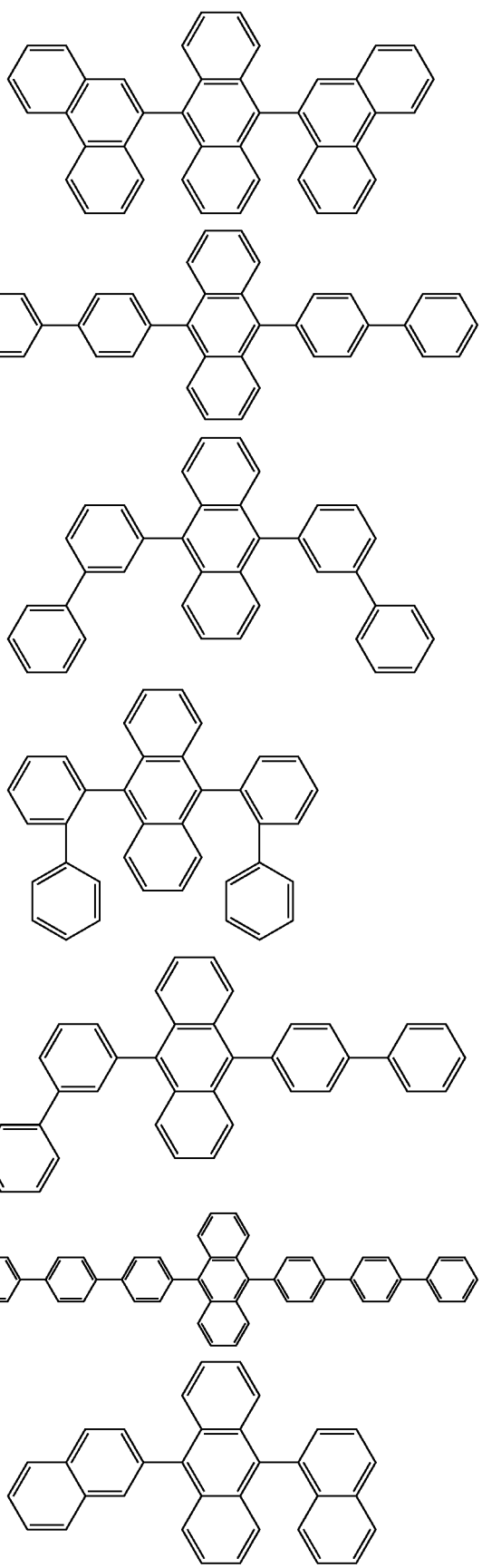

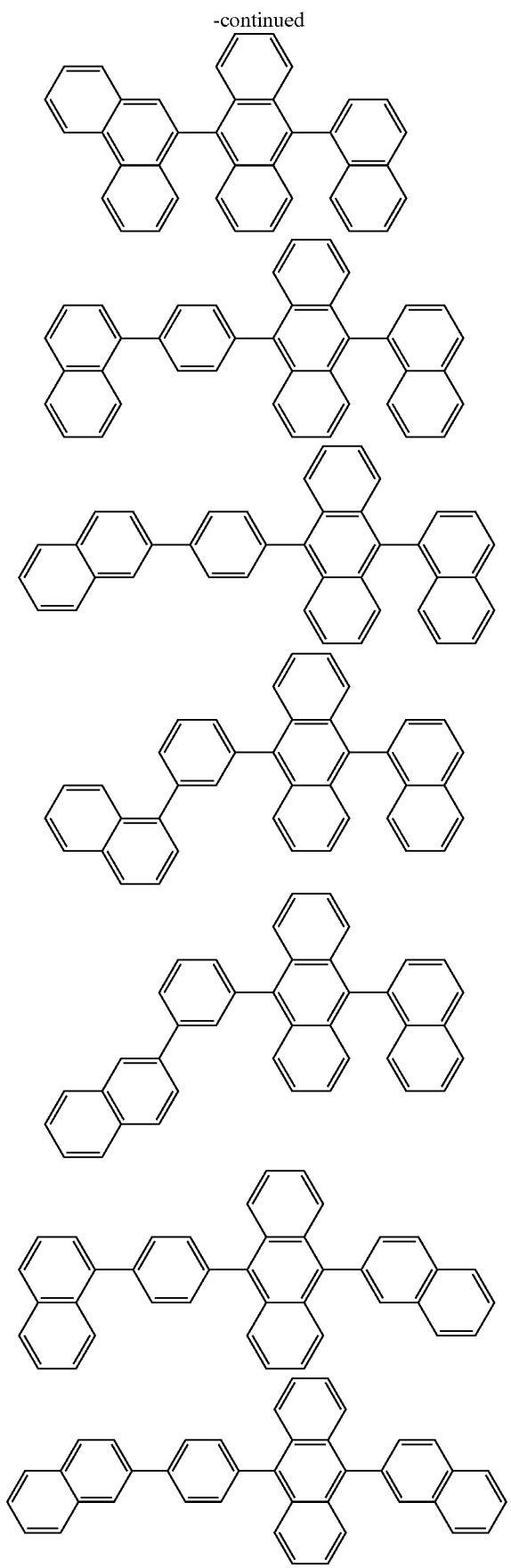
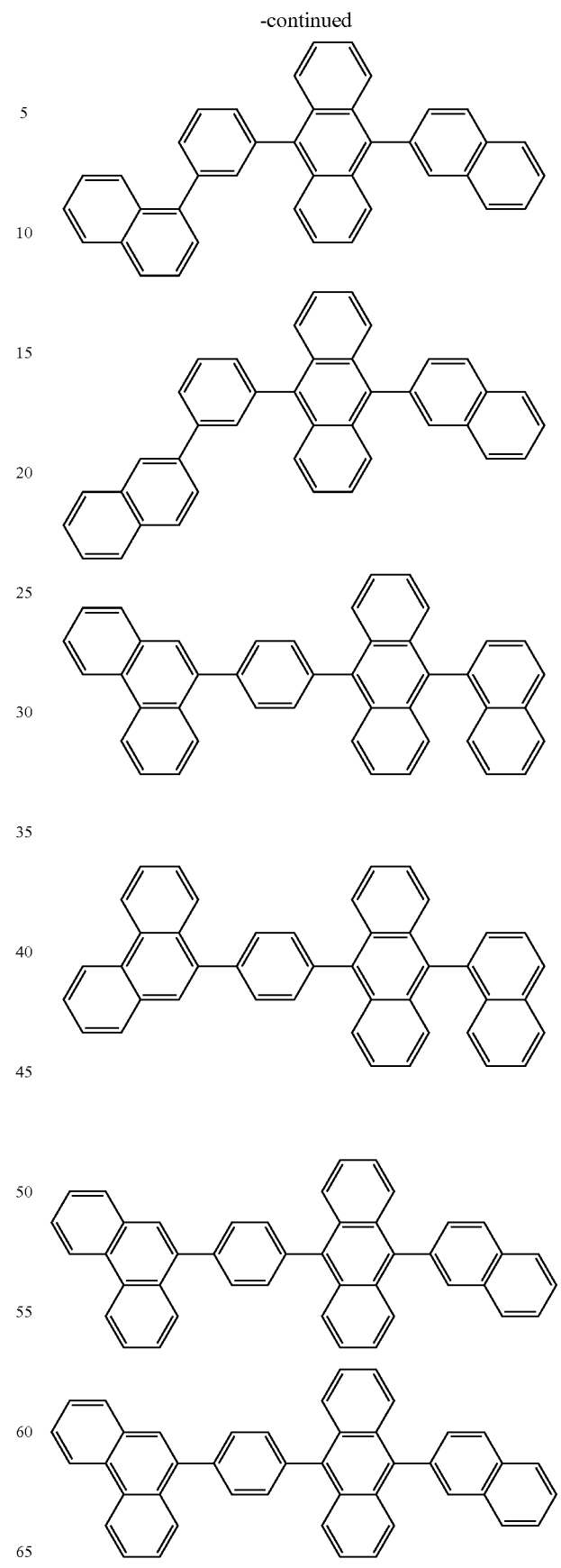

127
-continued
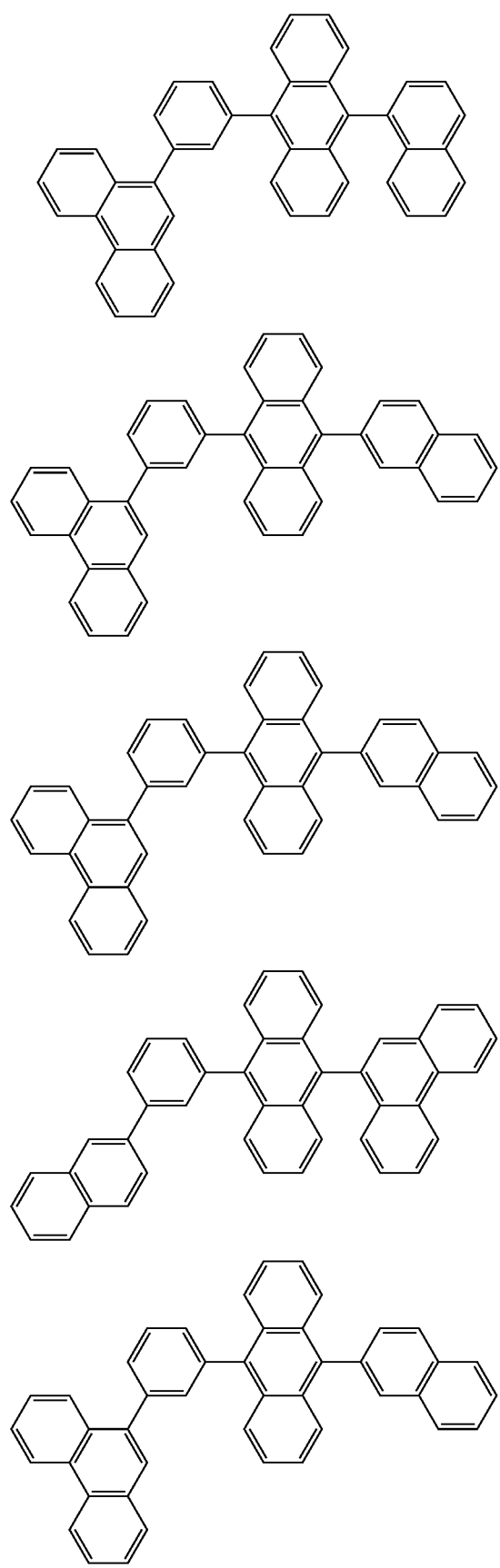
128
-continued
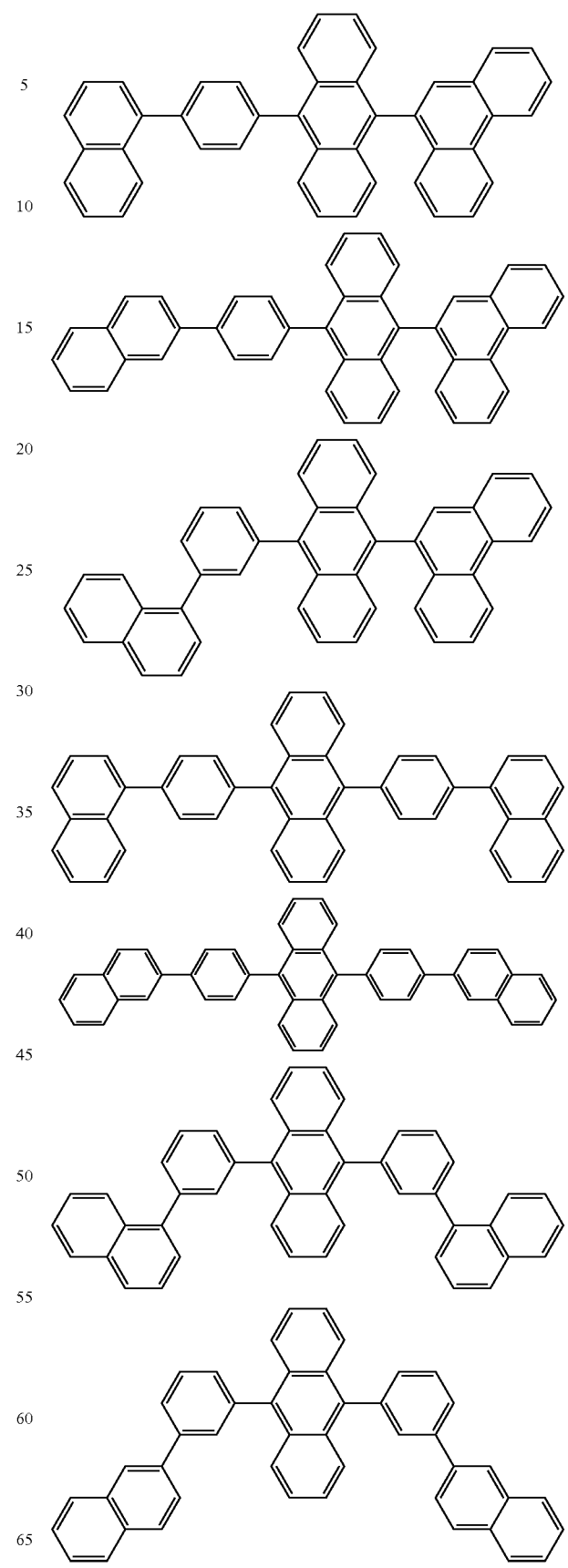

129
-continued
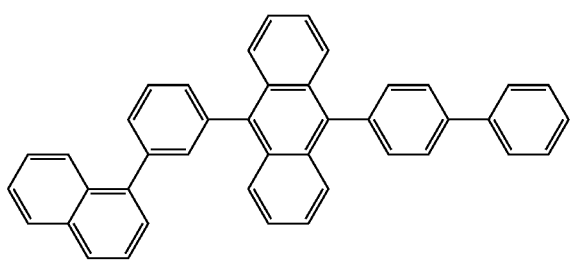
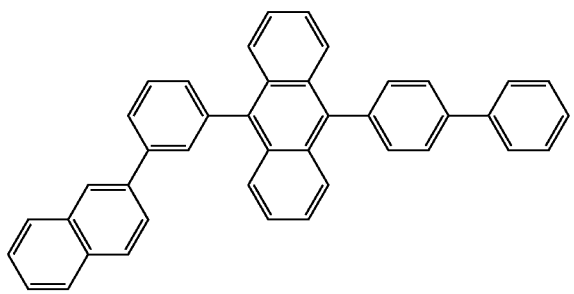
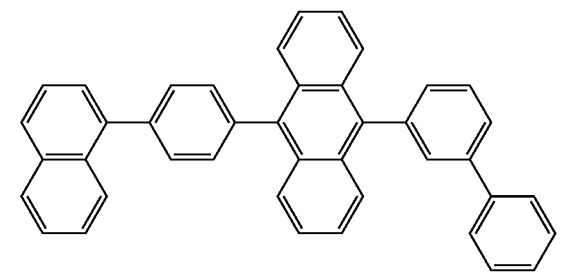
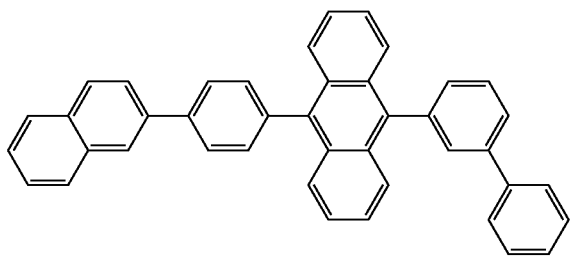
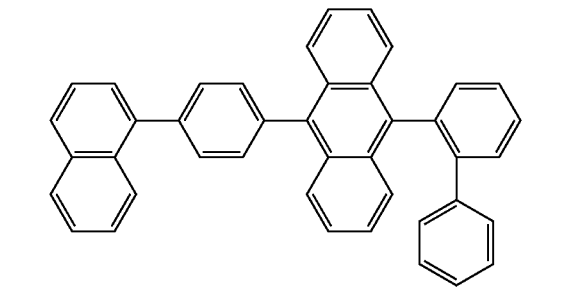
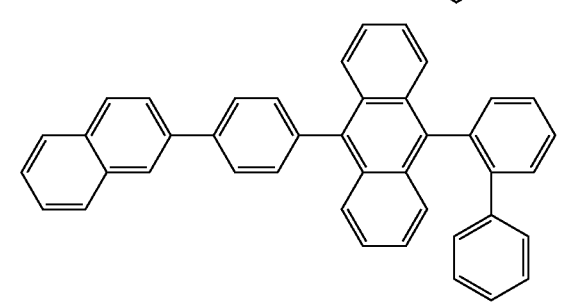
130
-continued
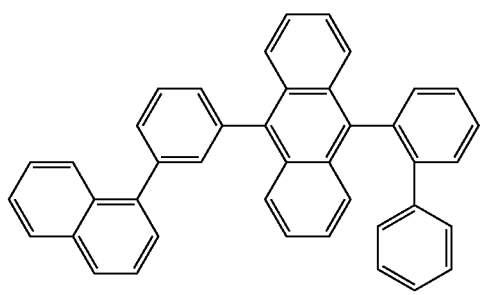
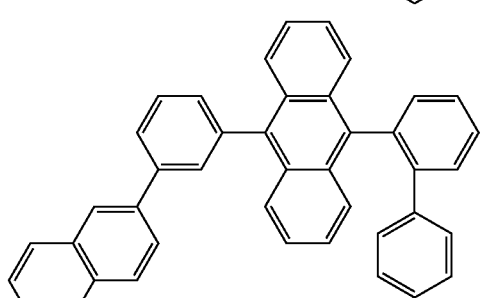
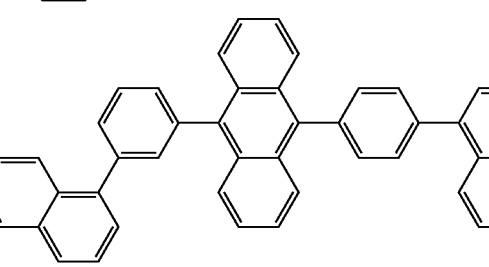
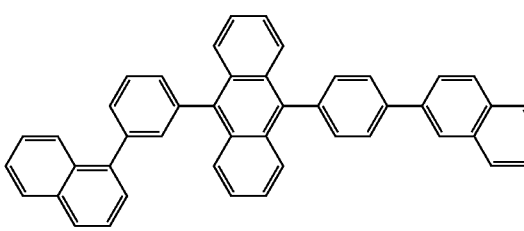
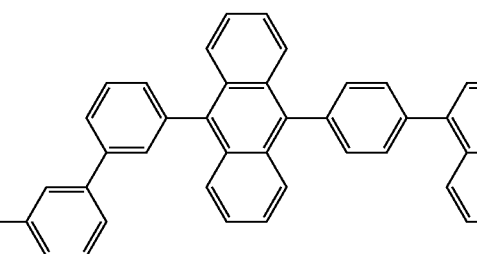
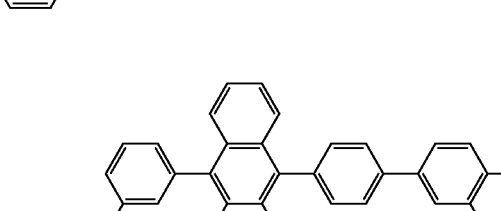
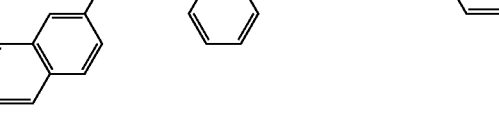

131
-continued
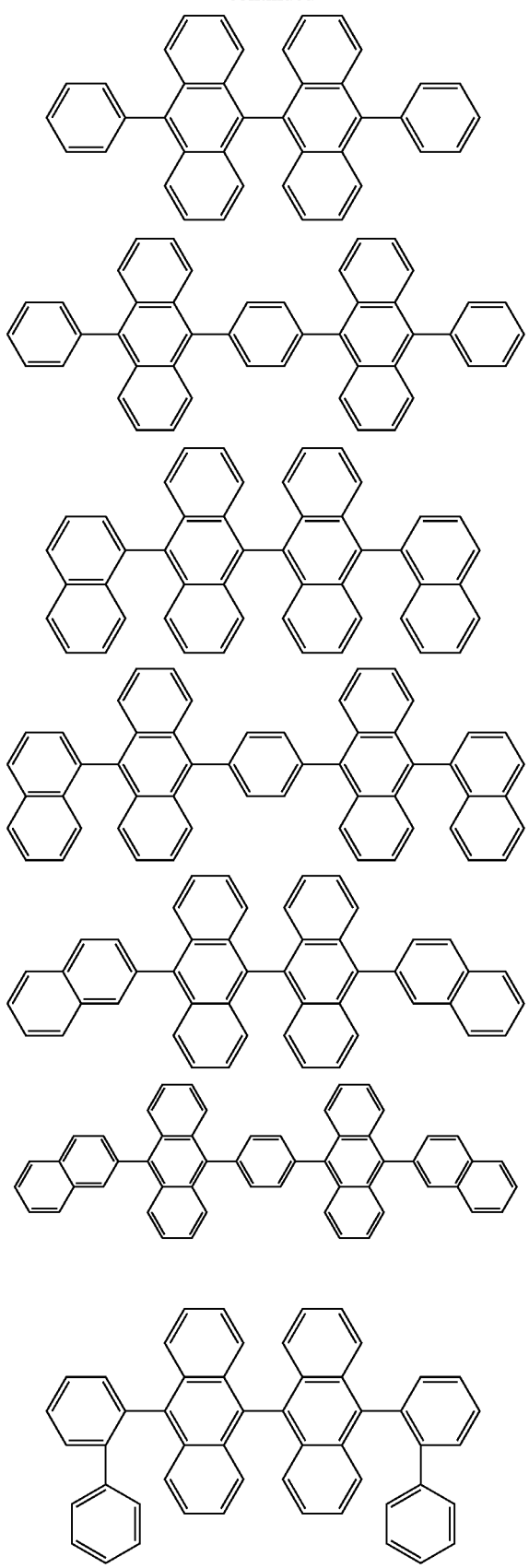
132
-continued
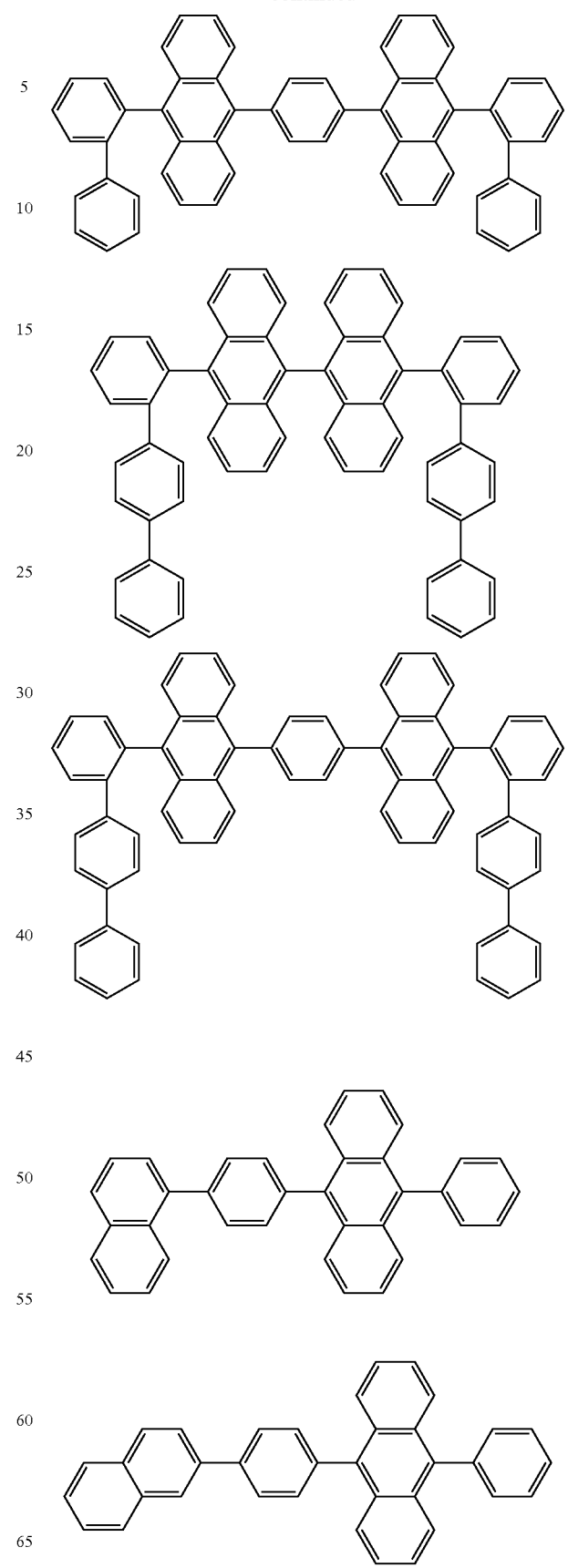

-continued
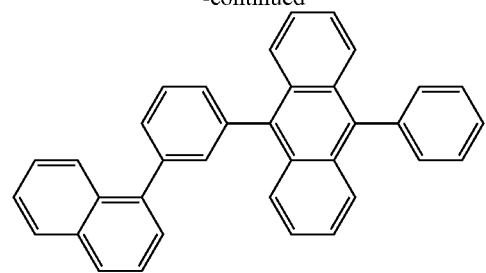
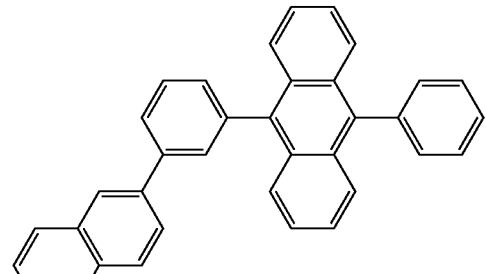
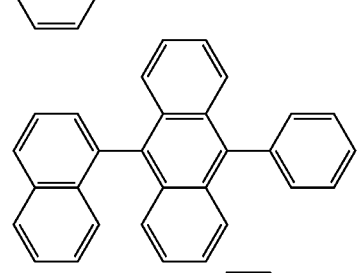
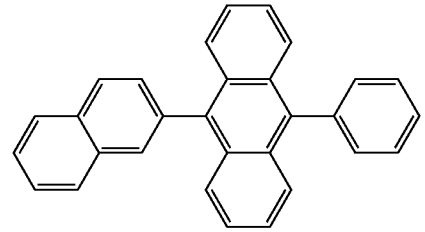
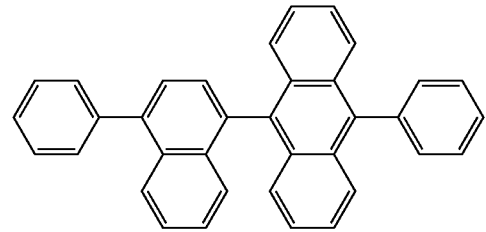
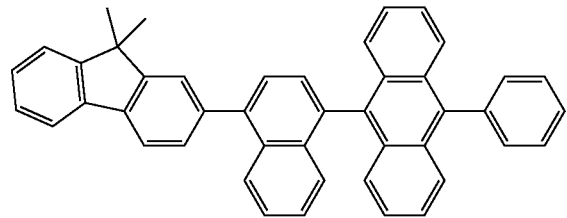
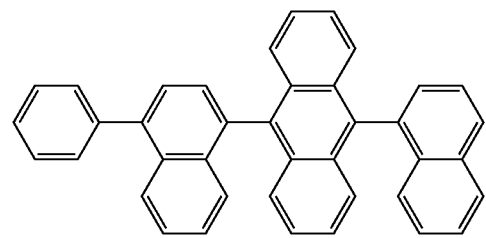
-continued
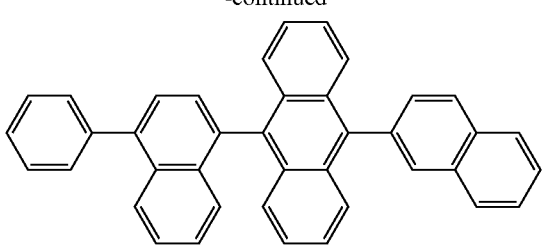
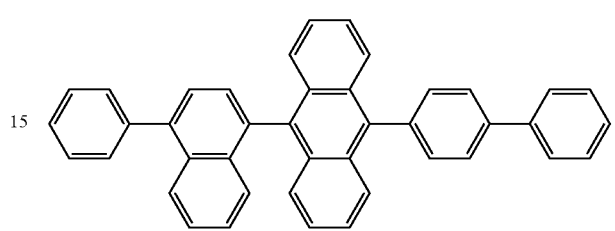
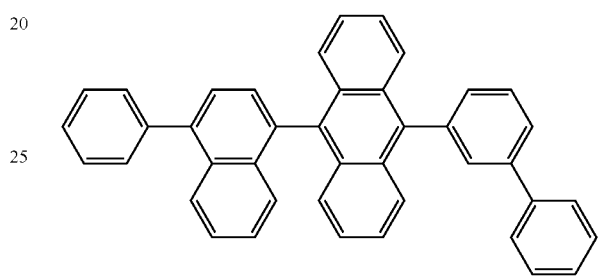
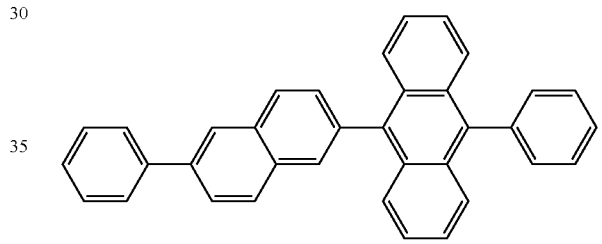
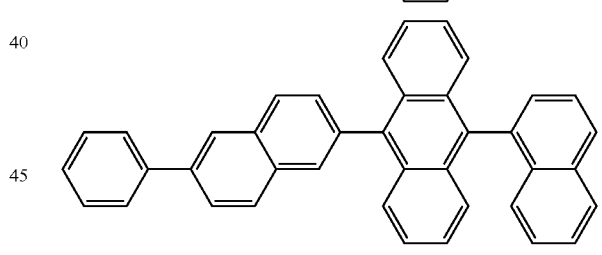
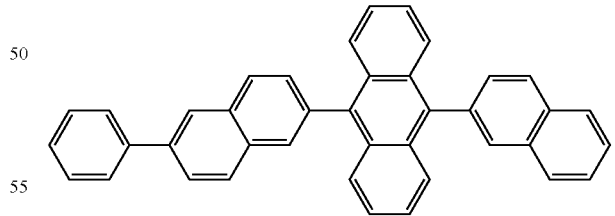
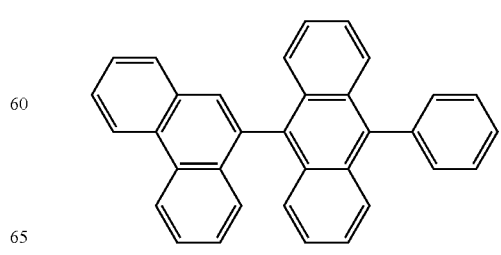

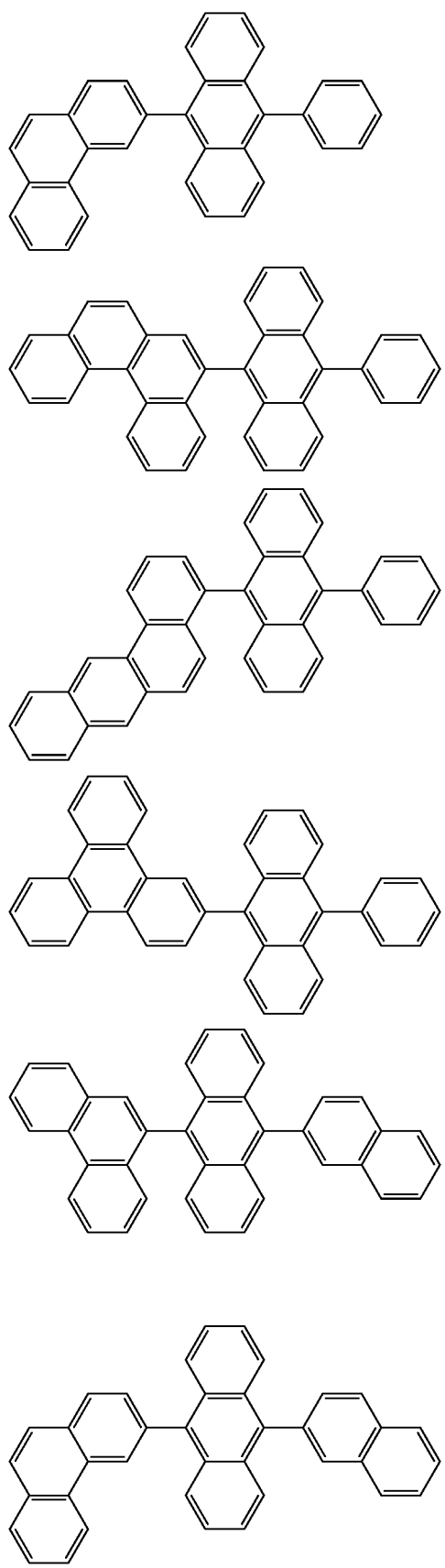
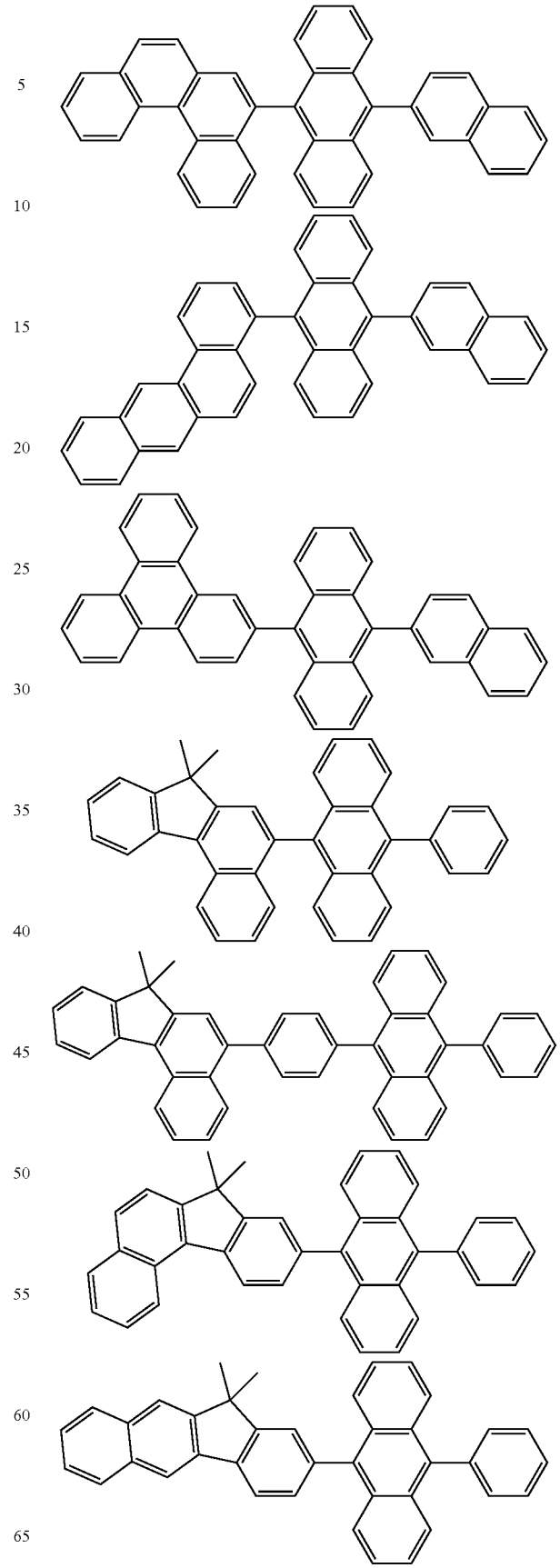

137
-continued
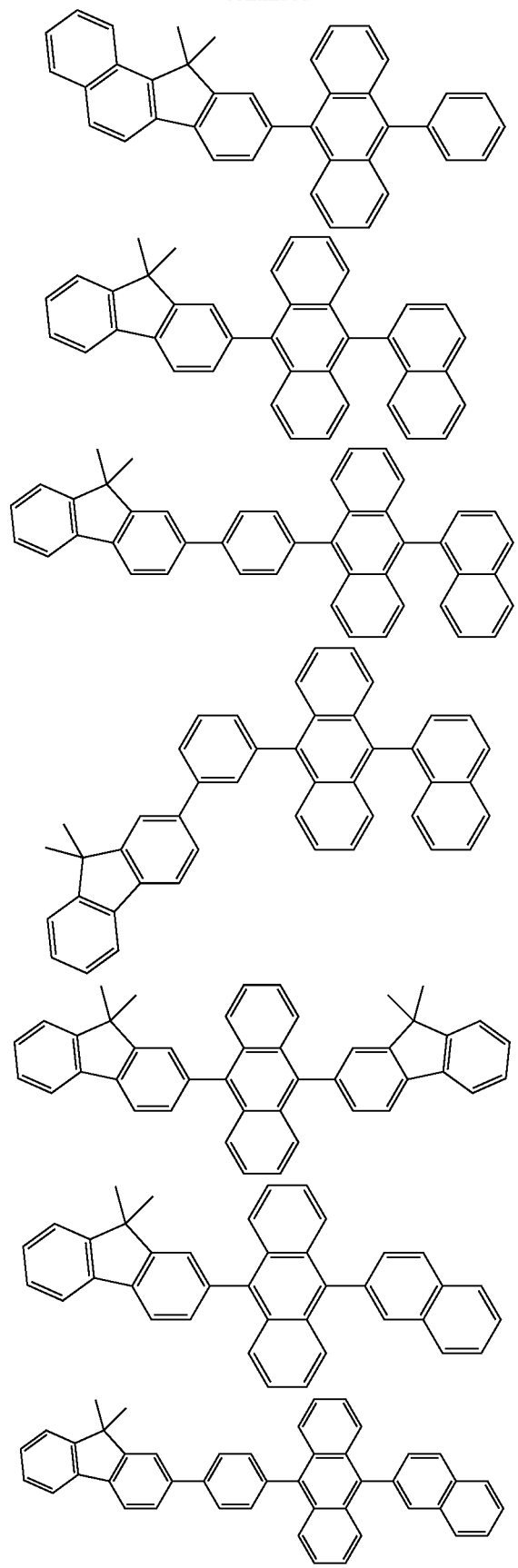
138
-continued
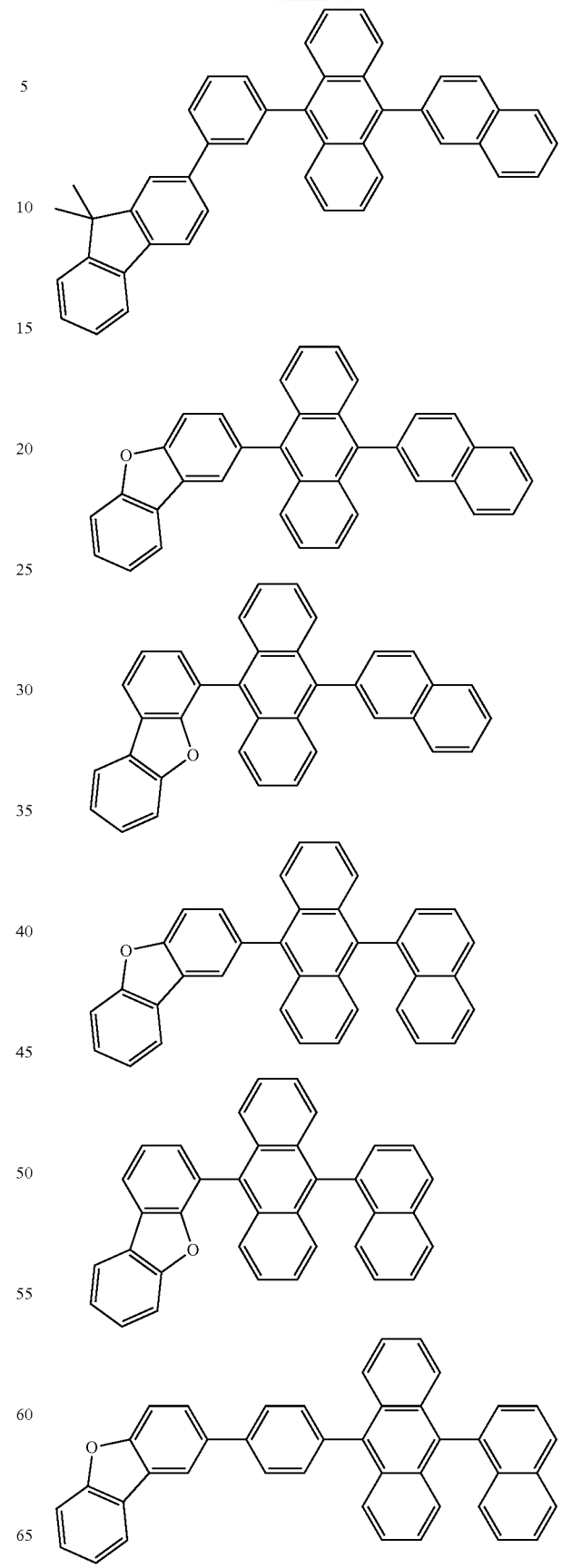

-continued
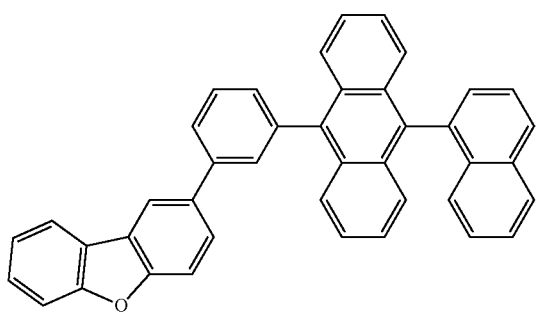
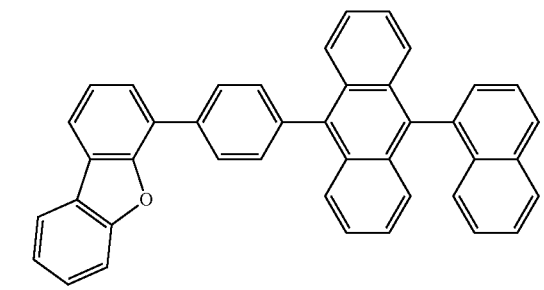
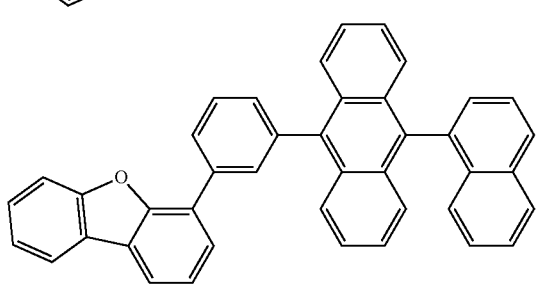
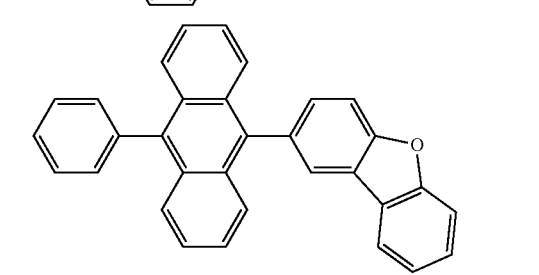
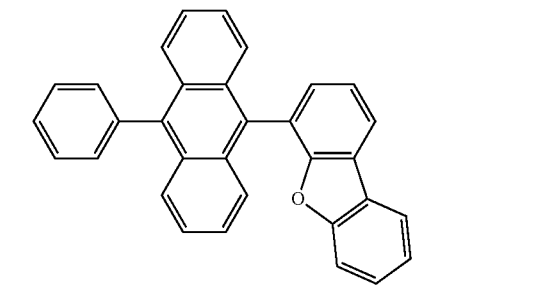
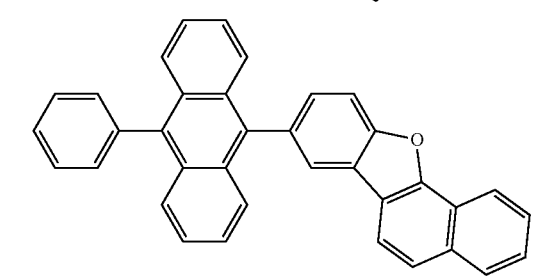
-continued
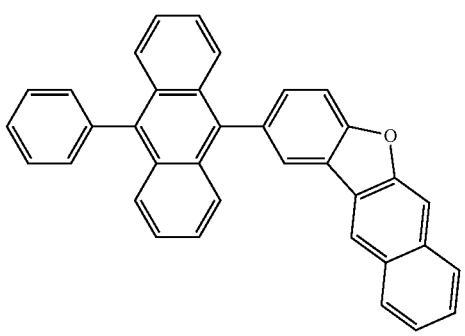
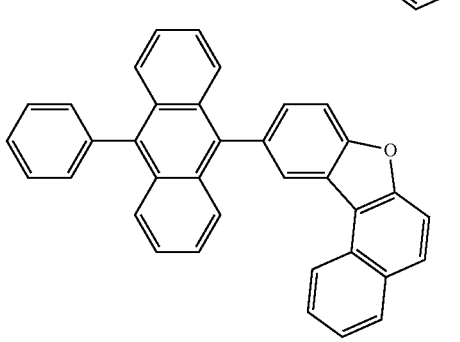
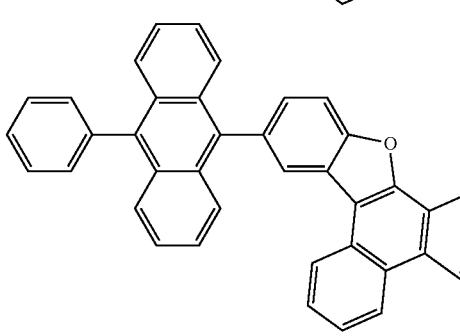
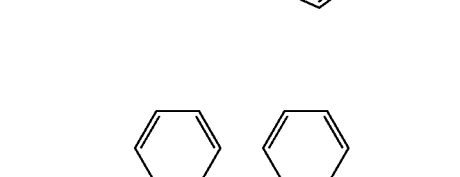
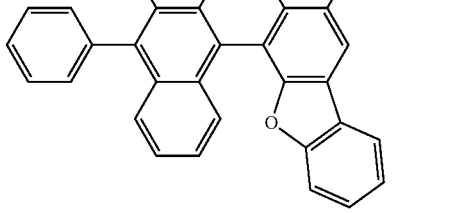

141
-continued
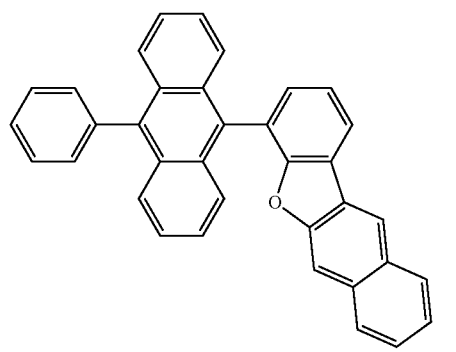
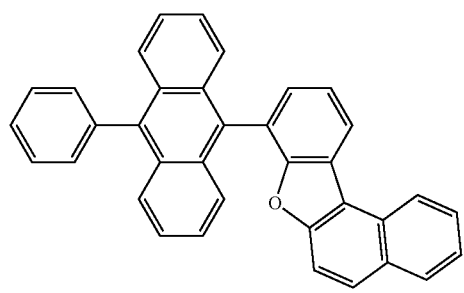
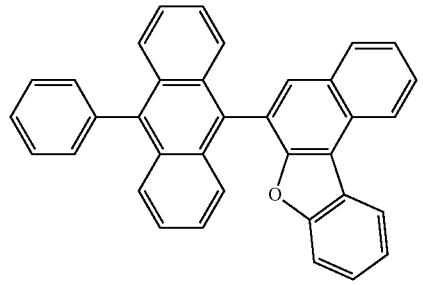
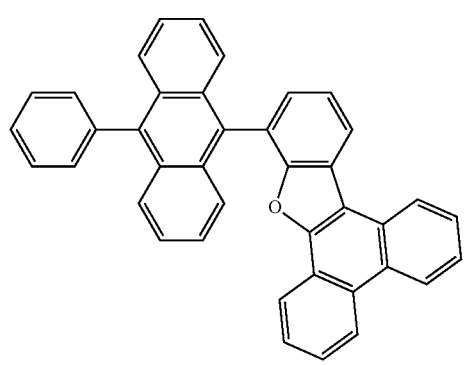
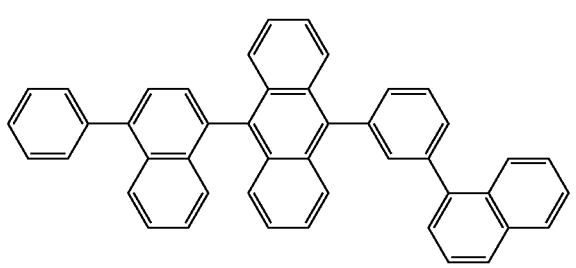
142
-continued
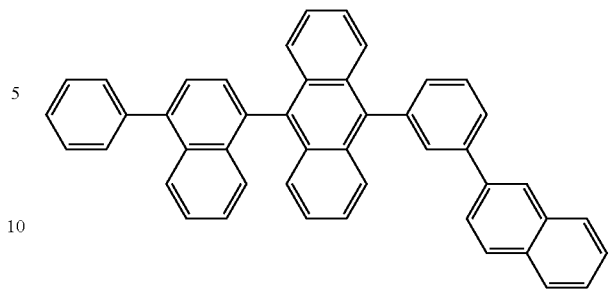
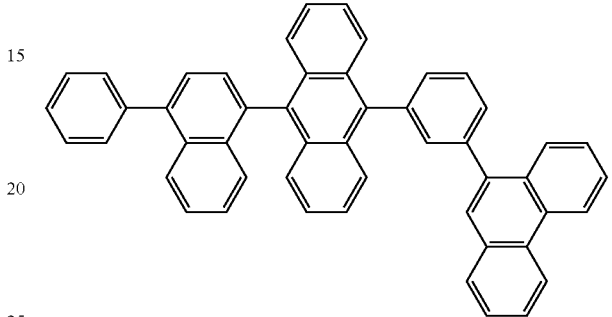
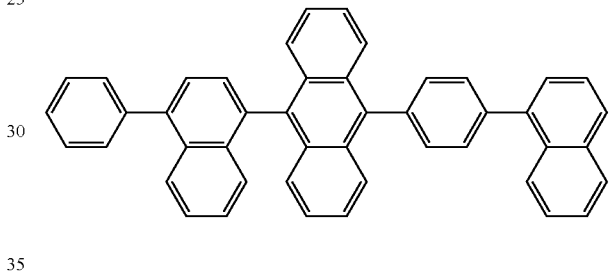
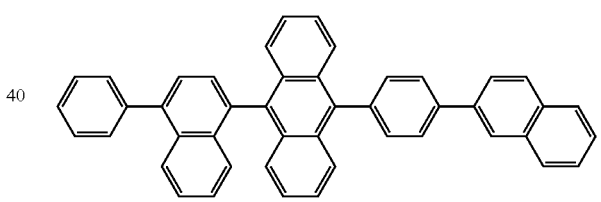
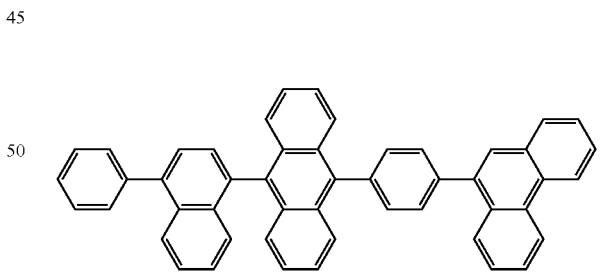
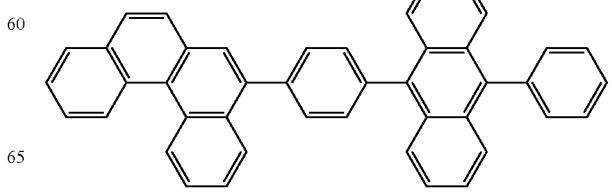

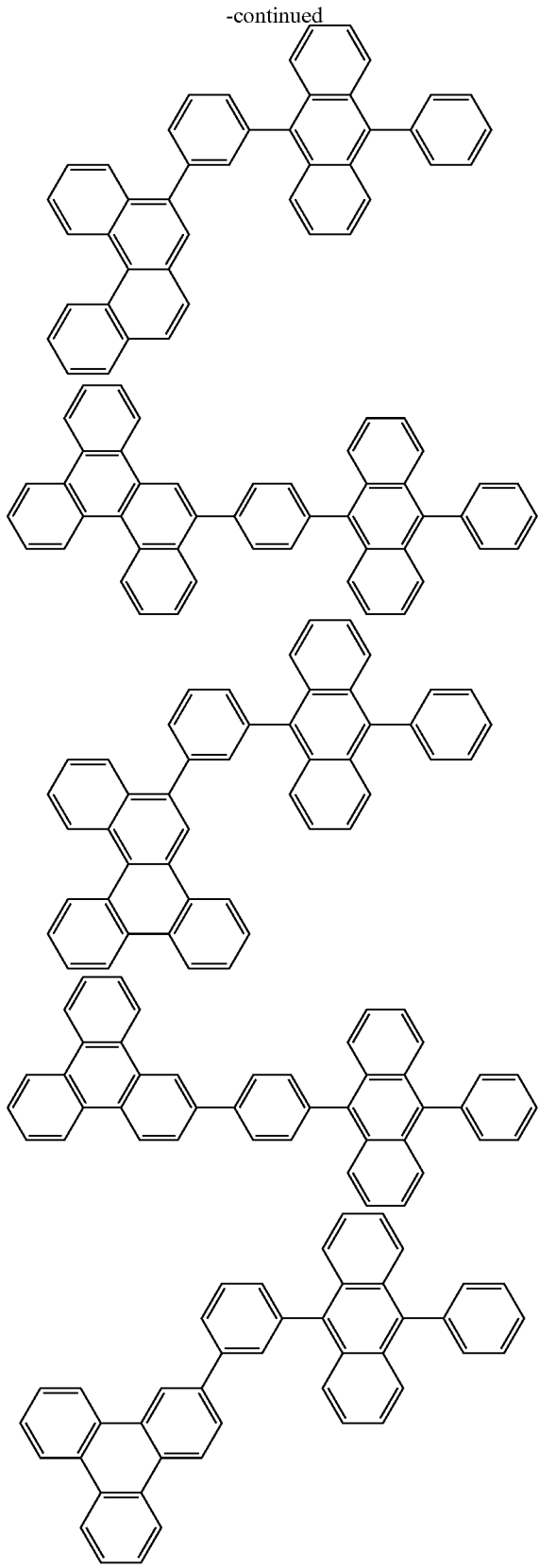

Electron Transporting Layer

The electron transporting layer comprises a material having a high electron transporting ability (electron transporting material) and formed between a light emitting layer and a cathode or between a light emitting layer and an electron injecting layer, if present.

The electron transporting layer may be a single layer or a multi-layer of two or more layers. For example, the electron transporting layer may be a two-layered structure comprising a first electron transporting layer (anode side) and a second electron transporting layer (cathode side). In an embodiment of the invention, an electron transporting layer of a single-layered structure is preferably in contact with a light emitting layer and an electron transporting layer in a multi-layered structure which is closest to an anode, for example, the first electron transporting layer in the two-layered structure mentioned above, is preferably in contact with a light emitting layer. In another embodiment of the invention, an hole blocking layer mentioned below may be disposed between the light emitting layer and the electron transporting layer of the single-layered structure or between the light emitting layer and the electron transporting layer in the multi-layered structure which is closest to the light emitting layer.

The electron transporting layer may be formed, for example, by (1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a macromolecular compound.

Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq2), bis(2-methyl-8-quinolinolato) (4-phenylphenolato)aluminum (III) (BAlq), bis(8-quinolinolato)zinc(II) (Znq), bis[2-(2-benzoxazolyl)phenolato] zinc(II) (ZnPBO), and bis[2-(2-benzothiazolyl)phenolato] zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazol-2-yl)stilbene (BzOs).

Examples of the macromolecular compound include poly [(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ cm$^2$/Vs or more. Materials other than those mentioned above are also usable in the electron transporting layer if their electron transporting ability is higher than their hole transporting ability.

Electron Injecting Layer

The electron injecting layer is a layer comprising a material having a high electron injecting ability, for example, an alkali metal, such as lithium (Li), cesium (Cs), an alkaline earth metal, such as magnesium (Mg), calcium (Ca), and strontium (Sr), a rare earth metal, such as europium (Eu) and ytterbium (Yb), and a compound of these metals, such as an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used in combination of two or more.

In addition, a material having an electron transporting ability which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the heteroaromatic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating layer formed of an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of stacked layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material having both the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and an exciton blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The exciton blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a clipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Compounds of the present invention used in production of organic EL devices of the following Examples 1 to 7:

Compound 1
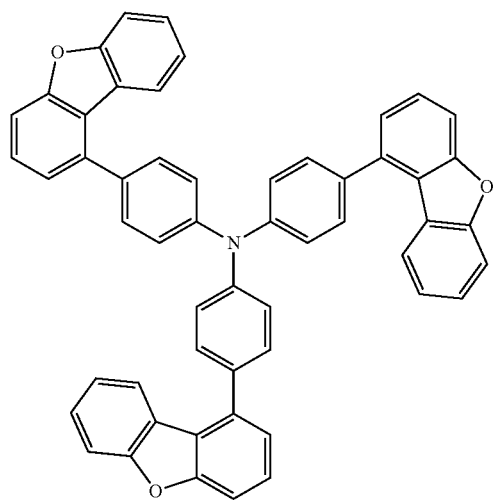
Compound 8
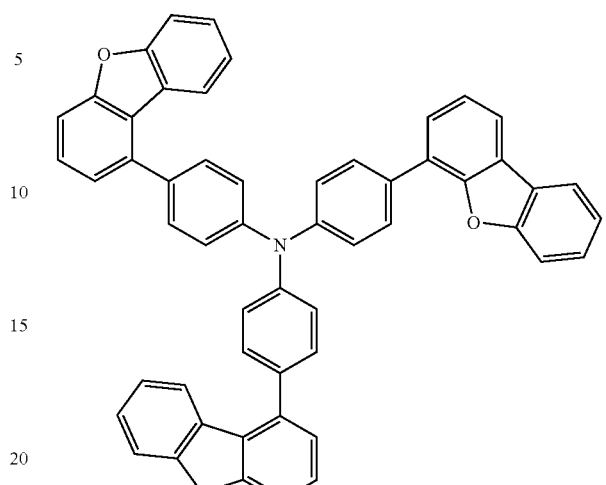
Compound 3
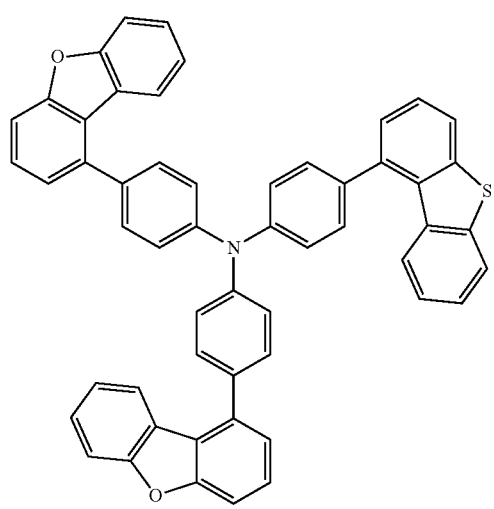
Compound 11
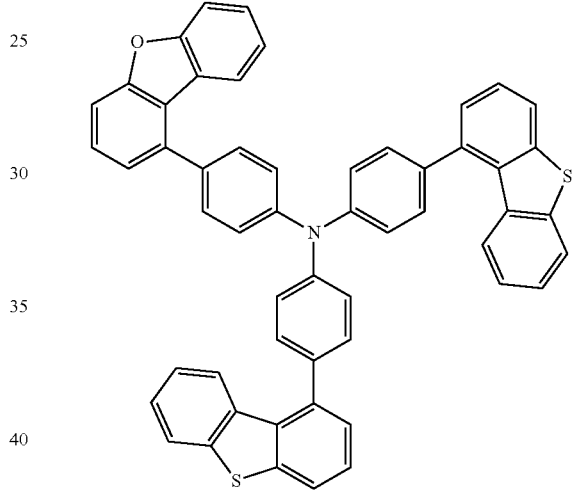
Compound 7
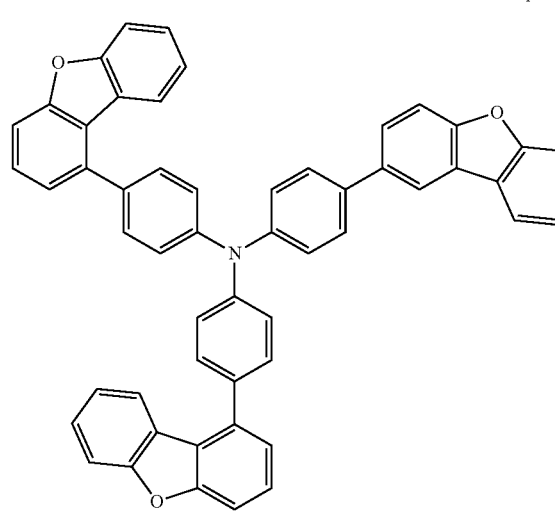
Compound 12
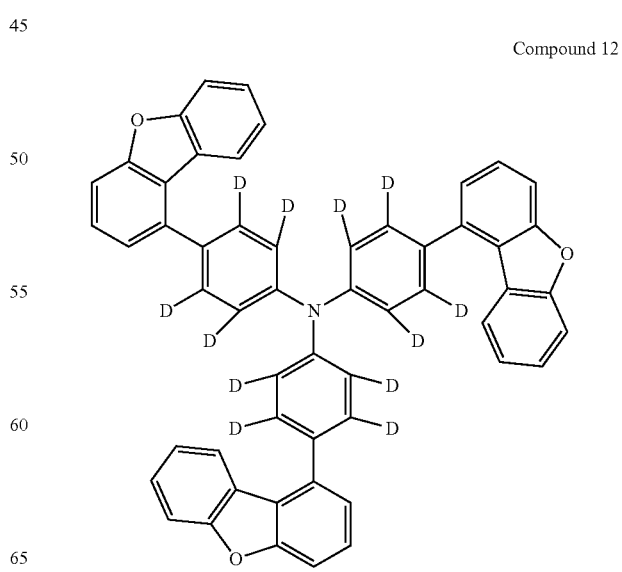

Comparative Compounds Used in Production of Organic EL Devices of the Following Comparative Examples 1 to 3
Ref-1
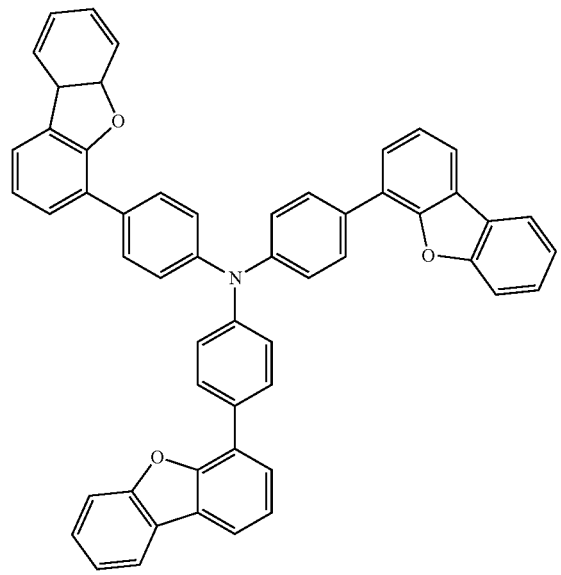
Ref-2
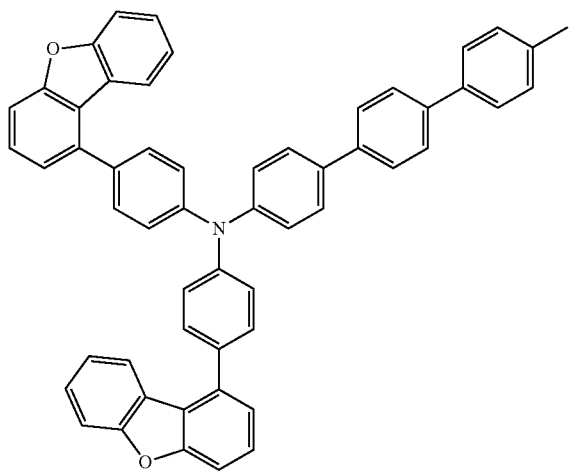
Ref-3
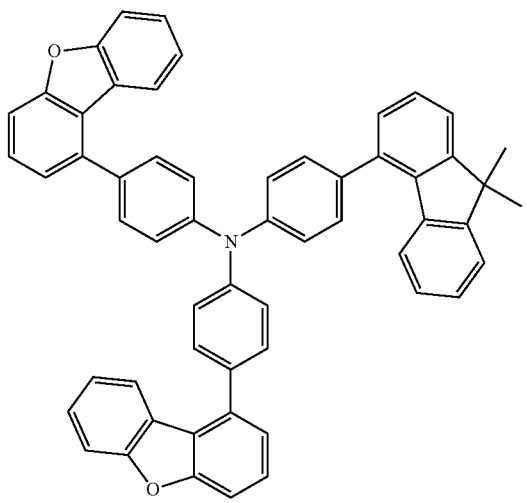
The comparative compound Ref-1 is a compound H14 described in PTL 1.
Other Compounds Used in Production of Organic EL Devices of the Following Example 1 and the Following Comparative Example 1
HI-1
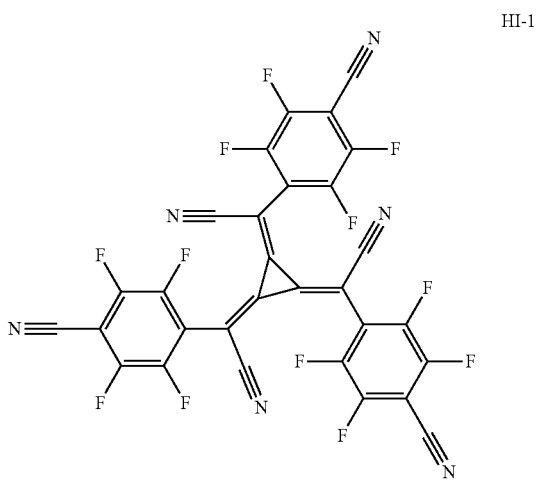

-continued
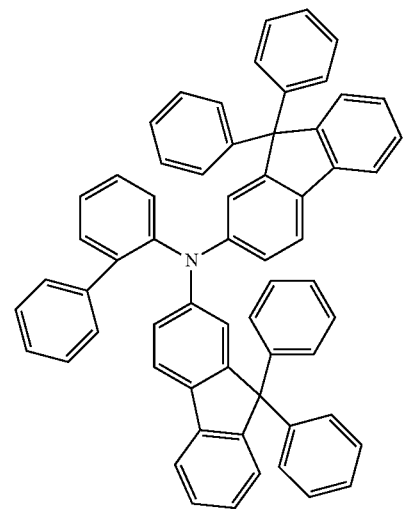
BH-1
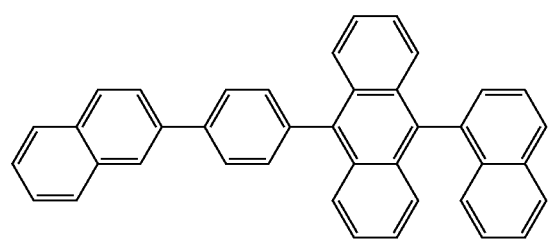
BD-1
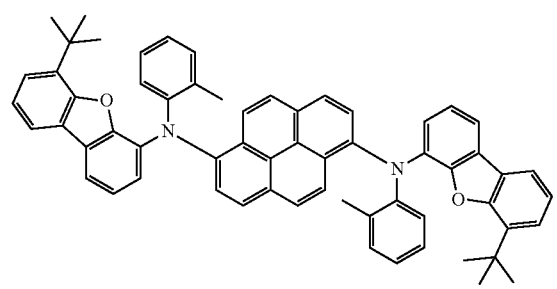
ET-1
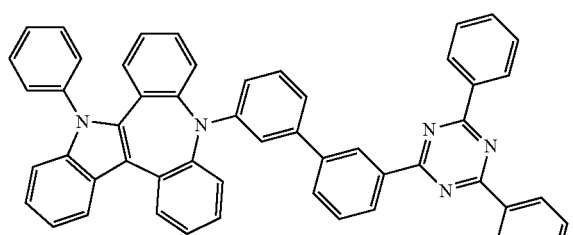
ET-2
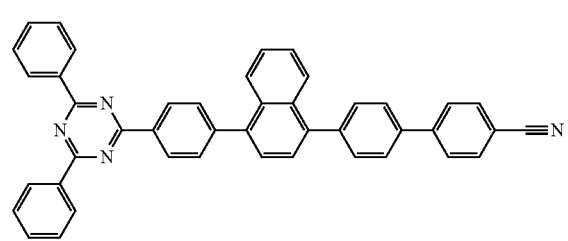
Other Compounds Used in Production of Organic EL Devices of the Following Examples 2 to 7 and the Following Comparative Examples 2 and 3
HI-1
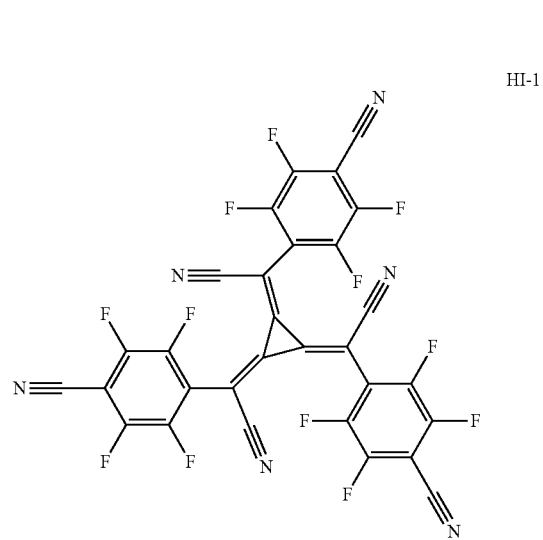
HT-1
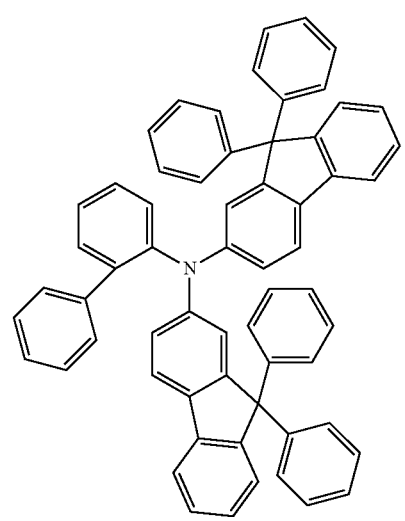
BH-2
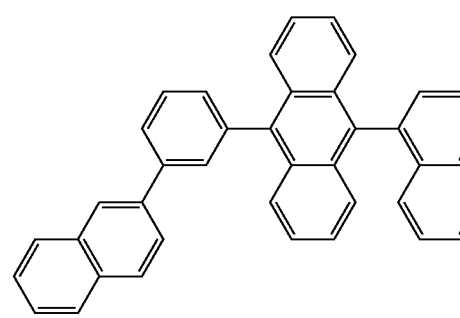

-continued

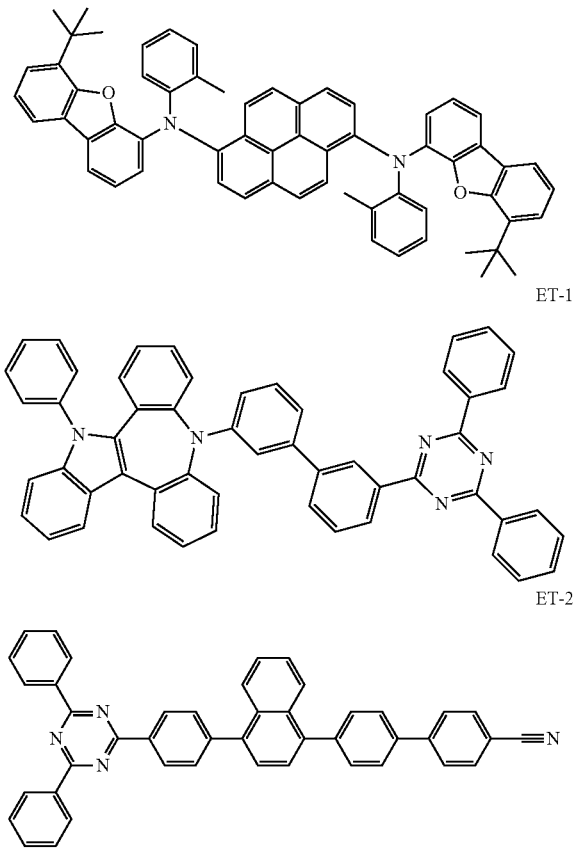

Each organic EL device was produced in the following manner and evaluated for EL device performance thereof.
Production of Organic EL Device Example 1

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode line was mounted to a substrate holder of a vacuum vapor deposition apparatus. First, the compound HT-1 and the compound HI-1 were vapor co-deposited on the surface having the transparent electrode line so as to cover the transparent electrode to form a hole injecting layer with a thickness of 10 nm. The ratio by mass of the compound HT-1 to the compound HI-1 was 97/3.

On the hole injecting layer, the compound HT-1 was vapor-deposited to form a first hole transporting layer with a thickness of 80 nm.

On the first hole transporting layer, the compound 1 was vapor-deposited to form a second hole transporting layer with a thickness of 10 nm.

Then, on the second hole transporting layer, the compound BH-1 (host material) and the compound BD-1 (dopant material) were vapor co-deposited to form a light emitting layer with a thickness of 25 nm. The ratio by mass of the compound BH-1 to the compound BD-1 was 96/4.

Then, on the light emitting layer, the compound ET-1 was vapor-deposited to form a first electron transporting layer, with a thickness of 5 nm.

Then, on the first electron transporting layer, the compound ET-2 and Liq were vapor co-deposited to form a second electron transporting layer with a thickness of 20 nm. The ratio by mass of the compound ET-2 to Liq was 50/50.

On the second electron transporting layer, LiF was vapor-deposited to form an electron injecting electrode (cathode) with a thickness of 1 nm.

Then, metallic Al was vapor-deposited on the electron injecting electrode to form a metallic cathode with a thickness of 50 nm.

The layered structure of the organic EL device of Example 1 produced in the manner as above is shown below:

ITO(130)/HT-1:HI-1=97:3(10)/HT-1(80)/Compound
1(10)/BH-1:BD-1=96:4(25)/ET-1(5)/ET-2:
Liq=50:50(20)/LiF(1)/Al(50)

In the layered structure, the numerals in parentheses are the thickness (nm), and the ratio of HT-1 to HI-1, the ratio of BH-1 to BD-1 and the ratio of ET-2 to Liq are by mass.

Comparative Example 1

An organic EL device of Comparative Example 1 was produced in the same manner as in Example 1 except that the second hole transporting layer compound (compound 1) in Example 1 was changed to the comparative compound Ref-1.

Example 2

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode line was mounted to a substrate holder of a vacuum vapor deposition apparatus. First, the compound HT-1 and the compound HI-1 were vapor co-deposited on the surface having the transparent electrode line so as to cover the transparent electrode to form a hole injecting layer with a thickness of 10 nm. The ratio by mass of the compound HT-1 to the compound HI-1 was 97/3.

On the hole injecting layer, the compound HT-1 was vapor-deposited to form a first hole transporting layer with a thickness of 80 nm.

On the first hole transporting layer, the compound 1 was vapor-deposited to form a second hole transporting layer with a thickness of 10 nm.

Then, on the second hole transporting layer, the compound BH-2 (host material) and the compound BD-1 (dopant material) were vapor co-deposited to form a light emitting layer with a thickness of 25 nm. The ratio by mass of the compound BH-1 to the compound BD-1 was 96/4.

Then, on the light emitting layer, the compound ET-1 was vapor-deposited to form a first electron transporting layer, with a thickness of 5 nm.

Then, on the first electron transporting layer, the compound ET-2 and Liq were vapor co-deposited to form a second electron transporting layer with a thickness of 20 nm. The ratio by mass of the compound ET-2 to Liq was 50/50.

On the second electron transporting layer, LiF was vapor-deposited to form an electron injecting electrode (cathode) with a thickness of 1 nm.

Then, metallic Al was vapor-deposited on the electron injecting electrode to form a metallic cathode with a thickness of 50 nm.

The layered structure of the organic EL device of Example 1 produced in the manner as above is shown below:

ITO(130)/HT-1:HI-1=97:3(10)/HT-1(80)/Compound 1(10)/BH-2:BD-1=96:4(25)/ET-1(5)/ET-2: Liq=50:50(20)/LiF(1)/Al(50)

In the layered structure, the numerals in parentheses are the thickness (nm), and the ratio of HT-1 to HI-1, the ratio of BH-1 to BD-1 and the ratio of ET-2 to Liq are by mass.

Examples 3 to 7

Organic EL devices of Examples 3 to 7 were produced in the same manner as in Example 2, except that the second hole transporting layer compound in Example 2 was changed to the compound 3, 7, 8, 11 or 12, respectively.

Comparative Examples 2 to 3

Organic EL devices of Comparative Examples 2 to 3 were produced in the same manner as in Example 2, except that the second hole transporting layer compound in Example 2 was changed to the comparative compound Ref-2 or Ref-3, respectively.

Evaluation of Organic EL Device

Each of the organic EL devices produced above was evaluated in point of the external quantum efficiency thereof. The evaluation results are shown in Table 1.

Measurement of External Quantum Efficiency (EQE)

The resultant organic EL device was driven on DC at a current density of 10 mA/cm², and the luminance thereof was measured using a luminance meter (Spectral Radiance Meter CS-1000 by Minolta Co., Ltd.). The external quantum efficiency (%) was calculated from the measured data.

TABLE 1

|  | Second Hole Transporting Layer Material | External Quantum Efficiency (%) @10 mA/cm² |
| --- | --- | --- |
| Example 1 | Compound 1 | 9.7 |
| Comparative Example 1 | Comparative Compound Ref-1 | 8.8 |
| Example 2 | Compound 1 | 9.9 |
| Example 3 | Compound 3 | 10.0 |
| Example 4 | Compound 7 | 9.4 |
| Example 5 | Compound 8 | 9.4 |
| Example 6 | Compound 11 | 10.0 |
| Example 7 | Compound 12 | 10.1 |
| Comparative Example 2 | Comparative Compound Ref-2 | 8.3 |
| Comparative Example 3 | Comparative Compound Ref-3 | 8.2 |

As is evident from the results in Table 1, the organic EL devices each containing the compound 1 of the present invention, which has three 1-dibenzofuranyl group-having p-phenylene groups bonding to the central nitrogen atom, have a high efficiency (high external quantum efficiency).

Specifically, the organic EL devices each containing the compound 1 of the present invention show an extreme efficiency (external quantum efficiency), as compared with the organic EL device containing the compound Ref-1 described in PTL 1.

From comparison between Example 1 and Comparative Example 1, it is known that the 1-dibenzofuranyl group bonding via the p-phenylene group on the central nitrogen atom brings about an effect of extremely improving the external quantum efficiency, as compared with the 4-dibenzofuranyl group bonding via the p-phenylene group on the central nitrogen atom.

Also the organic EL devices each containing the compounds 1, 3, 7, 8, 11 and 12 of the present invention, which have three p-phenylene groups each having a group selected from a 1-dibenzofuranyl group and a 1-dibenzothiophenyl group and bonding to the central nitrogen atom, have a high efficiency (high external quantum efficiency).

From comparison between Examples 2 to 7 and Comparative Examples 2 to 3, it is known that the structure containing a group selected from a 1-dibenzofuranyl group and a 1-dibenzothiophenyl group, as bonding via the three p-phenylene groups on the central nitrogen atom, brings about an effect of extremely improving the external quantum efficiency, as compared with the structure that contains a biphenyl group or a fluorenyl group (aryl group) bonding via only one p-phenylene group on the central nitrogen atom.

Intermediate Synthesis Example 1: Synthesis of Intermediate A

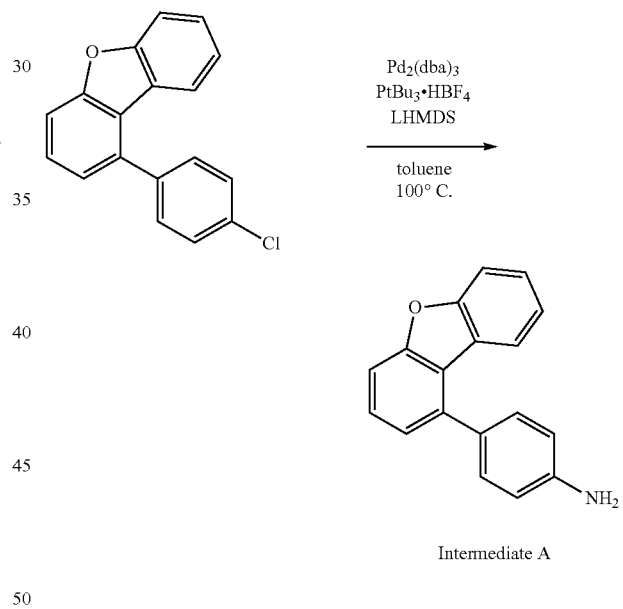

Intermediate A

In an argon atmosphere, a mixture of 1-(4-chlorophenyl)dibenzo[b,d]furan (4.18 g, 15.0 mmol) synthesized according to the same method as in WO2018/164201, tris(dibenzylideneacetone)dipalladium(0) (0.275 g, 0.30 mmol), tri-t-butylphosphonium tetrafluoroborate (0.348 g, 1.20 mmol), a 1.0 M toluene solution of lithium bis(trimethylsilyl)amide (30 ml, 30.0 mmol) and toluene (30 mL) was stirred at 100° C. for 6 hours. The reaction liquid was cooled to room temperature, then 1 M hydrochloric acid (30 mL) was added and stirred. An aqueous 1 M sodium hydroxide solution was added, then the mixture liquid was made basic, extracted with toluene, and the organic layer was dried with magnesium sulfate and then concentrated under reduced pressure. The resultant residue was purified through silica gel column chromatography to give the intermediate A (3.16 g). The yield was 81%.

Intermediate Synthesis Example 2: Synthesis of Intermediate B

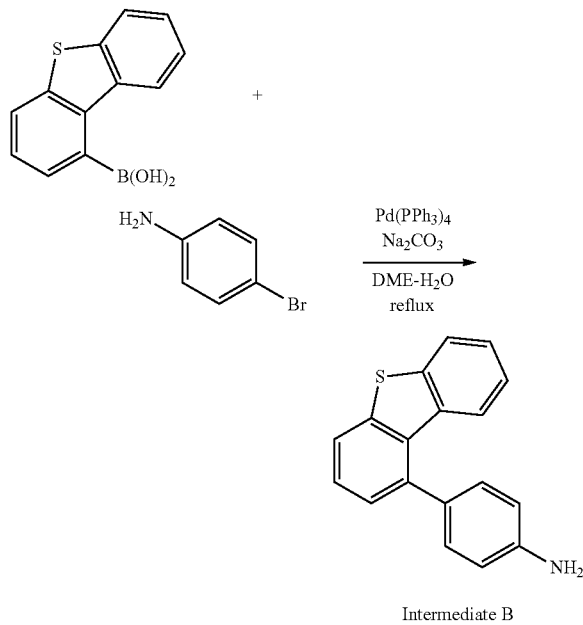

Intermediate B

In an argon atmosphere, a mixture of 1-dibenzothiophene-boronic acid (5.02 g, 22.0 mmol) synthesized according to the same method as in US 2018/0337348A, 4-bromoaniline (3.44 g, 20 mmol), tetrakis(triphenylphosphine)palladium (0) (0.462 g, 0.40 mmol), sodium carbonate (5.30 g, 50.0 mmol), DME (80 mL) and water (20 mL) was refluxed for 7 hours. The reaction liquid was cooled to room temperature, water was added, then this was extracted with ethyl acetate, and the organic layer was dried with anhydrous magnesium sulfate and concentrated under reduced pressure. The resultant residue was purified through silica gel column chromatography to give the intermediate B (8.12 g). The yield was 70%.

Intermediate Synthesis Example 3: Synthesis of Intermediate C

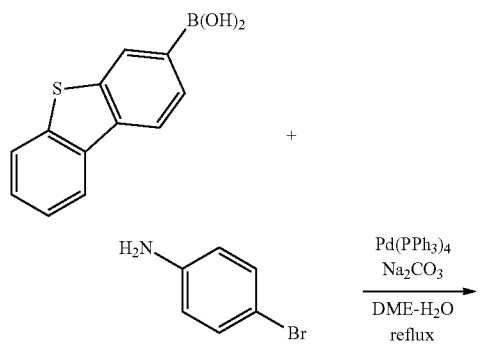

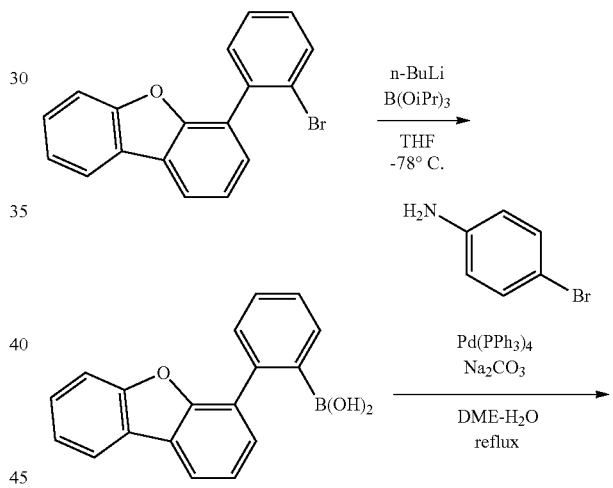

Intermediate C

In the same manner as in Intermediate Synthesis Example 2 except that 3-dibenzothiophene-boronic acid synthesized according to the same method as in JP 2018-090561A was used in place of 1-dibenzothiophene-boronic acid in Intermediate Synthesis Example 2, the intermediate C was produced. The yield was on the same level as that in Intermediate Synthesis Example 2.

Intermediate Synthesis Example 4: Synthesis of Intermediate D

Intermediate D-1

Intermediate D (1) Synthesis of Intermediate D-1

In an argon atmosphere, a mixture of 4-(2-bromophenyl) dibenzofuran (4.85 g, 15.0 mmol) synthesized in the same manner as in KR 2017/0141989A and THF (45 mL) was cooled to −78° C., then a 1.6 M hexane solution of n-butyl lithium (28.8 mL, 18.0 mmol) was dropwise added thereto and stirred for 1 hour. Triisopropyl borate (2.46 mL, 18.0 mmol) was added, and further stirred for 1 hour, and then the reaction liquid was restored to room temperature and further stirred for 10 hours. 1 M hydrochloric acid (20 mL) was added to the reaction liquid, stirred for 1 hour, then extracted with ethyl acetate, and the organic layer was dried with magnesium sulfate and concentrated under reduced pressure to give the intermediate D-1 (3.99 g). The yield was 77%.

(2) Synthesis of Intermediate D

In the same manner as in Intermediate Synthesis Example 2 except that the intermediate D-1 was used in place of 1-dibenzothiophene-boronic acid in Intermediate Synthesis Example 2, the intermediate D was produced. The yield was on the same level as that in Intermediate Synthesis Example 2.

Intermediate Synthesis Example 5: Synthesis of Intermediate E

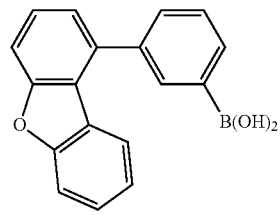
+
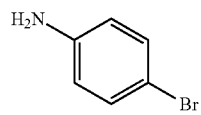
Pd(PPh₃)₄
Na₂CO₃
―――――→
DME-H₂O
reflux

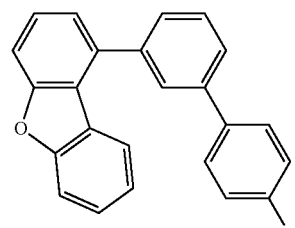

Intermediate E

In the same manner as in Intermediate Synthesis Example 2 except that 3-(dibenzofuran-1-yl)phenylboronic acid synthesized in the same manner as in JP 2018-090561A was used in place of 1-dibenzothiophene-boronic acid in Intermediate Synthesis Example 2, the intermediate E was produced. The yield was on the same level as that in Intermediate Synthesis Example 2.

Intermediate Synthesis Example 6: Synthesis of Intermediate F

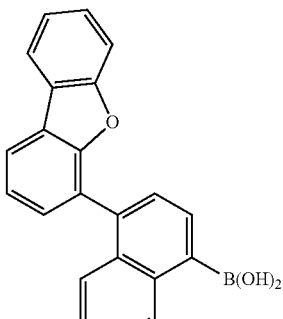
+
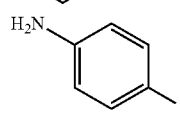
Pd(PPh₃)₄
Na₂CO₃
―――――→
DME-H₂O
reflux

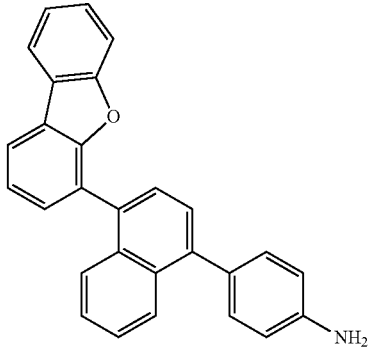

Intermediate F

In the same manner as in Intermediate Synthesis Example 2 except that 4-(dibenzofuran-4-yl)-1-naphthalene-boronic acid synthesized in the same manner as in CN 106187963A was used in place of 1-dibenzothiophene-boronic acid in Intermediate Synthesis Example 2, the intermediate F was produced. The yield was on the same level as that in Intermediate Synthesis Example 2.

Intermediate Synthesis Example 7: Synthesis of Intermediate G

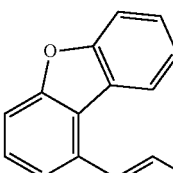
+
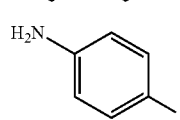
Pd(PPh₃)₄
Na₂CO₃
―――――→
DME-H₂O
reflux

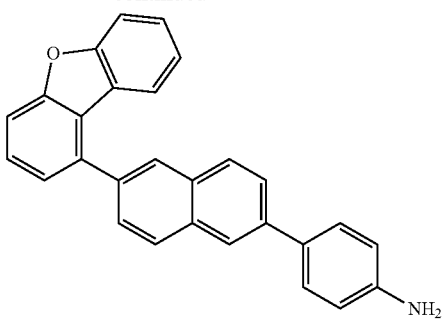

Intermediate G

In the same manner as in Intermediate Synthesis Example 2 except that 6-(dibenzofuran-1-yl)-2-naphthalene-boronic acid synthesized in the same manner as in CN 106187963A was used in place of 1-dibenzothiophene-boronic acid in Intermediate Synthesis Example 2, the intermediate G was produced. The yield was on the same level as that in Intermediate Synthesis Example 2.

Intermediate Synthesis Example 8: Synthesis of Intermediate H

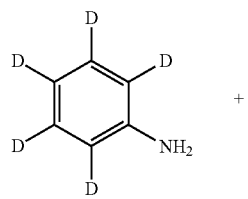

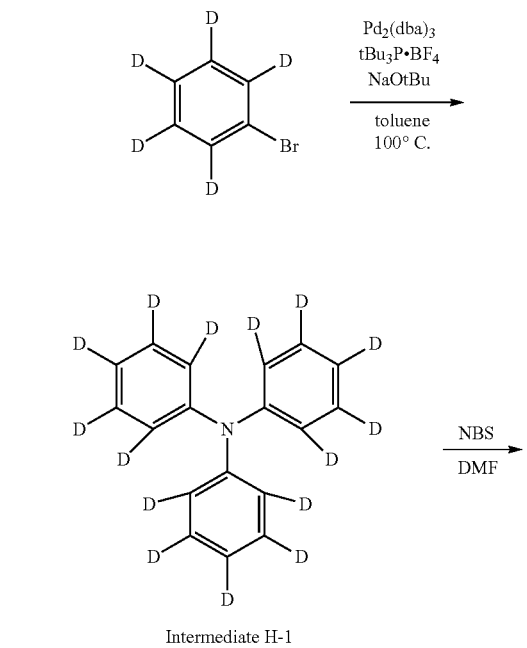

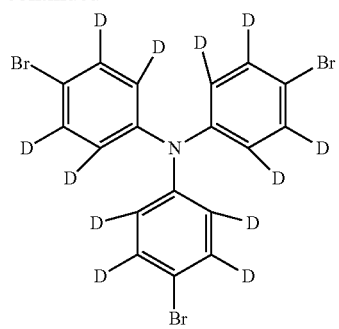

Intermediate H (1) Synthesis of Intermediate H-1

In an argon atmosphere, a mixture of aniline-d5 (2.60 g, 26.5 mmol), bromobenzene-d5 (9.45 g, 58.3 mmol), tris (dibenzylideneacetone)dipalladium(0) (0.485 g, 0.53 mmol), tri-t-butylphosphonium tetrafluoroborate (0.615 g, 2.12 mmol), sodium t-butoxide (6.11 g, 63.6 mmol) and toluene (130 mL) was stirred at 100° C. for 6 hours, The reaction liquid was cooled to room temperature, and then the filtrate was concentrated under reduced pressure. The resultant residue was purified through silica gel column chromatography to give the intermediate H-1 (6.00 g). The yield was 87%.

(2) Synthesis of Intermediate H

In an argon atmosphere, a mixture of the intermediate H-1 (5.21 g, 20.0 mmol) and DMF (170 mL) was cooled to 0° C., then N-bromosuccinimide (10.75 g, 60.4 mmol) was added thereto and stirred at room temperature for 24 hours. Water was added to the reaction liquid, the precipitated solid was taken out by filtration, and purified through silica gel column chromatography to give the intermediate H (9.40 g). The yield was 95%.

Intermediate Synthesis Example 9: Synthesis of Intermediate I

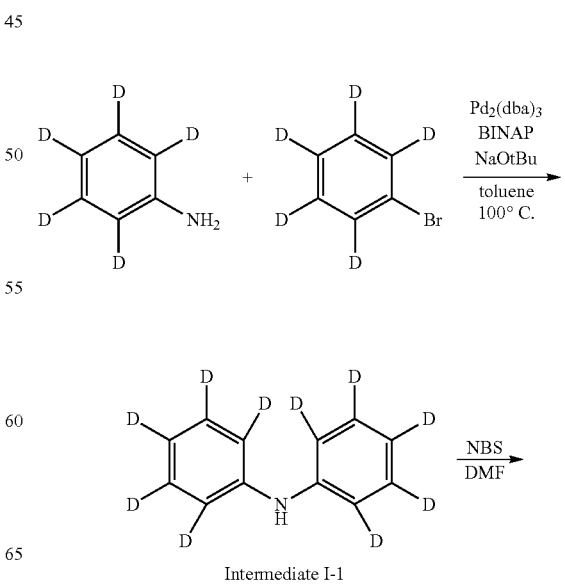

Synthesis Example 1: Synthesis of Compound 1

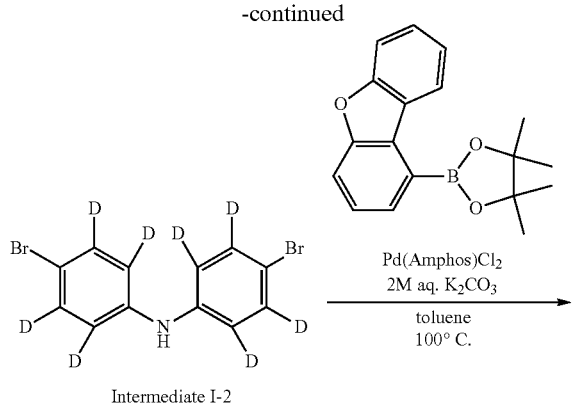

Intermediate I-2

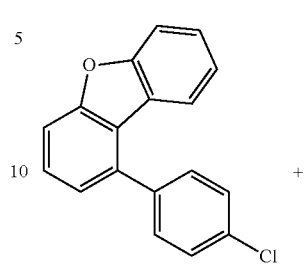

Intermediate A

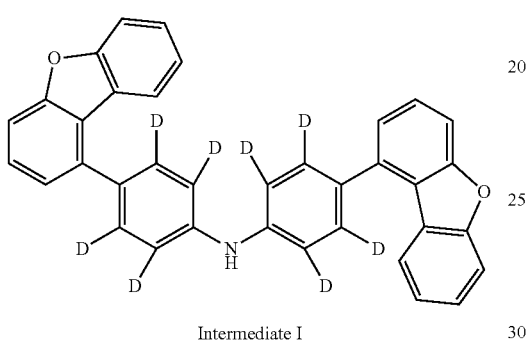

Intermediate I

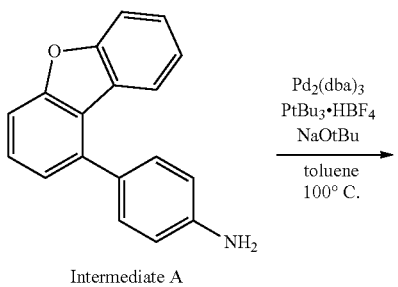

Compound 1

(1) Synthesis of Intermediate I-1

In an argon atmosphere, a mixture of aniline-d5 (2.60 g, 26.5 mmol), bromobenzene-d5 (4.73 g, 26.5 mmol), tris(dibenzylideneacetone)dipalladium(0) (0.485 g, 0.53 mmol), BINAP (0.615 g, 1.06 mmol), sodium t-butoxide (3.82 g, 39.8 mmol) and toluene (130 mL) was stirred at 100° C. for 6 hours, The reaction liquid was cooled to room temperature, and then the filtrate was concentrated under reduced pressure. The resultant residue was purified through silica gel column chromatography to give the intermediate I-1 (3.99 g). The yield was 84%.

(2) Synthesis of Intermediate I-2

In an argon atmosphere, a mixture of the intermediate H-1 (3.59 g, 20.0 mmol) and DMF (170 mL) was cooled to 0° C., then N-bromosuccinimide (7.12 g, 40.0 mmol) was added and stirred at room temperature for 24 hours. Water was added to the reaction liquid, and the precipitated solid was taken out by filtration, and purified through silica gel column chromatography to give the intermediate I-2 (6.03 g). The yield was 90%.

(3) Synthesis of Intermediate I

In an argon atmosphere, a mixture of 1-(4,4,5,5-tetramethyl-1,3,2-dioxaborolan-2-yl)-dibenzofuran (10.5 g, 35.8 mmol) synthesized according to the same method as in US 2017/0062729A, the intermediate I-2 (6.00 g, 17.9 mmol), Pd(Amphos)Cl$_2$ (0.255 g, 0.36 mmol), an aqueous 2 M potassium carbonate solution (54 mL) and toluene (160 mL) was stirred at 100° C. for 8 hours. The reaction liquid was cooled to room temperature, and then the filtrate was distilled away. The resultant residue was purified through silica gel column chromatography and recrystallization to give a white solid (7.12 g). The yield was 78%.

In an argon atmosphere, a mixture of 1-(4-chlorophenyl)dibenzo[b,d]furan (7.48 g, 26.8 mmol) synthesized in the same manner as in WO2018/164201, the intermediate A (3.16 g, 12.2 mmol), tris(dibenzylideneacetone)dipalladium (0) (0.223 g, 0.244 mmol), tri-t-butylphosphonium tetrafluoroborate (0.283 g, 0.976 mmol), sodium t-butoxide (3.52 g, 36.6 mmol) and toluene (48.8 mL) was stirred at 100° C. for 4 hours. The reaction liquid was cooled to room temperature, and silica gel (100 mL) was added thereto and stirred. Silica gel was removed by filtration, and the filtrate was concentrated under reduced pressure. The resultant residue was purified through silica gel column chromatography and recrystallization to give a white solid (3.72 g). As a result of mass spectrometry (m/e=744 relative to molecular weight of 743.86), the resultant white solid was the compound 1, and the yield was 41%.

Synthesis Example 2: Synthesis of Compound 2

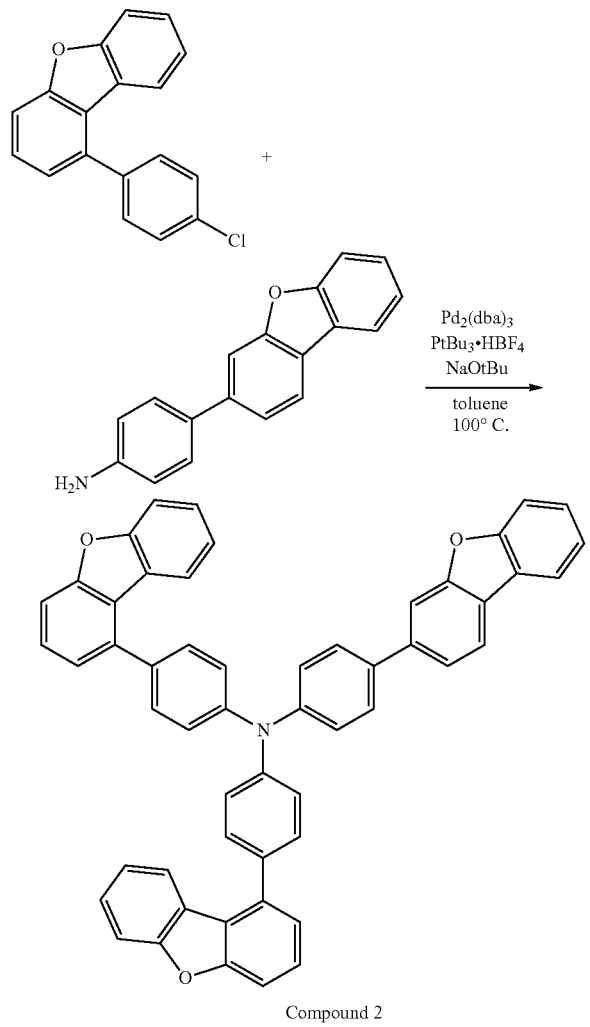

Compound 2

In the same manner as in Synthesis Example 1 except that 4-(3-dibenzo[b,d]furanyl)benzenamine synthesized according to the same method as in WO2018/164239 was used in place of the intermediate A in Synthesis Example 1, a reaction product was produced. As a result of mass spectrometry (m/e=744 relative to molecular weight of 743.86), the resultant reaction product was the compound 2, and the yield was on the same level as in Synthesis Example 1.

Synthesis Example 3: Synthesis of Compound 3

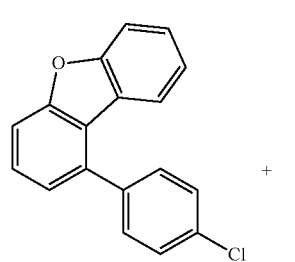

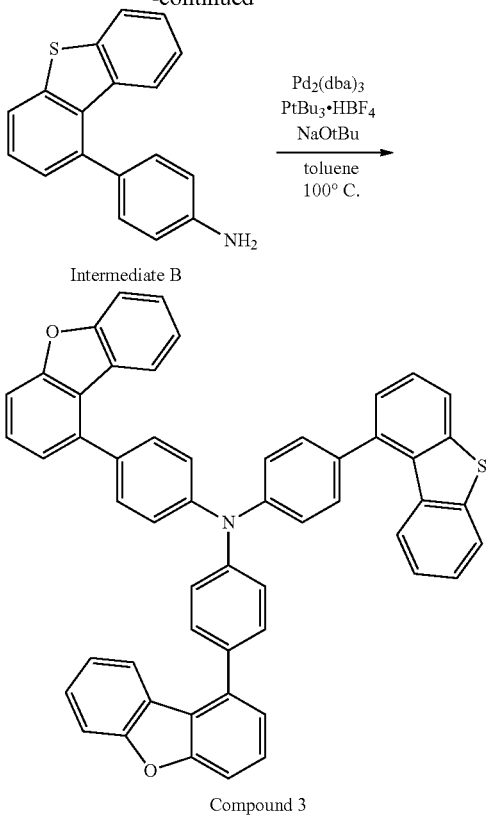

Compound 3

In the same manner as in Synthesis Example 1 except that the intermediate B was used in place of the intermediate A in Synthesis Example 1, a reaction product was produced. As a result of mass spectrometry (m/e=760 relative to molecular weight of 759.92), the resultant reaction product was the compound 3, and the yield was on the same level as in Synthesis Example 1.

Synthesis Example 4: Synthesis of Compound 4

中間体C

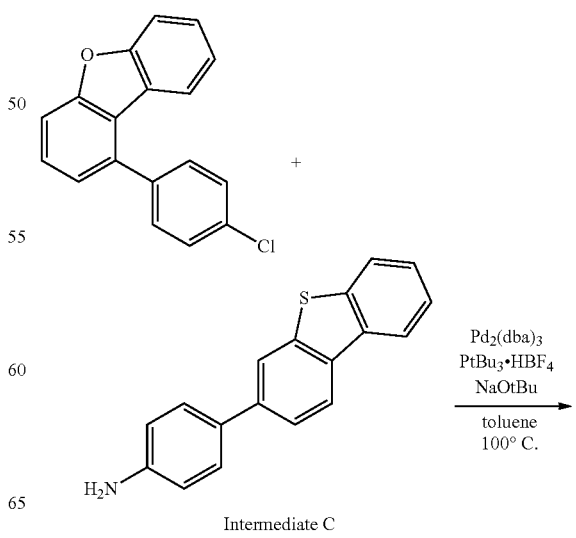

Intermediate C

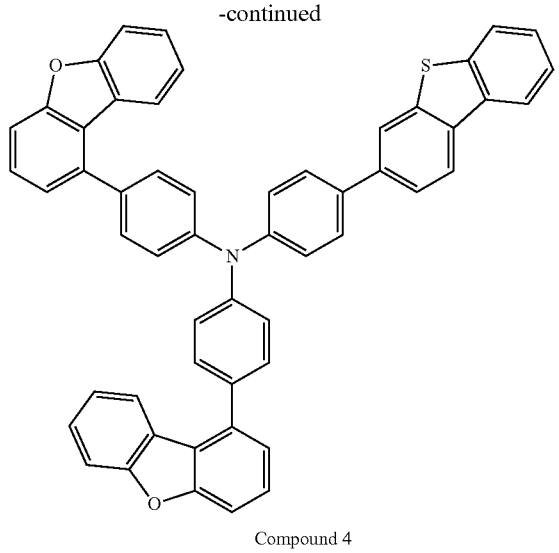

Compound 4

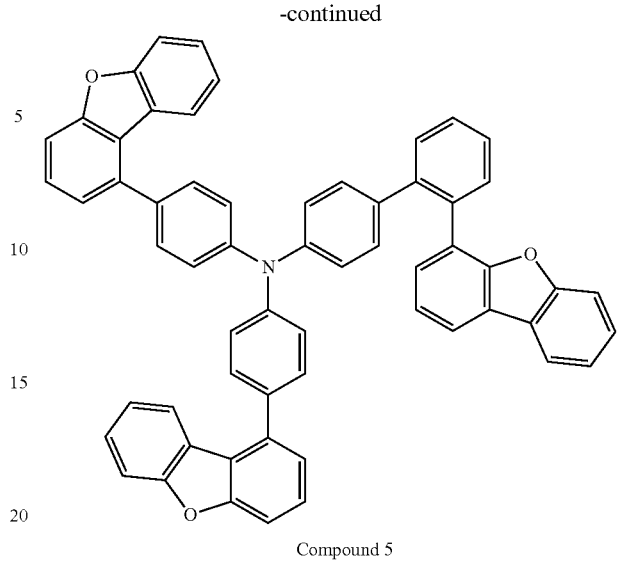

Compound 5

In the same manner as in Synthesis Example 1 except that the intermediate C was used in place of the intermediate A in Synthesis Example 1, a reaction product was produced. As a result of mass spectrometry (m/e=760 relative to molecular weight of 759.92), the resultant reaction product was the compound 4, and the yield was on the same level as in Synthesis Example 1.

Synthesis Example 5: Synthesis of Compound 5

In the same manner as in Synthesis Example 1 except that the intermediate D was used in place of the intermediate A in Synthesis Example 1, a reaction product was produced. As a result of mass spectrometry (m/e=820 relative to molecular weight of 819.96), the resultant reaction product was the compound 5, and the yield was on the same level as in Synthesis Example 1.

Synthesis Example 6: Synthesis of Compound 6

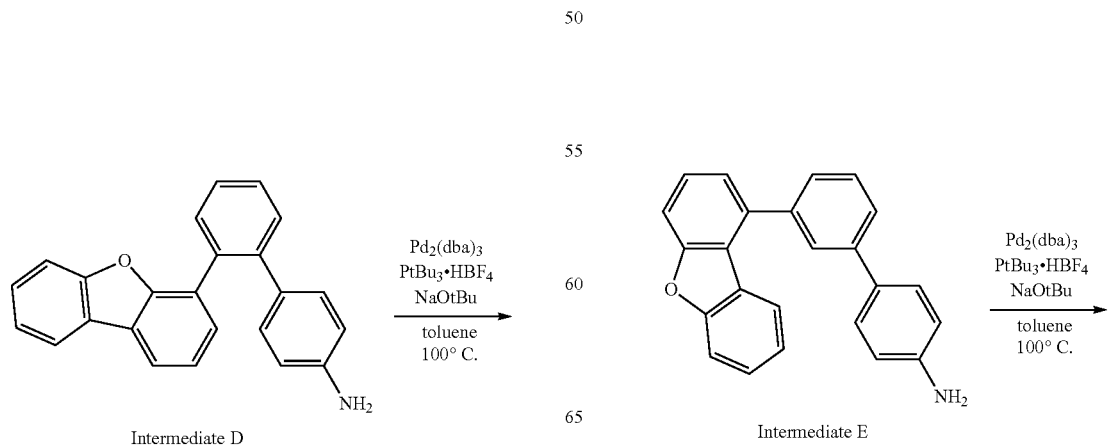

Intermediate D

Intermediate E

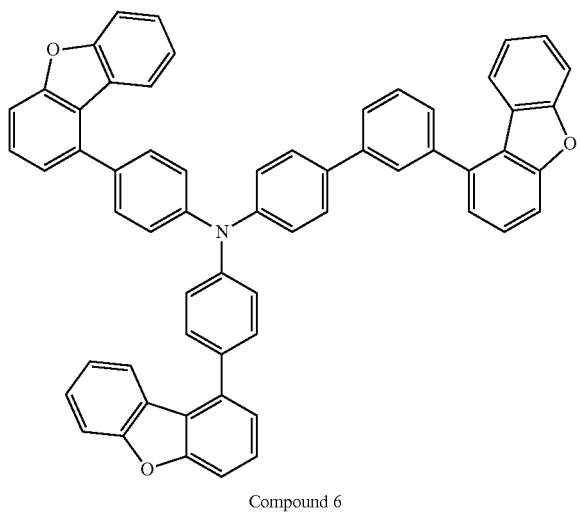

Compound 6

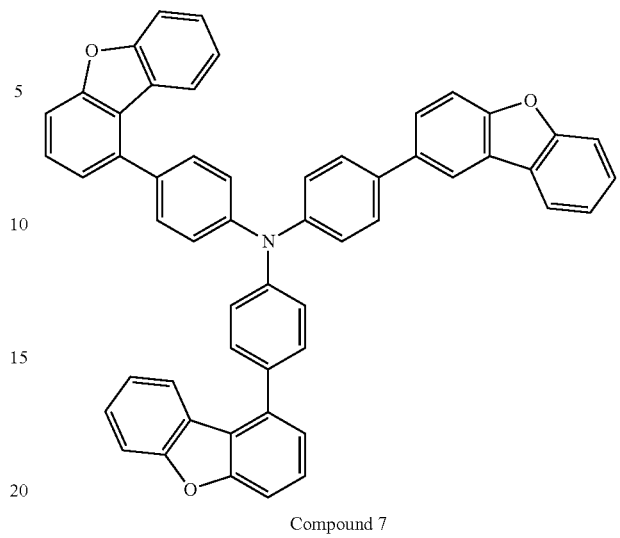

Compound 7

In the same manner as in Synthesis Example 1 except that the intermediate E was used in place of the intermediate A in Synthesis Example 1, a reaction product was produced. As a result of mass spectrometry (m/e=820 relative to molecular weight of 819.96), the resultant reaction product was the compound 6, and the yield was on the same level as in Synthesis Example 1.

Synthesis Example 7: Synthesis of Compound 7

In the same manner as in Synthesis Example 1 except that 4-(2-dibenzo[b,d]furanyl)benzenamine synthesized according to the same method as in WO2014/034795 was used in place of the intermediate A in Synthesis Example 1, a reaction product was produced. As a result of mass spectrometry (m/e=744 relative to molecular weight of 743.86), the resultant reaction product was the compound 7, and the yield was on the same level as in Synthesis Example 1.

Synthesis Example 8: Synthesis of Compound 8

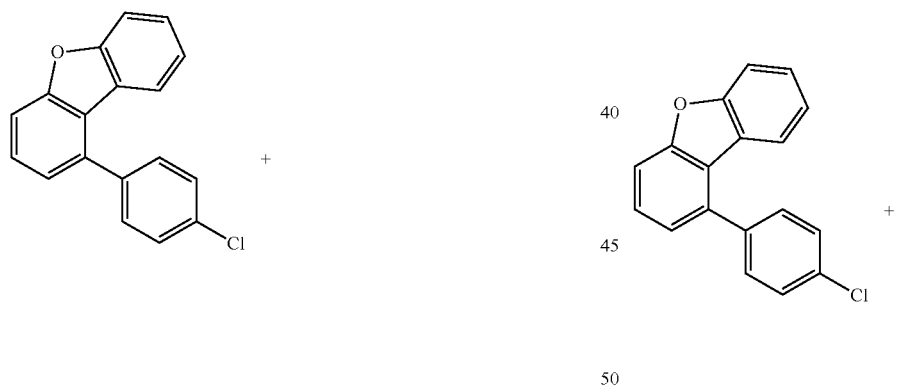

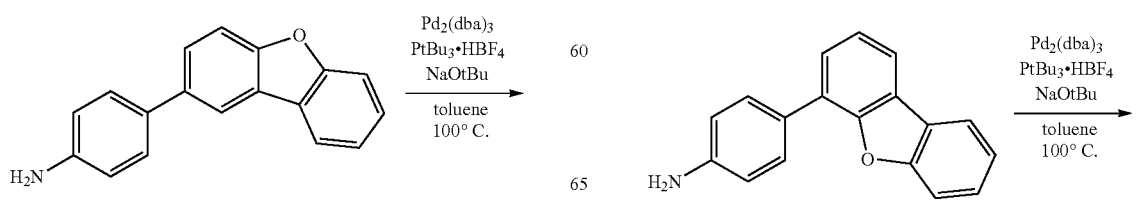

-continued

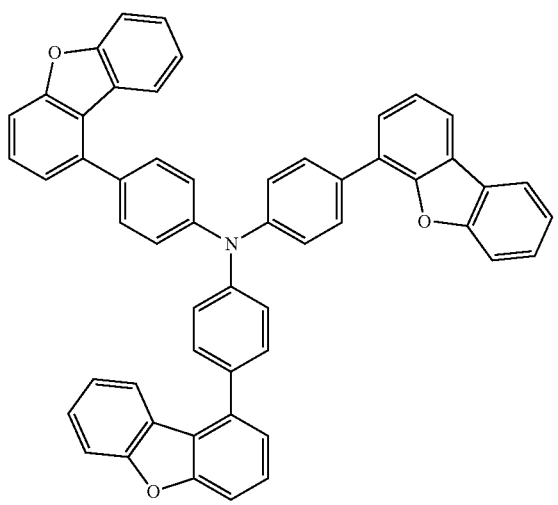

Compound 8

In the same manner as in Synthesis Example 1 except that 4-(4-dibenzo[b,d]furanyl)benzenamine synthesized according to the same method as in WO2016/006711 was used in place of the intermediate A in Synthesis Example 1, a reaction product was produced. As a result of mass spectrometry (m/e=744 relative to molecular weight of 743.86), the resultant reaction product was the compound 8, and the yield was on the same level as in Synthesis Example 1.

Synthesis Example 9: Synthesis of Compound 9

-continued

Compound 9

In the same manner as in Synthesis Example 1 except that the intermediate F was used in place of the intermediate A in Synthesis Example 1, a reaction product was produced. As a result of mass spectrometry (m/e=870 relative to molecular weight of 870.02), the resultant reaction product was the compound 9, and the yield was on the same level as in Synthesis Example 1.

Synthesis Example 10: Synthesis of Compound 10

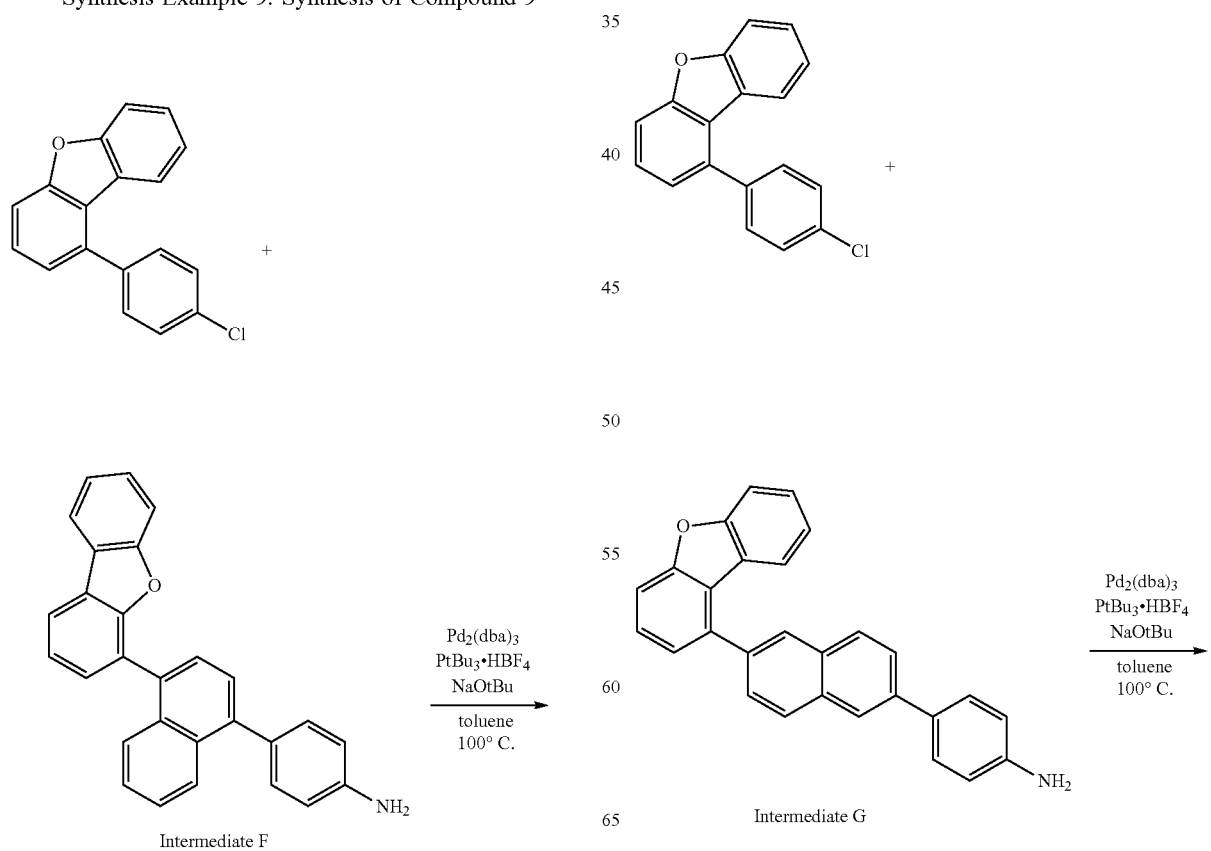

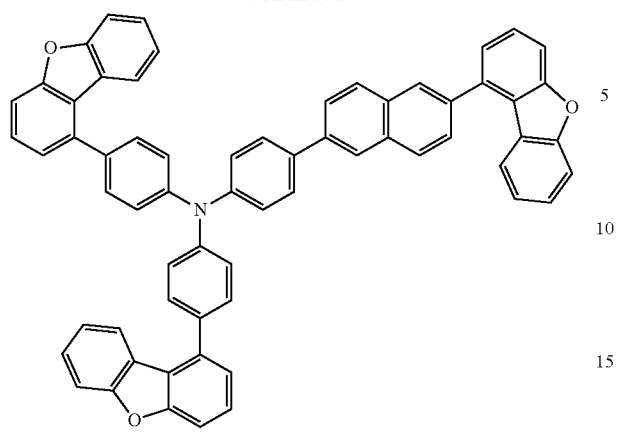

Compound 10

In the same manner as in Synthesis Example 1 except that the intermediate G was used in place of the intermediate A in Synthesis Example 1, a reaction product was produced. As a result of mass spectrometry (m/e=870 relative to molecular weight of 870.02), the resultant reaction product was the compound 10, and the yield was on the same level as in Synthesis Example 1.

Synthesis Example 11: Synthesis of Compound 11

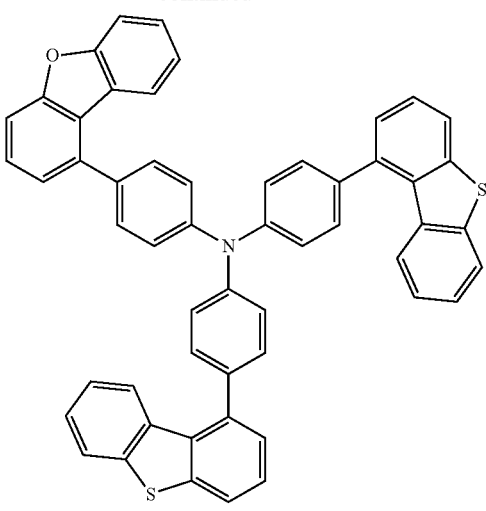

Compound 11

In the same manner as in Synthesis Example 1 except that 1-(4-bromophenyl)dibenzo[b,d]thiophene synthesized according to the same method as in WO2018/066783 was used in place of 1-(4-chlorophenyl)dibenzo[b,d]furan in Synthesis Example 1, a reaction product was produced. As a result of mass spectrometry (m/e=776 relative to molecular weight of 775.98), the resultant reaction product was the compound 10, and the yield was on the same level as in Synthesis Example 1.

Synthesis Example 12: Synthesis of Compound 12

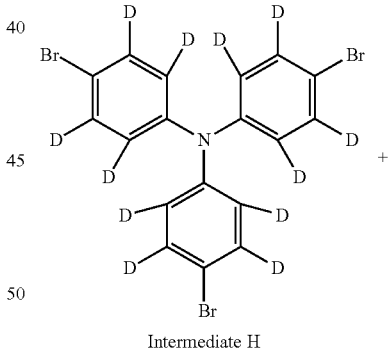

Intermediate H

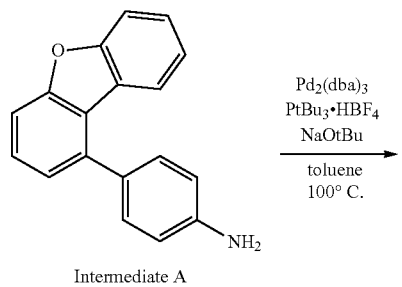

Intermediate A

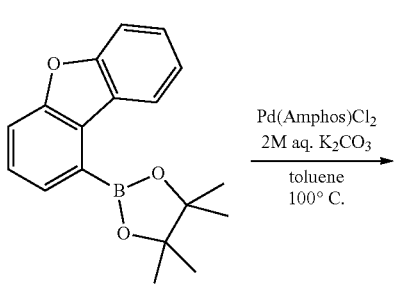

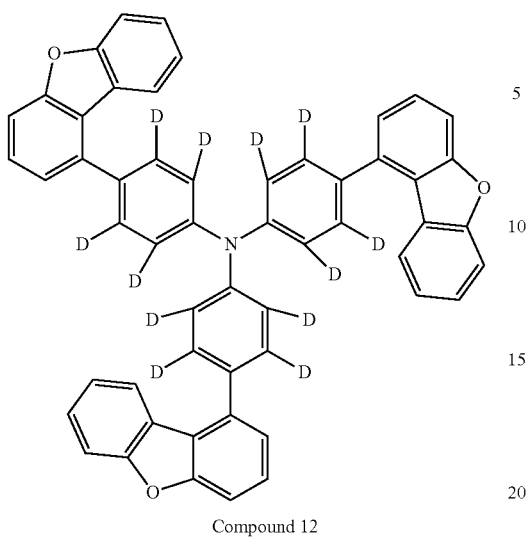

Compound 12

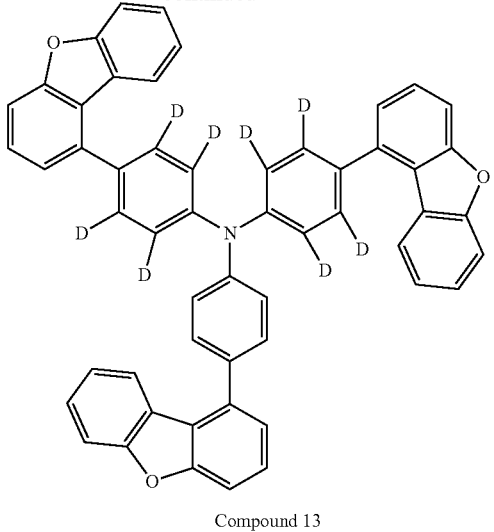

Compound 13

In an argon atmosphere, a mixture of 1-(4,4,5,5-tetramethyl-1,3,2-dioxaborolan-2-yl)dibenzofuran (16.7 g, 56.7 mmol) synthesized according to the same method as in US2017/0062729A, the intermediate H (8.00 g, 16.2 mmol), Pd(Amphos)Cl$_2$ (0.574 g, 0.81 mmol), an aqueous 2 M potassium carbonate solution (73 mL), and toluene (150 mL) was stirred at 100° C. for 8 hours. The reaction liquid was cooled to room temperature, and then the filtrate was distilled away. The resultant residue was purified through silica gel column chromatography and recrystallization to give a white solid (3.20 g). As a result of mass spectrometry (m/e=756 relative to molecular weight of 755.94), the resultant white solid was the compound 12, and the yield was 26%.

Synthesis Example 13: Synthesis of Compound 13

In an argon atmosphere, a mixture of 1-(4-chlorophenyl)dibenzo[b,d]furan (1.80 g, 6.48 mmol) synthesized according to the same method as in WO2018/164201, the intermediate I (3.00 g, 5.89 mmol), tris(dibenzylideneacetone)dipalladium(0) (0.108 g, 0.118 mmol), tri-t-butylphosphonium tetrafluoroborate (0.137 g, 0.471 mmol), sodium t-butoxide (0.849 g, 8.84 mmol) and toluene (30 mL) was stirred at 100° C. for 4 hours. The reaction liquid was cooled to room temperature, and the solution was concentrated under reduced pressure. The resultant residue was purified through silica gel column chromatography and recrystallization to give a white solid (2.52 g). The yield was 57%.

As a result of mass spectrometry (m/e=752 relative to molecular weight of 751.91), the resultant white solid was the compound 13.

Synthesis Example 14: Synthesis of Compound 14

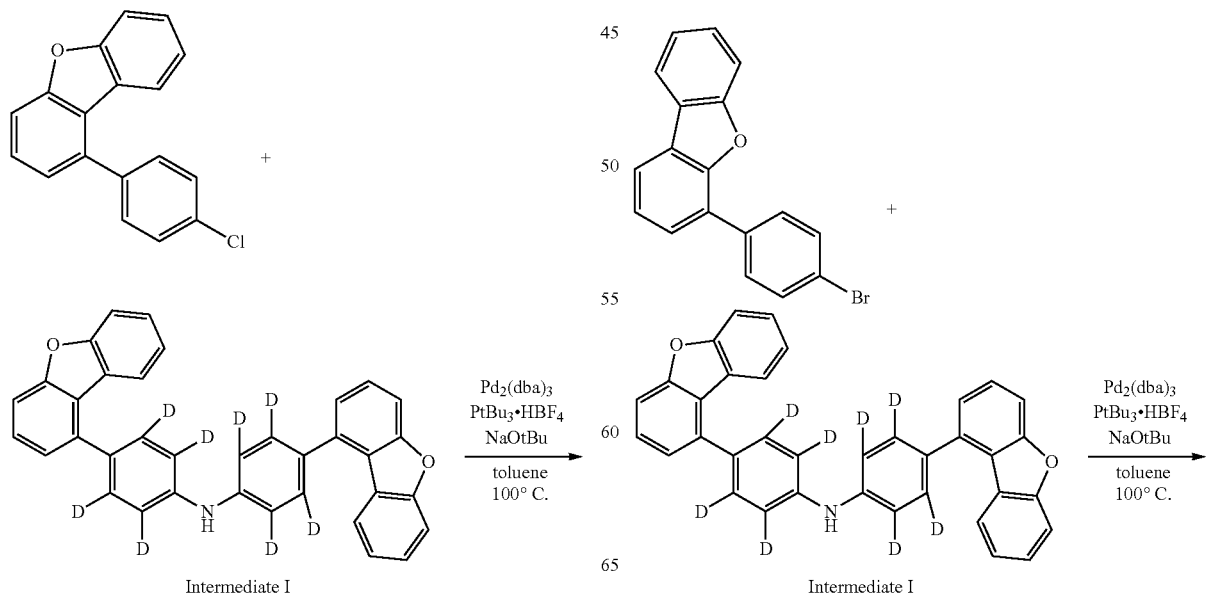

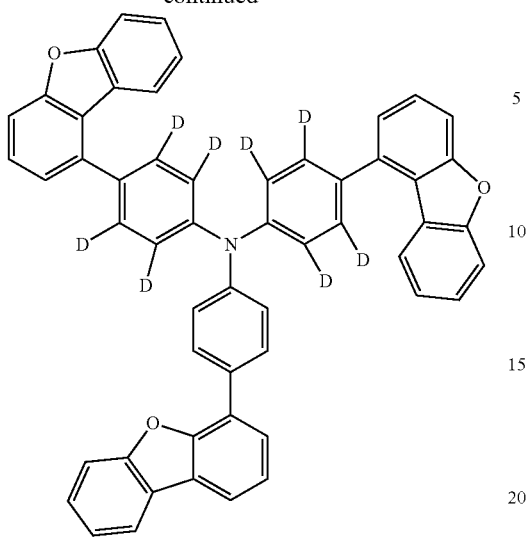

Compound 14

In an argon atmosphere, a mixture of 1-(4-bromophenyl)dibenzo[b,d]furan (2.09 g, 6.48 mmol), the intermediate I (3.00 g, 5.89 mmol), tris(dibenzylideneacetone)dipalladium (0) (0.108 g, 0.118 mmol), tri-t-butylphosphonium tetrafluoroborate (0.137 g, 0.471 mmol), sodium t-butoxide (0.849 g, 8.84 mmol) and toluene (30 mL) was stirred at 100° C. for 4 hours. The reaction liquid was cooled to room temperature, and the solution was concentrated under reduced pressure. The resultant residue was purified through silica gel column chromatography and recrystallization to give a white solid (2.30 g). The yield was 52%.

As a result of mass spectrometry (m/e=752 relative to molecular weight of 751.91), the resultant white solid was the compound 14.

REFERENCE SIGNS LIST 1, 11 Organic EL Device
2 Substrate
3 Anode
4 Cathode
5 Light Emitting Layer
6 Hole Transporting Region (hole transporting layer)
6a First Hole Transporting Layer
6b Second Hole Transporting Layer
7 Electron Transporting Region (electron transporting layer)
7a First Electron Transporting Layer
7b Second Electron Transporting Layer
10, 20 Light Emitting Unit

The invention claimed is:

1. A compound represented by the following formula (1):

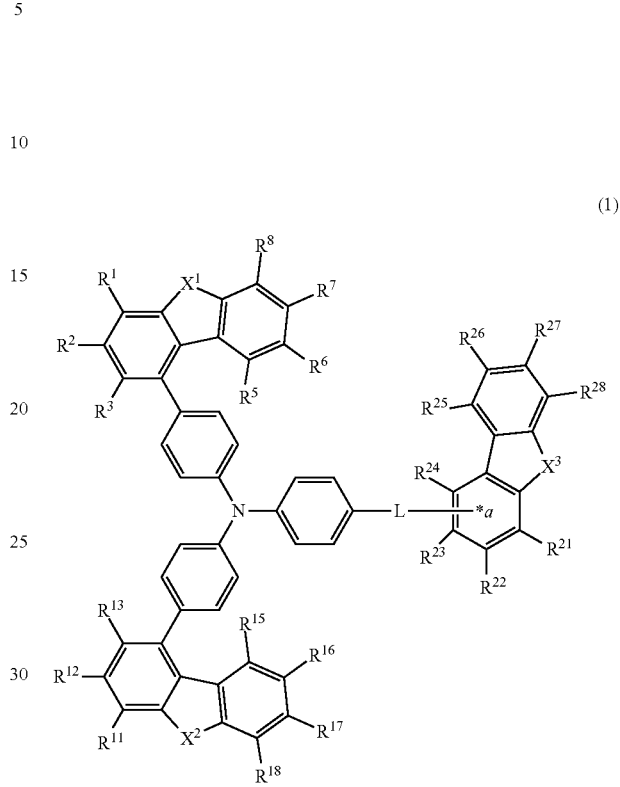

(1)

wherein:

one of $X^1$ and $X^2$ is an oxygen atom, and the other is an oxygen atom or a sulfur atom, $X^3$ is selected from an oxygen atom or a sulfur atom, L is selected from a single bond, a substituted or unsubstituted phenylene group, and a substituted or unsubstituted naphthylene group, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ each are independently selected from a hydrogen atom, an unsubstituted alkyl group having 1 to 6 carbon atoms, and an unsubstituted cycloalkyl group having 3 to 20 ring carbon atoms, provided that one of $R^{21}$ to $R^{24}$ is a single bond bonding to L via *a.

2. The compound according to claim 1, which is represented by any of the following formulae (2) to (5);

(2)

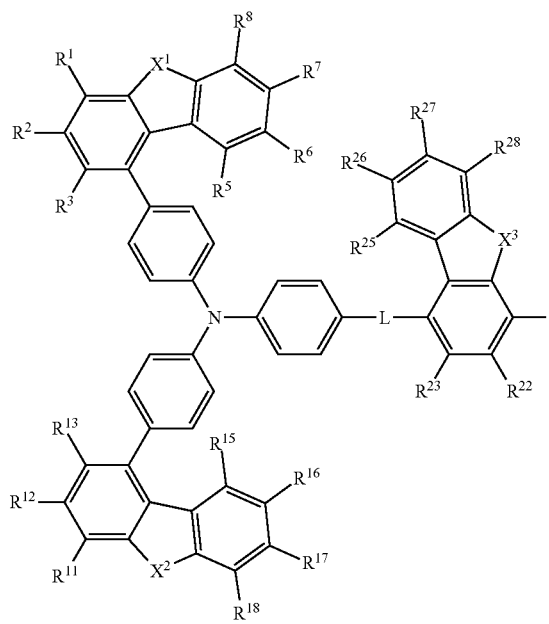

(3)

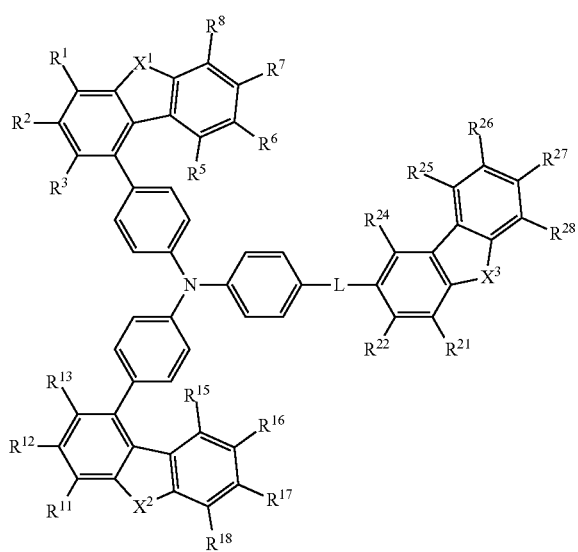

(4)

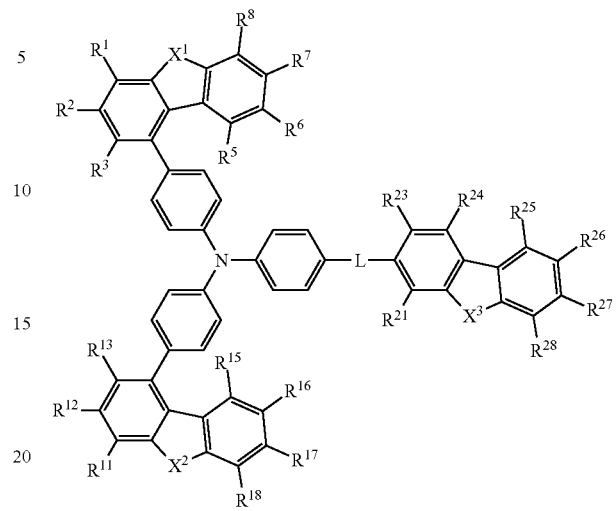

(5)

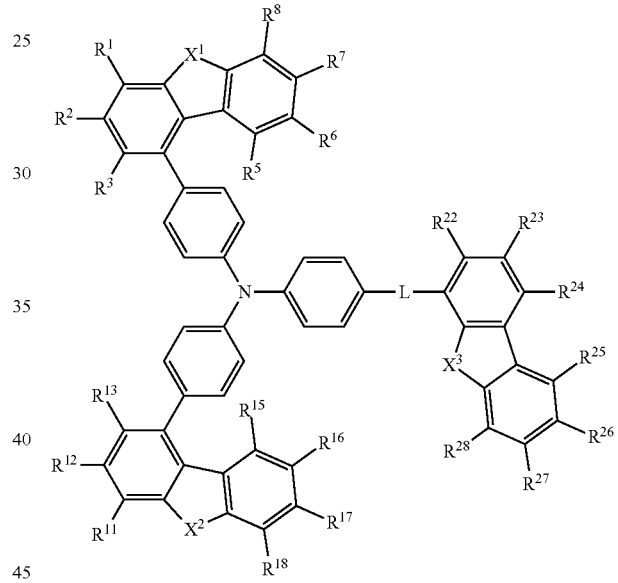

wherein $X^1$, $X^2$, $X^3$, L, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the formula (1).

3. The compound according to claim 1, wherein $X^1$ and $X^2$ are oxygen atoms.

4. The compound according to claim 1, wherein $R^1$ and $R^{11}$ are the same, $R^2$ and $R^{12}$ are the same, $R^3$ and $R^{13}$ are the same, $R^5$ and $R^{15}$ are the same, $R^6$ and $R^{16}$ are the same, $R^7$ and $R^{17}$ are the same, and $R^8$ and $R^{18}$ are the same.

5. The compound according to claim 1, wherein $X^1$, $X^2$, and $X^3$ are oxygen atoms.

6. The compound according to claim 1, wherein $X^1$ and $X^2$ are oxygen atoms, and $X^3$ is a sulfur atom.

7. The compound according to claim 1, wherein one of $X^1$ and $X^2$ is an oxygen atom and the other is a sulfur atom, and X3 is a sulfur atom.

8. The compound according to claim 1, wherein one of $X^1$ and $X^2$ is an oxygen atom and the other is a sulfur atom, and X3 is an oxygen atom.

9. The compound according to claim 1, represented by any of the following formulae (6) to (9) where L is a single bond:

(6)
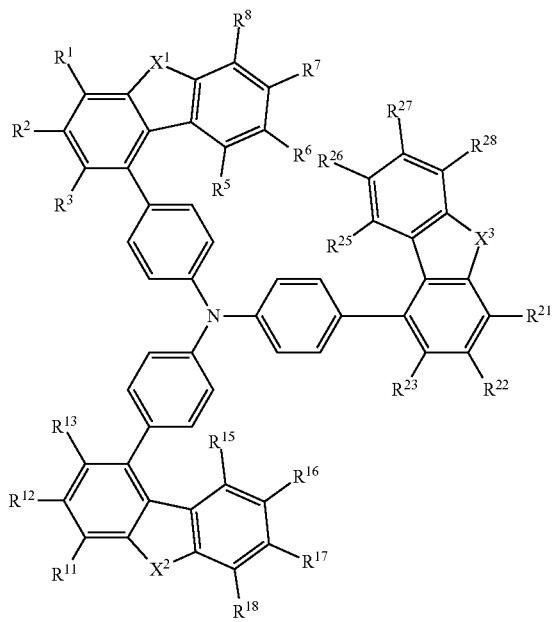

(7)
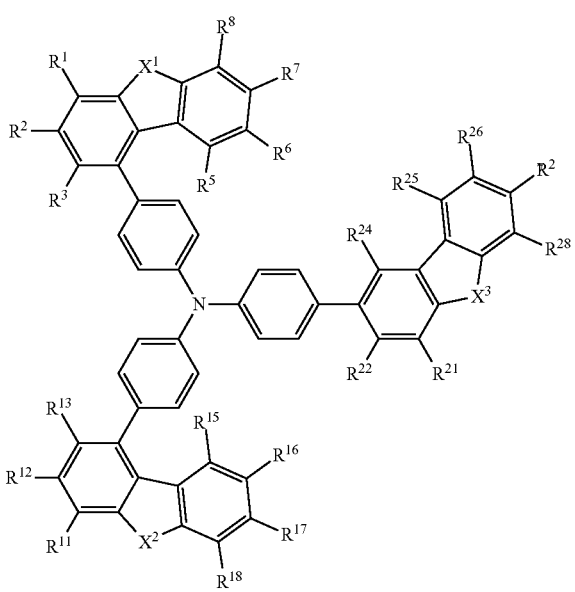

(8)
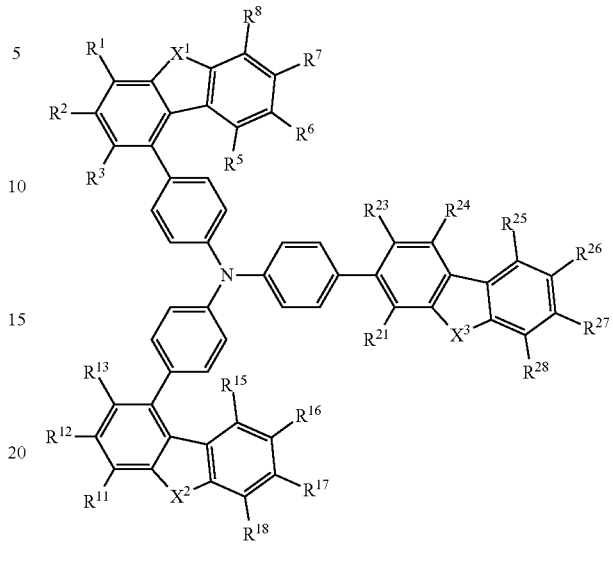

(9)
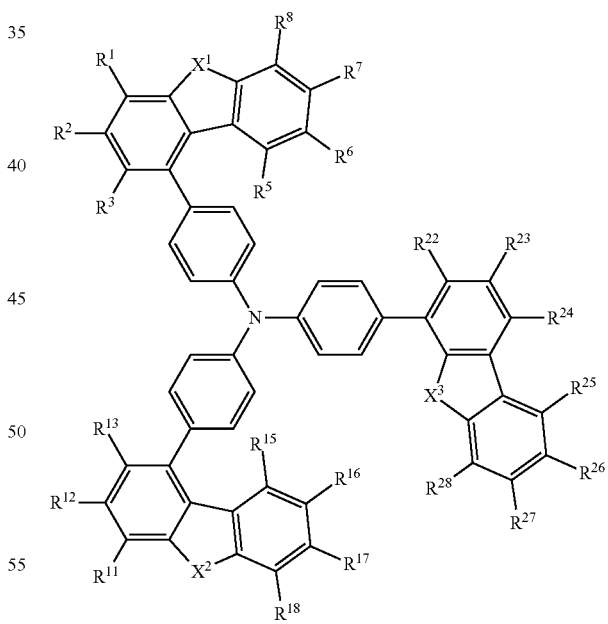

wherein $X^1$, $X^2$, $X^3$, $R^1$ to $R^3$, $R^5$ to $R^8$, $R^{11}$ to $R^{13}$, $R^{15}$ to $R^{18}$, $R^{21}$ to $R^{24}$, and $R^{25}$ to $R^{28}$ are as defined in the formula (1).

10. The compound according to claim 1, wherein L is a substituted or unsubstituted phenylene group, and the unsubstituted phenylene group is selected from an o-phenylene group, a m-phenylene group and a p-phenylene group.

11. The compound according to claim 10, represented by any of the following formulae (10) to (13):

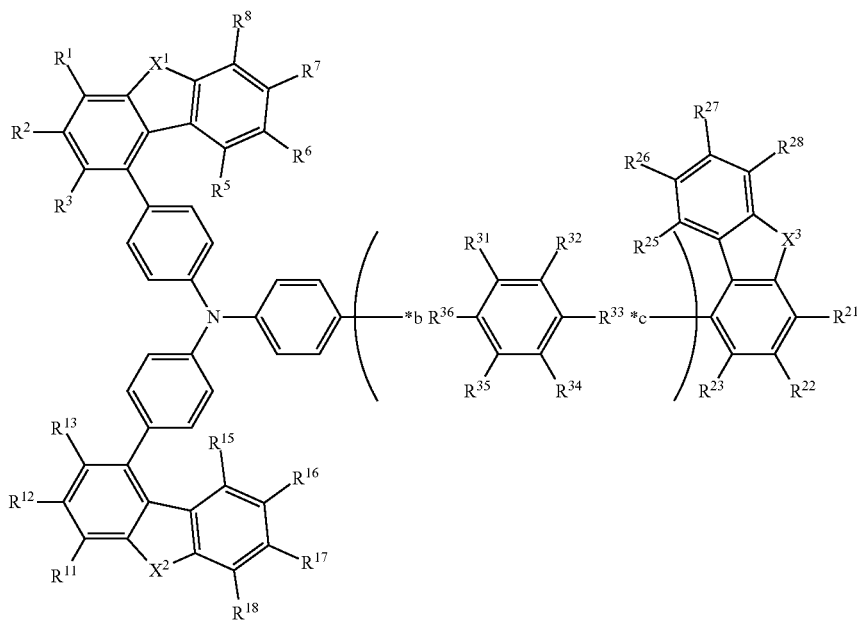
(10)
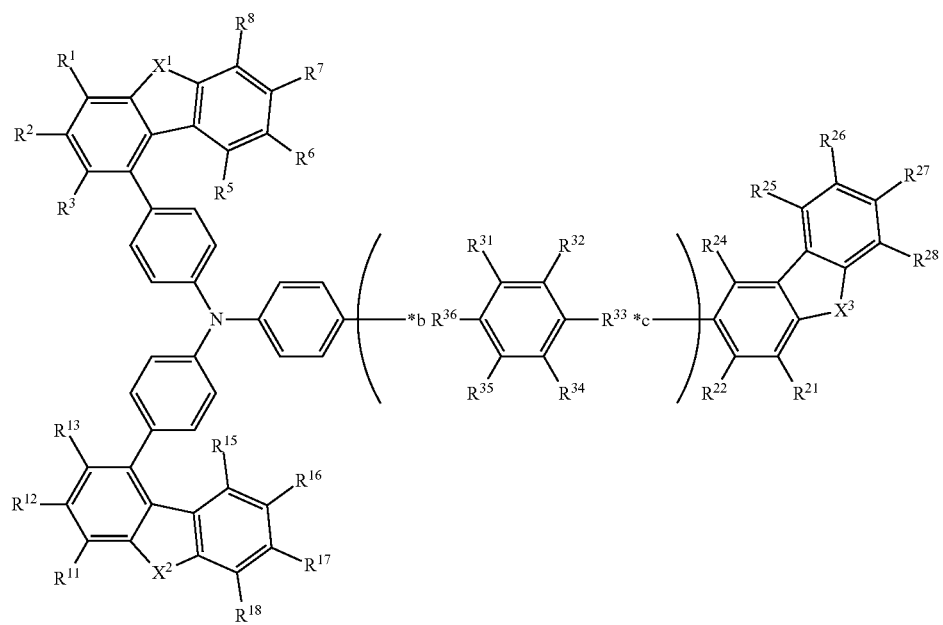
(11)

(12)

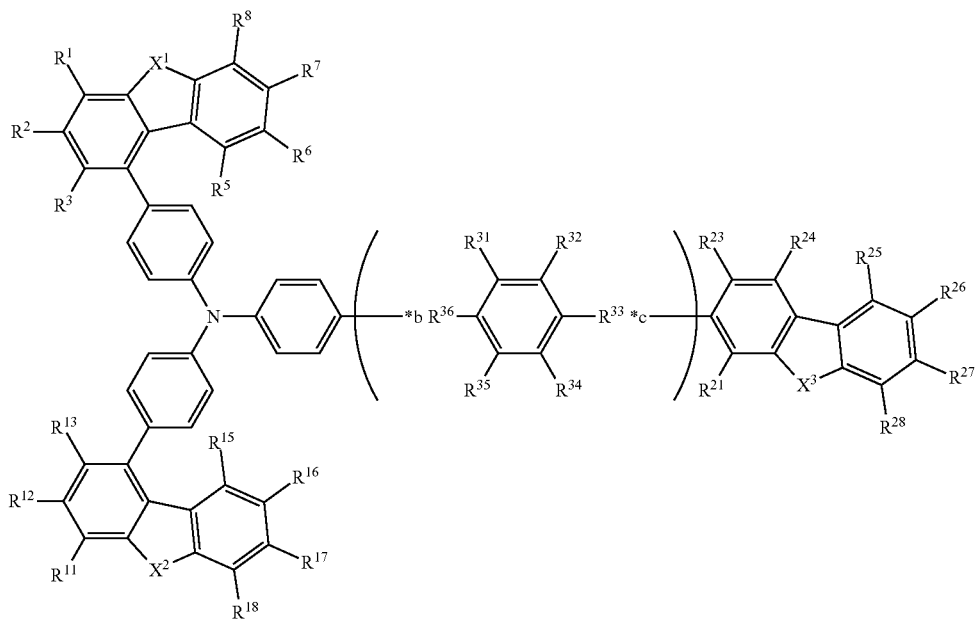

(13)

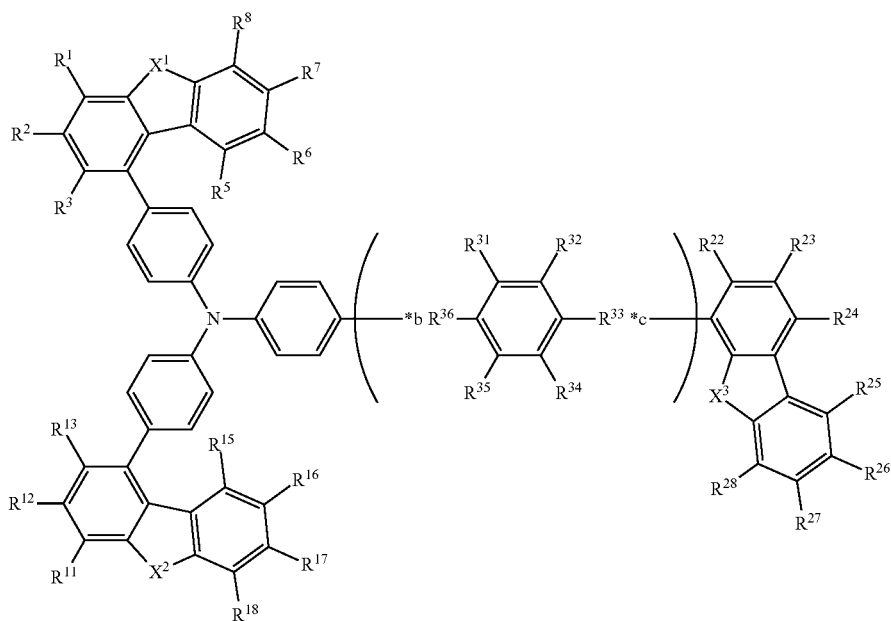

wherein:
$X^1, X^2, X^3, R^1$ to $R^3, R^5$ to $R^8, R^{11}$ to $R^{13}, R^{15}$ to $R^{18}, R^{21}$ to $R^{24}$, and $R^{25}$ to $R^{28}$ are as defined in the formula (1),
$R^{31}$ to $R^{36}$ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by $—Si(R^{901})(R^{902})(R^{903})$, a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group, provided that one selected from $R^{31}$ to $R^{36}$ is a single bond bonding to *b, and the other selected from $R^{31}$ to $R^{36}$ is a single bond bonding to *c, $R^{901}, R^{902}$, and $R^{903}$ each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms.

12. The compound according to claim 11, wherein $R^{31}$ to $R^{36}$ not a single bond bonding to *b and not a single bond bonding to *c are all hydrogen atoms.

13. The compound according to claim 1, wherein L is a substituted or unsubstituted naphthylene group.

14. The compound according to claim 13, wherein the substituted or unsubstituted naphthylene group is selected from a substituted or unsubstituted 1,4-naphthylene group and a substituted or unsubstituted 2,6-naphthylene group.

15. The compound according to claim 13, represented by any of the following formulae (14) to (17):

(14)

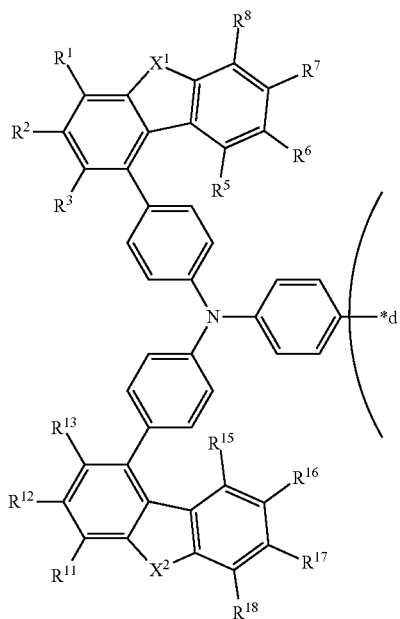 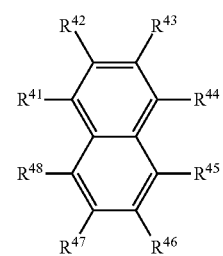 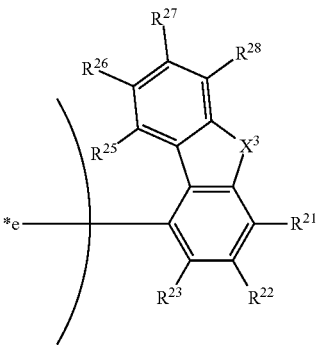

(15)

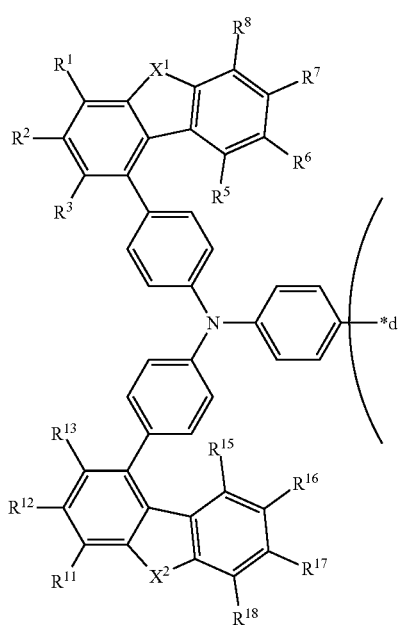 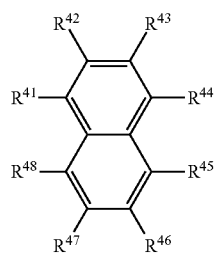 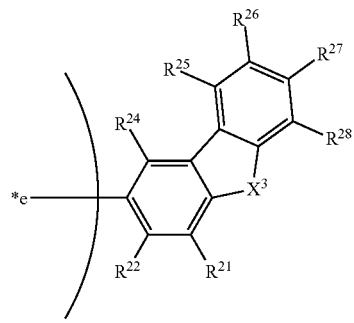

-continued (16)

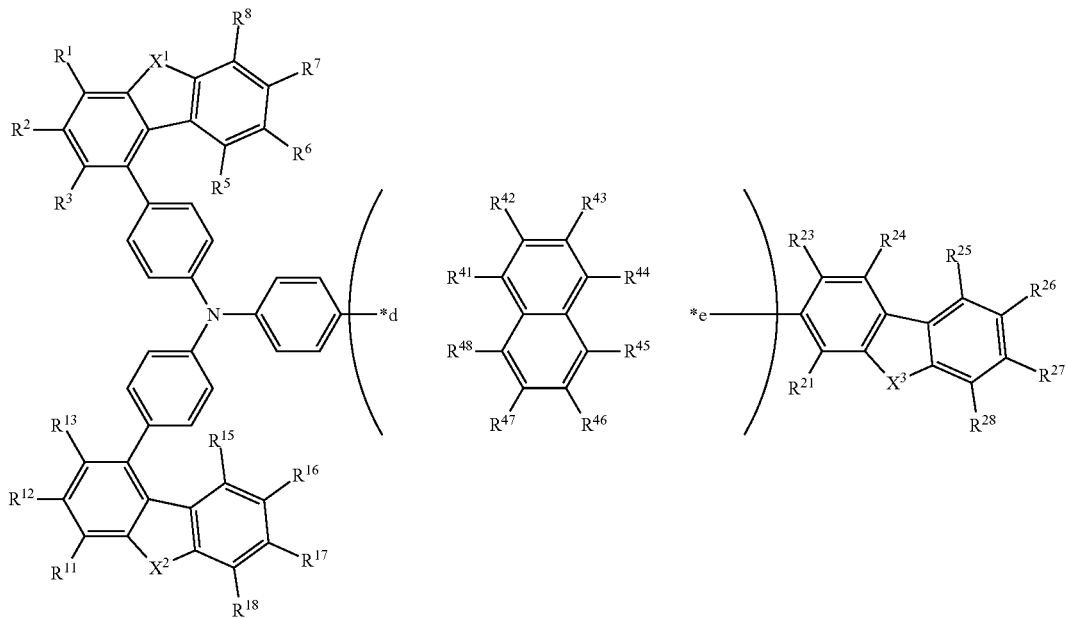

(17)

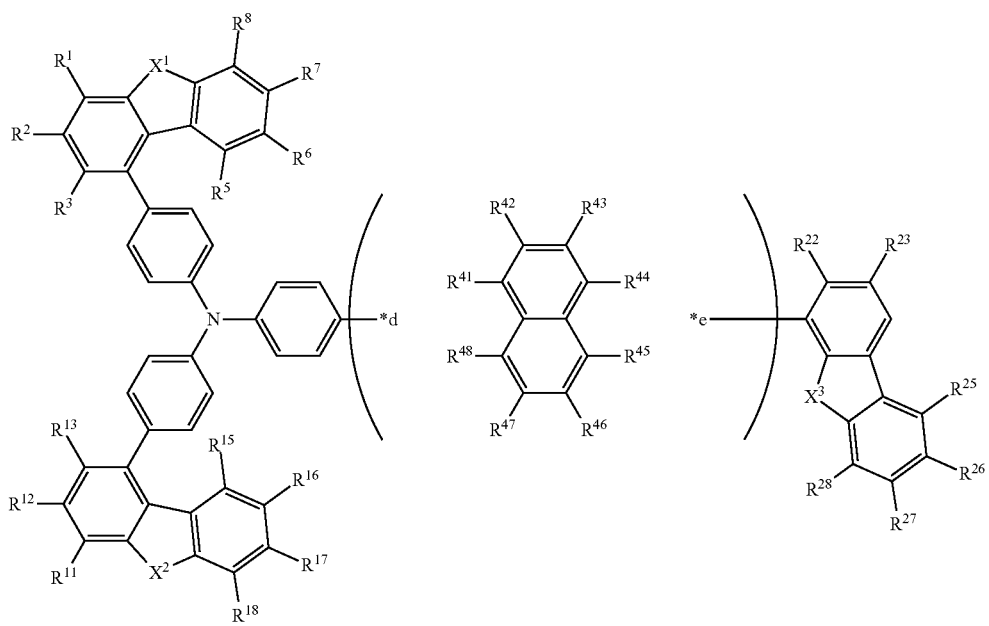

wherein:
X¹, X², X³, R¹ to R³, R⁵ to R⁸, R¹¹ to R¹³, R¹⁵ to R¹⁸, R²¹ to R²⁴, and R²⁵ to R²⁸ are as defined in the formula (1),
R⁴¹ to R⁴⁸ each are independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a group represented by —Si(R⁹⁰¹)(R⁹⁰²)(R⁹⁰³), a halogen atom, a substituted or unsubstituted haloalkyl group having 1 to 50 carbon atoms, a substituted or unsubstituted alkoxy group having 1 to 50 carbon atoms, a substituted or unsubstituted aryloxy group having 6 to 50 ring carbon atoms, a substituted or unsubstituted haloalkoxy group having 1 to 50 carbon atoms, a substituted or unsubstituted aralkyl group having 7 to 50 carbon atoms, a nitro group, and a cyano group,
provided that one selected from R⁴¹ to R⁴⁸ is a single bond bonding to *d, and the other selected from R⁴¹ to R⁴⁸ is a single bond bonding to *e,
R⁹⁰¹, R⁹⁰², and R⁹⁰³ each are independently selected from a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, and a substituted or unsubstituted cycloalkyl group having 3 to 50 ring carbon atoms.

16. The compound according to claim 15, wherein $R^{41}$ to $R^{48}$ not a single bond bonding to *d and not a single bond bonding to *e are all hydrogen atoms.

17. The compound according to claim 1, containing at least one heavy hydrogen atom.

18. A material for organic electroluminescent devices containing the compound of claim 1.

19. An electroluminescent device having an anode, a cathode, and an organic layer arranged between the anode and the cathode, wherein the organic layer includes a light-emitting layer, and at least one layer of the organic layer contains the compound of claim 1.

20. The organic electroluminescent device according to claim 19, wherein the compound contains at least one heavy hydrogen atom.

21. The organic electroluminescent device according to claim 19, wherein the organic layer contains a hole transporting region between the anode and the light emitting layer, and the hole transporting region contains the compound.

22. The organic electroluminescent device according to claim 21, wherein the hole transporting region contains a first hole transporting layer on the anode side and a second hole transporting layer on the cathode side, and the first hole transporting layer or the second hole transporting layer, or both the two contain the compound.

23. The organic electroluminescent device according to claim 22, wherein the first hole transporting layer contains the compound and the second hole transporting layer does not contain the compound.

24. The organic electroluminescent device according to claim 22, wherein the second hole transporting layer contains the compound and the first hole transporting layer does not contain the compound.

25. The compound according to claim 1, which is selected from the following compounds 1 to 14:

Compound 1

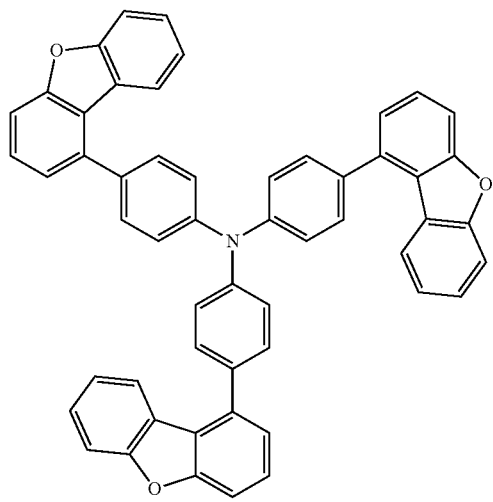

-continued

Compound 2

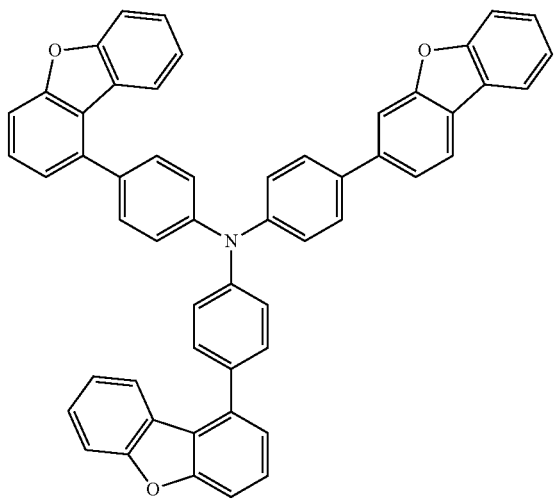

Compound 3

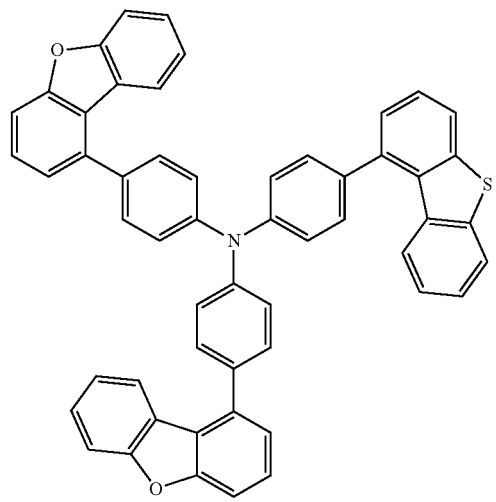

Compound 4

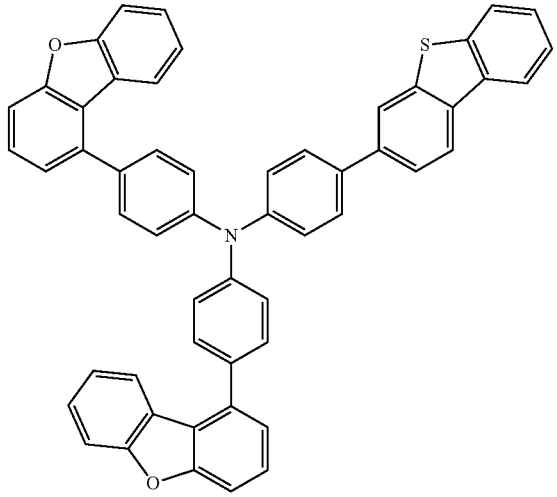

Compound 5
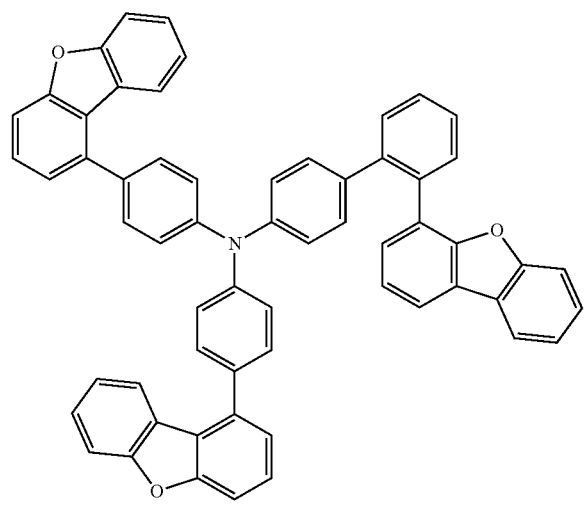
Compound 8
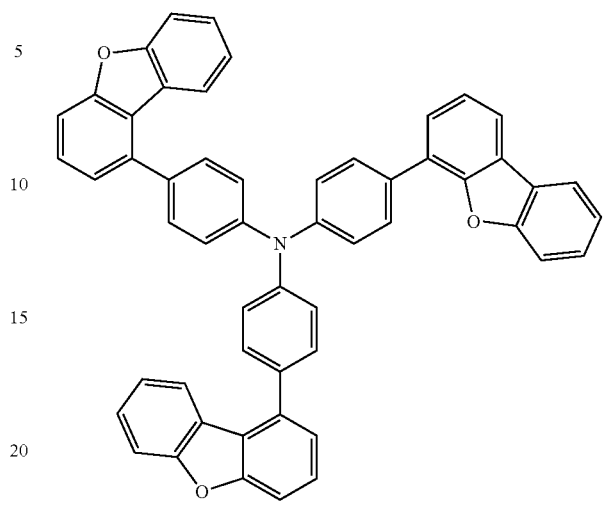
Compound 6
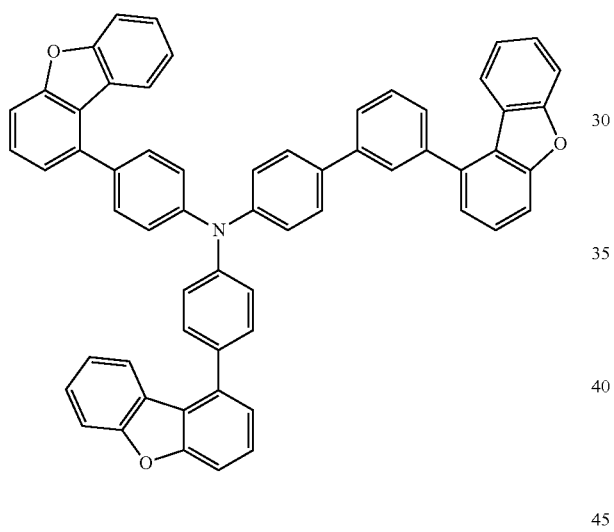
Compound 9
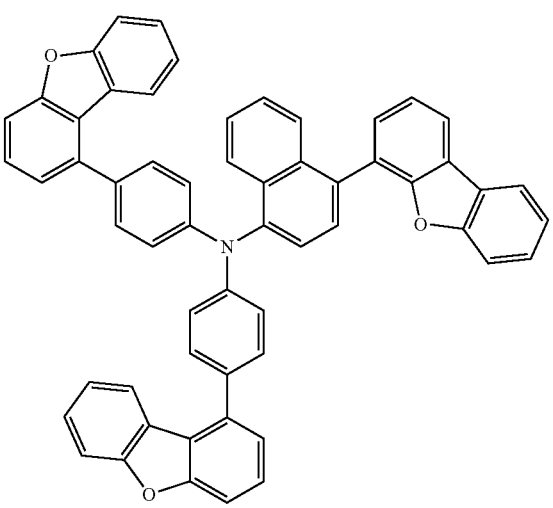
Compound 7
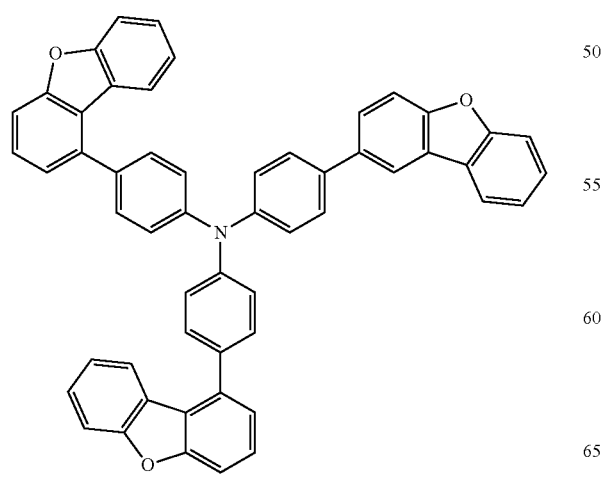
Compound 10
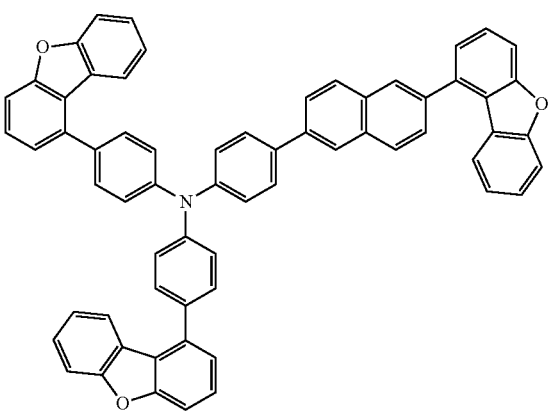

Compound 11

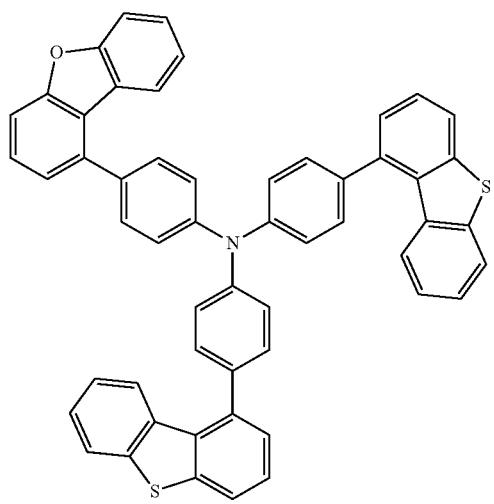

Compound 12

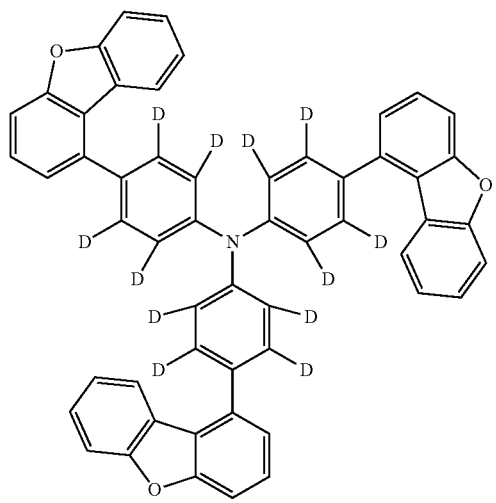

Compound 13

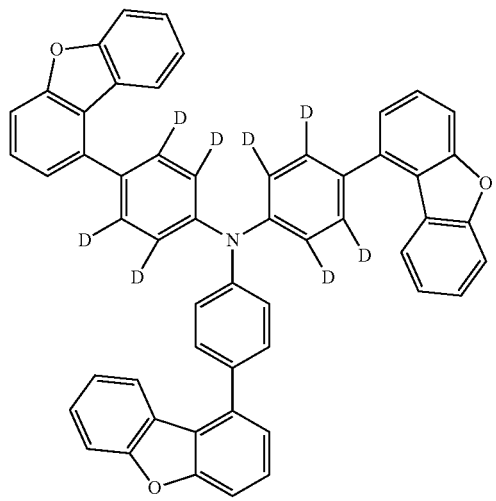

Compound 14

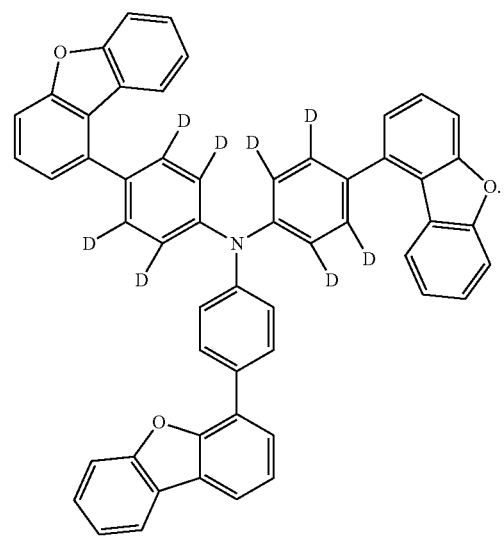

26. The organic electroluminescent device according to claim 22, wherein the hole transporting region contains a hole injecting layer, and the hole injecting layer is included between the anode and the first hole transporting layer on the anode side.

27. The organic electroluminescent device according to claim 26, wherein the hole transporting region contains the hole injecting layer, the first hole transporting layer and the second hole transporting layer in this order, and the second hole transporting layer contains the compound.

28. The organic electroluminescent device according to claim 27, wherein the second hole transporting layer is adjacent to the light emitting layer.

29. The compound according to claim 1, represented by any of the following compounds:

Compound 1

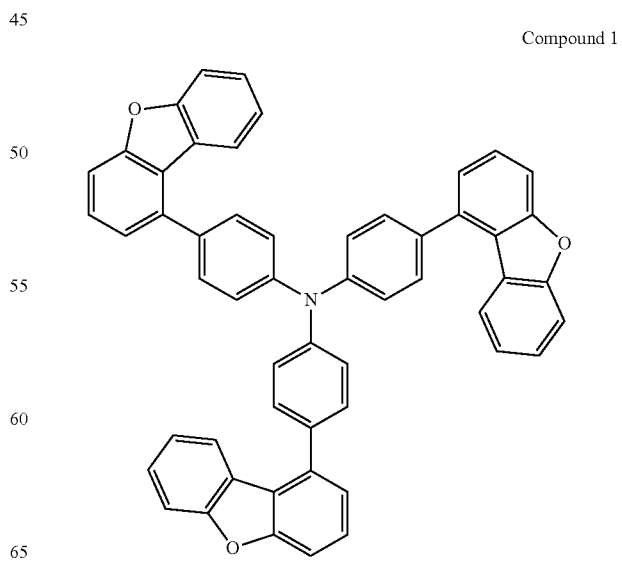

Compound 3
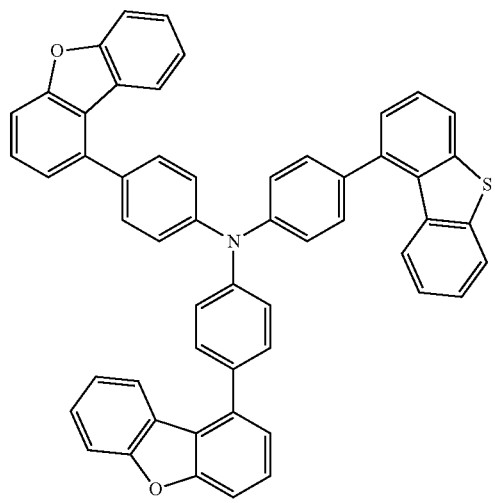
Compound 7
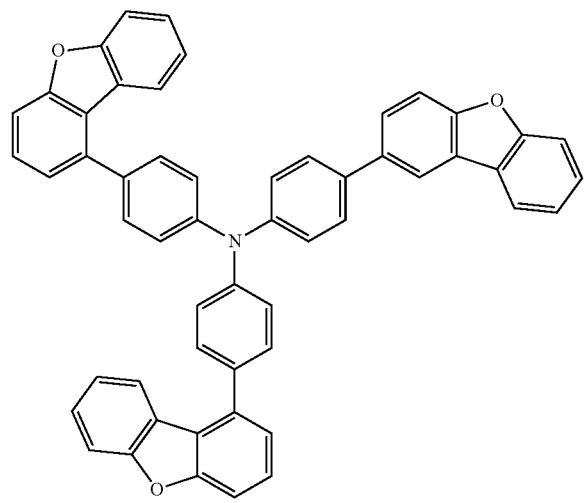
Compound 8
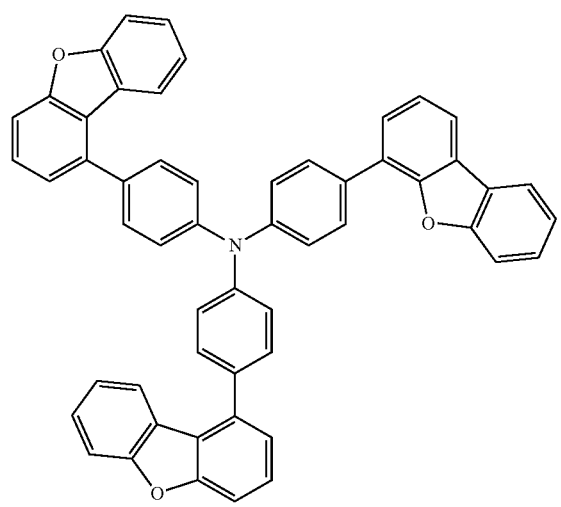
Compound 11
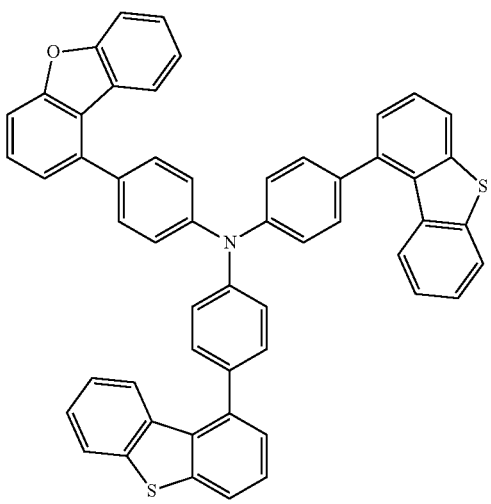
Compound 12
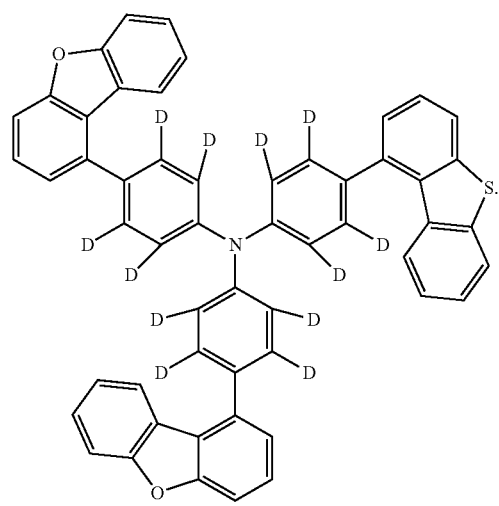
* * * * *